US009655854B2

(12) United States Patent
Yeleswaram et al.

(10) Patent No.: US 9,655,854 B2
(45) Date of Patent: May 23, 2017

(54) SUSTAINED RELEASE DOSAGE FORMS FOR A JAK1 INHIBITOR

(71) Applicant: Incyte Corporation, Wilmington, DE (US)

(72) Inventors: Krishnaswamy Yeleswaram, Landenberg, PA (US); Bhavnish Parikh, Avondale, PA (US); Dilip P. Modi, Newark, DE (US); Trupti Sheth, Newark, DE (US)

(73) Assignee: Incyte Corporation, Wilmington, DE (US)

( * ) Notice: Subject to any disclaimer, the term of this patent is extended or adjusted under 35 U.S.C. 154(b) by 0 days.

(21) Appl. No.: 14/453,129

(22) Filed: Aug. 6, 2014

(65) Prior Publication Data

US 2015/0065484 A1  Mar. 5, 2015

Related U.S. Application Data

(60) Provisional application No. 61/913,066, filed on Dec. 6, 2013, provisional application No. 61/863,325, filed on Aug. 7, 2013.

(51) Int. Cl.
A61K 31/519 (2006.01)
C07D 487/04 (2006.01)
C07D 471/04 (2006.01)
A61K 9/20 (2006.01)

(52) U.S. Cl.
CPC .......... A61K 9/2054 (2013.01); A61K 9/2009 (2013.01); A61K 9/2013 (2013.01); A61K 9/2018 (2013.01); A61K 9/2031 (2013.01); A61K 9/2059 (2013.01); A61K 31/519 (2013.01)

(58) Field of Classification Search
USPC .................................................. 514/210.21
See application file for complete search history.

(56) References Cited

U.S. PATENT DOCUMENTS

| | | |
|---|---|---|
| 2,985,589 A | 5/1961 | Broughton et al. |
| 3,832,460 A | 8/1974 | Kosti |
| 4,402,832 A | 9/1983 | Gerhold |
| 4,498,991 A | 2/1985 | Oroskar |
| 4,512,984 A | 4/1985 | Seufert et al. |
| 4,548,990 A | 10/1985 | Mueller et al. |
| 4,814,477 A | 3/1989 | Wijnberg et al. |
| 5,378,700 A | 1/1995 | Sakuma et al. |
| 5,510,101 A | 4/1996 | Stroppolo |
| 5,521,184 A | 5/1996 | Zimmermann |
| 5,630,943 A | 5/1997 | Grill |
| 5,795,909 A | 8/1998 | Shashoua et al. |
| 5,856,326 A | 1/1999 | Anthony |
| 5,919,779 A | 7/1999 | Proudfoot et al. |
| 6,060,038 A | 5/2000 | Burns |
| 6,075,056 A | 6/2000 | Quigley, Jr. et al. |
| 6,136,198 A | 10/2000 | Adam et al. |
| 6,217,895 B1 | 4/2001 | Guo et al. |
| 6,335,342 B1 | 1/2002 | Longo et al. |
| 6,375,839 B1 | 4/2002 | Adam et al. |
| 6,413,419 B1 | 7/2002 | Adam et al. |
| 6,486,322 B1 | 11/2002 | Longo et al. |
| 6,548,078 B2 | 4/2003 | Guo |
| 6,569,443 B1 | 5/2003 | Dawson |
| 6,579,882 B2 | 6/2003 | Stewart et al. |
| 6,624,138 B1 | 9/2003 | Sung et al. |
| 6,635,762 B1 | 10/2003 | Blumenkopf et al. |
| 6,712,973 B2 | 3/2004 | Adam et al. |
| 6,713,089 B1 | 3/2004 | Bertelsen et al. |
| 6,852,727 B2 | 2/2005 | Goulet et al. |
| 6,953,776 B2 | 10/2005 | Di Napoli |
| 7,005,436 B2 | 2/2006 | Lloyd et al. |
| 7,167,750 B2 | 1/2007 | Knudson et al. |
| 7,265,108 B2 | 9/2007 | Ozaki |
| 7,335,667 B2 | 2/2008 | Rodgers et al. |
| 7,358,255 B2 | 4/2008 | Nakamura |
| 7,517,870 B2 | 4/2009 | Auricchio |
| 7,598,257 B2 | 10/2009 | Rodgers et al. |
| 7,745,437 B2 | 6/2010 | Ren et al. |
| 7,750,007 B2 | 7/2010 | Bearss et al. |
| 7,834,022 B2 | 11/2010 | Rodgers et al. |
| 8,053,433 B2 | 11/2011 | Rodgers et al. |
| 8,158,616 B2 | 4/2012 | Rodgers et al. |
| 8,309,718 B2 | 11/2012 | Li et al. |
| 8,410,265 B2 | 4/2013 | Zhou et al. |
| 8,415,362 B2 | 4/2013 | Rodgers et al. |
| 8,420,629 B2 | 4/2013 | Rodgers et al. |
| 8,440,679 B2 * | 5/2013 | McAllister .......... C07D 471/04 514/264.1 |
| 8,445,488 B2 | 5/2013 | Rodgers et al. |

(Continued)

FOREIGN PATENT DOCUMENTS

| | | |
|---|---|---|
| DE | 30 36 390 | 5/1982 |
| EP | 0223420 | 5/1987 |

(Continued)

OTHER PUBLICATIONS

26th Annual JPMorgan Healthcare Conference presentation dated Jan. 8, 2008 (28 pages).
Abe, et al., Heterocycles, "Effective Methods for Introducing Some Aryl and Heteroaryl Substituent onto 1-Azaazulene Nuclei", 66, 229-240 (2005).
Abelson et al., "Alternate reference values for tear film break-up time in normal and dry eye populations, Lacrimal Gland, Tear Film, and Dry Eye Syndromes 3 Part B", Adv Exp Med Biol, 2002; 506:1121-1125.
Abelson et al., "Dry eye syndrome: diagnosis, clinical trials, and pharmaceutical treatment-'improving clinical trials'. Lacrimal Gland, Tear Film, and Dry Eye Syndromes 3 Part B", Adv Exp Med Biol, 2002; 506:1079-86).

(Continued)

Primary Examiner — Nyeemah A Grazier
(74) Attorney, Agent, or Firm — Fish & Richardson P.C.

(57) ABSTRACT

This invention relates to sustained release dosage forms comprising {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or a pharmaceutically acceptable salt thereof, and doses and methods related thereto.

31 Claims, 11 Drawing Sheets

(56) References Cited

U.S. PATENT DOCUMENTS

| | | |
|---|---|---|
| 8,486,902 B2 | 7/2013 | Rodgers et al. |
| 8,513,270 B2 | 8/2013 | Arvanitis et al. |
| 8,530,485 B2 | 9/2013 | Rodgers et al. |
| 8,541,425 B2 | 9/2013 | Rodgers et al. |
| 8,563,541 B2 | 10/2013 | Arvanitis et al. |
| 8,604,043 B2 | 12/2013 | Li et al. |
| 8,691,807 B2 | 4/2014 | Yao et al. |
| 8,716,303 B2 | 5/2014 | Rodgers et al. |
| 8,722,693 B2 | 5/2014 | Rodgers et al. |
| 8,741,895 B2 | 6/2014 | Rodgers et al. |
| 8,748,401 B2 | 6/2014 | Rodgers et al. |
| 8,765,734 B2 * | 7/2014 | Huang ................ C07D 401/14 514/210.21 |
| 8,822,481 B1 | 9/2014 | Rodgers et al. |
| 8,829,013 B1 | 9/2014 | Rodgers et al. |
| 8,835,423 B2 | 9/2014 | Arvanitis et al. |
| 8,841,318 B2 | 9/2014 | Arvanitis et al. |
| 8,883,806 B2 | 11/2014 | Zhou et al. |
| 8,889,697 B2 | 11/2014 | Rodgers et al. |
| 8,933,085 B2 | 1/2015 | Rodgers et al. |
| 8,933,086 B2 | 1/2015 | Rodgers et al. |
| 8,946,245 B2 | 2/2015 | Rodgers et al. |
| 8,987,442 B2 | 3/2015 | Tung et al. |
| 8,987,443 B2 * | 3/2015 | Liu .................... C07D 487/04 544/280 |
| 8,993,582 B2 | 3/2015 | Zhou et al. |
| 9,000,161 B2 | 4/2015 | Zhou et al. |
| 9,023,840 B2 | 5/2015 | Yao et al. |
| 9,034,884 B2 | 5/2015 | Rodgers et al. |
| 9,079,912 B2 | 7/2015 | Rodgers et al. |
| 9,090,611 B2 | 7/2015 | Rodgers et al. |
| 2002/0111353 A1 | 8/2002 | Ledeboer et al. |
| 2003/0064969 A1 | 4/2003 | Bhagwat et al. |
| 2003/0100756 A1 | 5/2003 | Adams et al. |
| 2003/0144309 A1 | 7/2003 | Choon-Moon |
| 2003/0165576 A1 | 9/2003 | Fujii et al. |
| 2004/0009222 A1 | 1/2004 | Chou et al. |
| 2004/0009983 A1 | 1/2004 | Cox et al. |
| 2004/0029857 A1 | 2/2004 | Hale et al. |
| 2004/0077654 A1 | 4/2004 | Bouillot |
| 2004/0198737 A1 | 10/2004 | Cox et al. |
| 2004/0204404 A1 | 10/2004 | Zelle |
| 2004/0214928 A1 | 10/2004 | Aronov |
| 2004/0235862 A1 | 11/2004 | Burns |
| 2005/0014966 A1 | 1/2005 | Tabe |
| 2005/0054568 A1 | 3/2005 | Ling |
| 2005/0153989 A1 | 7/2005 | Grotzfeld et al. |
| 2006/0004010 A1 | 1/2006 | Habashita et al. |
| 2006/0020011 A1 | 1/2006 | Wu et al. |
| 2006/0079511 A1 | 4/2006 | Liu et al. |
| 2006/0106020 A1 | 5/2006 | Rodgers et al. |
| 2006/0106027 A1 | 5/2006 | Furet et al. |
| 2006/0128803 A1 | 6/2006 | Klimko |
| 2006/0135537 A1 | 6/2006 | Knegtel et al. |
| 2006/0178393 A1 | 8/2006 | Pitts |
| 2006/0183761 A1 | 8/2006 | Ledeboer et al. |
| 2006/0183906 A1 | 8/2006 | Rodgers et al. |
| 2006/0223864 A1 | 10/2006 | Biju |
| 2006/0293311 A1 | 12/2006 | Li et al. |
| 2007/0135461 A1 | 6/2007 | Rodgers et al. |
| 2007/0135466 A1 | 6/2007 | Ledeboer et al. |
| 2007/0149506 A1 | 6/2007 | Arvanitis et al. |
| 2007/0149561 A1 | 6/2007 | Dhanak et al. |
| 2007/0191364 A1 | 8/2007 | Braun et al. |
| 2007/0191405 A1 | 8/2007 | Noronha |
| 2007/0208053 A1 | 9/2007 | Wang et al. |
| 2007/0259904 A1 | 11/2007 | Noronha |
| 2008/0021026 A1 | 1/2008 | Borchardt et al. |
| 2008/0085898 A1 | 4/2008 | Lu |
| 2008/0096852 A1 | 4/2008 | Yanni |
| 2008/0119496 A1 | 5/2008 | Ohlmeyer |
| 2008/0161346 A1 | 7/2008 | Cheng |
| 2008/0188500 A1 | 8/2008 | Arvanitis et al. |
| 2008/0194468 A1 | 8/2008 | Bodor |
| 2008/0207570 A1 | 8/2008 | Segura-Orsoni |
| 2008/0207584 A1 | 8/2008 | Habashita et al. |
| 2008/0280876 A1 | 11/2008 | Hobson et al. |
| 2008/0312258 A1 | 12/2008 | Rodgers et al. |
| 2008/0312259 A1 | 12/2008 | Rodgers et al. |
| 2009/0018156 A1 | 1/2009 | Tang et al. |
| 2009/0076070 A1 | 3/2009 | Harada et al. |
| 2009/0088445 A1 | 4/2009 | Ledeboer et al. |
| 2009/0131403 A1 | 5/2009 | Kusuda |
| 2009/0181959 A1 | 7/2009 | Rodgers et al. |
| 2009/0197869 A1 | 8/2009 | Arvanitis et al. |
| 2009/0203637 A1 | 8/2009 | Hocek et al. |
| 2009/0215766 A1 | 8/2009 | Rodgers et al. |
| 2009/0221608 A1 | 9/2009 | Cui et al. |
| 2009/0233903 A1 | 9/2009 | Rodgers et al. |
| 2009/0318405 A1 | 12/2009 | Li et al. |
| 2010/0022522 A1 | 1/2010 | Rodgers et al. |
| 2010/0069381 A1 | 3/2010 | Itoh et al. |
| 2010/0113416 A1 * | 5/2010 | Friedman ............ A61K 31/519 514/210.21 |
| 2010/0190981 A1 | 7/2010 | Zhou et al. |
| 2010/0210627 A1 | 8/2010 | Mao et al. |
| 2010/0298334 A1 | 11/2010 | Rodgers et al. |
| 2010/0298355 A1 | 11/2010 | Li et al. |
| 2011/0059951 A1 | 3/2011 | Rodgers et al. |
| 2011/0082159 A1 | 4/2011 | Rodgers et al. |
| 2011/0086810 A1 | 4/2011 | Rodgers et al. |
| 2011/0086835 A1 | 4/2011 | Rodgers et al. |
| 2011/0201593 A1 | 8/2011 | Babu et al. |
| 2011/0207754 A1 | 8/2011 | Li et al. |
| 2011/0223210 A1 | 9/2011 | Rodgers et al. |
| 2011/0224157 A1 | 9/2011 | Rodgers et al. |
| 2011/0224190 A1 * | 9/2011 | Huang ................ C07D 401/14 514/210.21 |
| 2011/0288107 A1 | 11/2011 | Parikh et al. |
| 2012/0014989 A1 | 1/2012 | Rodgers |
| 2012/0077798 A1 | 3/2012 | Rodgers et al. |
| 2012/0149681 A1 | 6/2012 | Rodgers |
| 2012/0149682 A1 | 6/2012 | Rodgers et al. |
| 2012/0214825 A1 | 8/2012 | Vannucchi et al. |
| 2012/0225057 A1 * | 9/2012 | Flynn .................. C07D 401/12 424/133.1 |
| 2012/0252779 A1 * | 10/2012 | Ramsden ............ C07D 487/04 514/210.21 |
| 2012/0301464 A1 * | 11/2012 | Friedman ............ A61K 31/519 424/133.1 |
| 2012/0329782 A1 | 12/2012 | Arvanitis et al. |
| 2013/0018034 A1 | 1/2013 | Yao et al. |
| 2013/0040973 A1 | 2/2013 | Vannucchi et al. |
| 2013/0045963 A1 | 2/2013 | Rodgers et al. |
| 2013/0060026 A1 * | 3/2013 | Zhou .................. C07D 491/10 544/229 |
| 2013/0137681 A1 | 5/2013 | Rodgers et al. |
| 2013/0225556 A1 | 8/2013 | Rodgers et al. |
| 2013/0253190 A1 | 9/2013 | Zhou |
| 2013/0253191 A1 | 9/2013 | Zhou |
| 2013/0253193 A1 | 9/2013 | Zhou |
| 2013/0274257 A1 | 10/2013 | Arvanitis et al. |
| 2013/0296299 A1 | 11/2013 | Rodgers et al. |
| 2014/0005166 A1 | 1/2014 | Rodgers et al. |
| 2014/0005210 A1 | 1/2014 | Rodgers et al. |
| 2014/0018374 A1 | 1/2014 | Rodgers et al. |
| 2014/0031344 A1 | 1/2014 | Arvanitis et al. |
| 2014/0073657 A1 | 3/2014 | Li et al. |
| 2014/0094477 A1 | 4/2014 | Rodgers et al. |
| 2014/0121198 A1 | 5/2014 | Li et al. |
| 2014/0135350 A1 | 5/2014 | Ni et al. |
| 2014/0171409 A1 | 6/2014 | Yao et al. |
| 2014/0221379 A1 | 8/2014 | Rodgers et al. |
| 2014/0228346 A1 | 8/2014 | Rodgers et al. |
| 2014/0243360 A1 | 8/2014 | Rodgers et al. |
| 2014/0256941 A1 | 9/2014 | Liu et al. |
| 2014/0275031 A1 * | 9/2014 | Huang ................ C07D 401/14 514/210.21 |
| 2014/0303196 A1 | 10/2014 | Rodgers et al. |
| 2014/0343030 A1 | 11/2014 | Li et al. |
| 2015/0065447 A1 * | 3/2015 | Sandor ................ C07D 495/14 514/49 |
| 2015/0065484 A1 | 3/2015 | Yeleswaram et al. |

(56) References Cited

U.S. PATENT DOCUMENTS

| | | | |
|---|---|---|---|
| 2015/0087632 A1 | 3/2015 | Rodgers et al. | |
| 2015/0087662 A1 | 3/2015 | Li et al. | |
| 2015/0152117 A1* | 6/2015 | Gibbons | C07D 487/04 514/210.18 |
| 2015/0164900 A1 | 6/2015 | Rodgers et al. | |
| 2015/0225412 A1* | 8/2015 | Brameld | C07D 401/14 514/210.18 |

FOREIGN PATENT DOCUMENTS

| | | |
|---|---|---|
| EP | 0587473 | 3/1994 |
| EP | 0727217 | 8/1996 |
| EP | 0795556 | 9/1997 |
| EP | 1104764 | 6/2001 |
| JP | 07-010876 | 1/1995 |
| JP | 2003/155285 | 5/2003 |
| JP | 2006/518341 | 8/2006 |
| WO | WO 96/30343 | 10/1996 |
| WO | WO 97/02262 | 1/1997 |
| WO | WO 97/02266 | 1/1997 |
| WO | WO 97/36587 | 10/1997 |
| WO | WO 97/38664 | 10/1997 |
| WO | WO 97/45412 | 12/1997 |
| WO | WO 98/44797 | 10/1998 |
| WO | WO 98/51391 | 11/1998 |
| WO | WO 99/00654 | 1/1999 |
| WO | WO 99/62908 | 12/1999 |
| WO | WO 99/65908 | 12/1999 |
| WO | WO 99/65909 | 12/1999 |
| WO | WO 00/09495 | 2/2000 |
| WO | WO 00/51614 | 9/2000 |
| WO | WO 00/53595 | 9/2000 |
| WO | WO 00/63168 | 10/2000 |
| WO | WO 01/14402 | 3/2001 |
| WO | WO 01/27104 | 4/2001 |
| WO | WO 01/42246 | 6/2001 |
| WO | WO 01/64655 | 9/2001 |
| WO | WO 01/81345 | 11/2001 |
| WO | WO 01/98344 | 12/2001 |
| WO | WO 02/00196 | 1/2002 |
| WO | WO 02/00661 | 1/2002 |
| WO | WO 02/16370 | 2/2002 |
| WO | WO 02/46184 | 6/2002 |
| WO | WO 02/055084 | 7/2002 |
| WO | WO 02/055496 | 7/2002 |
| WO | WO 02/060492 | 8/2002 |
| WO | WO 02/080926 | 10/2002 |
| WO | WO 02/092573 | 11/2002 |
| WO | WO 02/096909 | 12/2002 |
| WO | WO 03/000695 | 1/2003 |
| WO | WO 03/011285 | 2/2003 |
| WO | WO 03/024967 | 3/2003 |
| WO | WO 03/037347 | 5/2003 |
| WO | WO 03/048162 | 6/2003 |
| WO | WO 03/092595 | 11/2003 |
| WO | WO 03/099771 | 12/2003 |
| WO | WO 03/099796 | 12/2003 |
| WO | WO 2004/003026 | 1/2004 |
| WO | WO 2004/005281 | 1/2004 |
| WO | WO 2004/005282 | 1/2004 |
| WO | WO 2004/026406 | 4/2004 |
| WO | WO 2004/041814 | 5/2004 |
| WO | WO 2004/046120 | 6/2004 |
| WO | WO 2004/047843 | 6/2004 |
| WO | WO 2004/056786 | 7/2004 |
| WO | WO 2004/072063 | 8/2004 |
| WO | WO 2004/080980 | 9/2004 |
| WO | WO 2004/092154 | 10/2004 |
| WO | WO 2004/099204 | 11/2004 |
| WO | WO 2004/099205 | 11/2004 |
| WO | WO 2005/005988 | 1/2005 |
| WO | WO 2005/013986 | 2/2005 |
| WO | WO 2005/020921 | 3/2005 |
| WO | WO 2005/026129 | 3/2005 |
| WO | WO 2005/028444 | 3/2005 |
| WO | WO 2005/049033 | 6/2005 |
| WO | WO 2005/051393 | 6/2005 |
| WO | WO 2005/060972 | 7/2005 |
| WO | WO 2005/061463 | 7/2005 |
| WO | WO 2005/062795 | 7/2005 |
| WO | WO 2005/089502 | 9/2005 |
| WO | WO 2005/095400 | 10/2005 |
| WO | WO 2005/105146 | 11/2005 |
| WO | WO 2005/105814 | 11/2005 |
| WO | WO 2005/105988 | 11/2005 |
| WO | WO 2005/110410 | 11/2005 |
| WO | WO 2005/117909 | 12/2005 |
| WO | WO 2005/121130 | 12/2005 |
| WO | WO 2005/123719 | 12/2005 |
| WO | WO 2006/004984 | 1/2006 |
| WO | WO 2006/013114 | 2/2006 |
| WO | WO 2006/022459 | 3/2006 |
| WO | WO 2006/039718 | 4/2006 |
| WO | WO 2006/046023 | 5/2006 |
| WO | WO 2006/046024 | 5/2006 |
| WO | WO 2006/052913 | 5/2006 |
| WO | WO 2006/056399 | 6/2006 |
| WO | WO 2006/067445 | 6/2006 |
| WO | WO 2006/069080 | 6/2006 |
| WO | WO 2006/077499 | 7/2006 |
| WO | WO 2006/096270 | 9/2006 |
| WO | WO 2006/101783 | 9/2006 |
| WO | WO 2006/108103 | 10/2006 |
| WO | WO 2006/122806 | 11/2006 |
| WO | WO 2006/127587 | 11/2006 |
| WO | WO 2006/129199 | 12/2006 |
| WO | WO 2006/136823 | 12/2006 |
| WO | WO 2007/002433 | 1/2007 |
| WO | WO 2007/025090 | 3/2007 |
| WO | WO 2007/041130 | 4/2007 |
| WO | WO 2007/043677 | 4/2007 |
| WO | WO 2007/044894 | 4/2007 |
| WO | WO 2007/049041 | 5/2007 |
| WO | WO 2007/062459 | 6/2007 |
| WO | WO 2007/070514 | 6/2007 |
| WO | WO 2007/076423 | 7/2007 |
| WO | WO 2007/077949 | 7/2007 |
| WO | WO 2007/084557 | 7/2007 |
| WO | WO 2007/090141 | 8/2007 |
| WO | WO 2007/090748 | 8/2007 |
| WO | WO 2007/116313 | 10/2007 |
| WO | WO 2007/117494 | 10/2007 |
| WO | WO 2007/129195 | 11/2007 |
| WO | WO 2007/135461 | 11/2007 |
| WO | WO 2007/140222 | 12/2007 |
| WO | WO 2008/013925 | 1/2008 |
| WO | WO 2008/028937 | 3/2008 |
| WO | WO 2008/035376 | 3/2008 |
| WO | WO 2008/043031 | 4/2008 |
| WO | WO 2008/058126 | 5/2008 |
| WO | WO 2008/064157 | 5/2008 |
| WO | WO 2008/067119 | 6/2008 |
| WO | WO 2008/077712 | 7/2008 |
| WO | WO 2008/079291 | 7/2008 |
| WO | WO 2008/079292 | 7/2008 |
| WO | WO 2008/082198 | 7/2008 |
| WO | WO 2008/082839 | 7/2008 |
| WO | WO 2008/082840 | 7/2008 |
| WO | WO 2008/106692 | 9/2008 |
| WO | WO 2008/124323 | 10/2008 |
| WO | WO 2008/139161 | 11/2008 |
| WO | WO 2008/145681 | 12/2008 |
| WO | WO 2008/145688 | 12/2008 |
| WO | WO 2008/157207 | 12/2008 |
| WO | WO 2008/157208 | 12/2008 |
| WO | WO 2009/007839 | 1/2009 |
| WO | WO 2009/016460 | 2/2009 |
| WO | WO 2009/049028 | 4/2009 |
| WO | WO 2009/064486 | 5/2009 |
| WO | WO 2009/064835 | 5/2009 |
| WO | WO 2009/071577 | 6/2009 |
| WO | WO 2009/100130 | 8/2009 |
| WO | WO 2009/109576 | 9/2009 |

(56) References Cited

FOREIGN PATENT DOCUMENTS

| | | |
|---|---|---|
| WO | WO 2009/114512 | 9/2009 |
| WO | WO 2009/115572 | 9/2009 |
| WO | WO 2009/155156 | 12/2009 |
| WO | WO 2009/158687 | 12/2009 |
| WO | WO 2010/000978 | 1/2010 |
| WO | WO 2010/001169 | 1/2010 |
| WO | WO 2010/020905 | 2/2010 |
| WO | WO 2010/022076 | 2/2010 |
| WO | WO 2010/022081 | 2/2010 |
| WO | WO 2010/026121 | 3/2010 |
| WO | WO 2010/026122 | 3/2010 |
| WO | WO 2010/026124 | 3/2010 |
| WO | WO 2010/039939 | 4/2010 |
| WO | WO 2010/081692 | 7/2010 |
| WO | WO 2010/083283 | 7/2010 |
| WO | WO 2010/135621 | 11/2010 |
| WO | WO 2010/135650 | 11/2010 |
| WO | WO 2011/003418 | 1/2011 |
| WO | WO 2011/025685 | 3/2011 |
| WO | WO 2011/028685 | 3/2011 |
| WO | WO 2011/029802 | 3/2011 |
| WO | WO 2011/031554 | 3/2011 |
| WO | WO 2011/035900 | 3/2011 |
| WO | WO 2011/044481 | 4/2011 |
| WO | WO 2011/057784 | 5/2011 |
| WO | WO 2011/066369 | 6/2011 |
| WO | WO 2011/069141 | 6/2011 |
| WO | WO 2011/112662 | 9/2011 |
| WO | WO 2011/130146 | 10/2011 |
| WO | WO 2011/144338 | 11/2011 |
| WO | WO 2011/146808 | 11/2011 |
| WO | WO 2012/003457 | 1/2012 |
| WO | WO 2012/045010 | 4/2012 |
| WO | WO 2012/068440 | 5/2012 |
| WO | WO 2012/068450 | 5/2012 |
| WO | WO 2012/177606 | 12/2012 |
| WO | WO 2013/007765 | 1/2013 |
| WO | WO 2013/007768 | 1/2013 |
| WO | WO 2013/023119 | 2/2013 |
| WO | WO 2013/026025 | 2/2013 |
| WO | WO 2013/036611 | 3/2013 |
| WO | WO 2013/173720 | 11/2013 |
| WO | WO 2014/071031 | 5/2014 |
| WO | WO 2014/138168 | 9/2014 |

OTHER PUBLICATIONS

Abstract of Chilean patent application No. 3496-06 published in Official Gazette of the Republic of Chile (Jun. 1, 2007) and publication (2 pages).
Aho, T. et al., Expression of human pim family genes is selectively up-regulated by cytokines promoting T helper type 1, but not T helper type 2, cell differentiation, Immunology 116: 82-88, 2005.
Albach et al., "Diagnosis of keratoconjunctivitis sicca in rheumatoid arthritis. The value of various tests", Ophthalmologe, Apr. 1994; 91(2):229-34—in German (with English abstract/summary contained therein).
Anderson et al., "Biochemical characterization of GSK1070916, a potent and selective inhibitor of Aurora B and Aurora C kinases with an extremely long residence time", Biochem. J., 420(2), 259-265 (2009).
Bachmann, et al., "The serine/threonine kinease Pim-1," The International Journal of Biochechemistry and Cell Biology 37: 726-730 (2005).
Banker, et al., "Modern Pharmaceuticals" p. 596 (1996).
Barabino et al., "Tear film and ocular surface tests in animal models of dry eye; uses and limitations", Experimental Eye Research, 2004, 79, 613-621.
Barr et al., "Corneal scarring in the Collaborative Longitudinal Evaluation of Keratoconus (CLEK) Study: baseline prevalence and repeatability of detection", Cornea, 1999; 18(1):34-46.
Baudouin et al., "Flow cytometry in impression cytology specimens. A new method for evaluation of conjunctival Inflammation", Invest Ophthalmol Vis Sci, 1997; 38:1458-1464.

Baytel et al., "The human Pim-2 proto-oncogene and its testicular expression" Biochimica et Biophysica Acta 1442: 274-285, (1998).
Baxter et al., "Reductive Aminations of Carbonyl Compounds with Borohydride and Borane Reducing Agents," Organic Reactions, 2002, 1-57.
Beck et al., "Brief Report: Alleviation of Systemic Manifestations of Castleman's Disease by Monoclonal Anti-Interleukin-6 Antibody," N. Engl. J. Med., 1994, 330(9):602-605.
Begley, et al., "Use of the dry eye questionnaire to measure symptoms of ocular irritation in patients with aqueous tear deficient dry eye", Cornea, 2002:21:664-70.
Bell, Malcolm, and Zalay, Andrew, "Synthesis of Substituted 3-Amino [6, 5-b] triazinoindoles." Journal of Heterocyclic Chemistry, 12(5):1001-1004, Oct. 1975.
Bennett et al., "Proposals for the classification of the myelodysplastic syndromes," British Journal of Haematology, 1982, 51: 189-199.
Berge, et al., "Pharmaceutical salts", J. Pharma. Science (1977) vol. 66(1) pp. 1-19.
Beyer, "Uber die Synthese von 2-Methylmercapto-1.3.4-thiodiazinen und deren Umlagerung in Pyrazolderivate (The synthesis of 2-methylthio-1,3,4-thiadiazines and their rearrangement to pyrazole derivatives)", Chem. Berichte Jahrg., 92:2593-2599 (1959) (abstract provided).
Bhattacharya et al., "Brittain, ed. Polymorphism in Pharmaceutical Solids," 2009, p. 327-345.
Bhovi, et al., "1,3-Dipolar Cycloaddition Reaction: Synthesis and Antimicrobial, Activity of Some New 3-Ethoxycarbonyl-s-Methoxy-6-Bromo-2-Triazolylmethylindoles", Indian Journal of Heterocyclic Chemistry, vol. 14, (Jul.-Sep. 2004), pp. 15-18.
Bioreversible Carriers in Drug Design, ed. Edward B. Roche, American Pharmaceutical Association and Pergamon Press, 1987.
Blume-Jensen, et al, "Oncogenic kinase signaling", Nature 2001, 411(6835):355-365.
Bock, C., et al. "Managing drug resistance in cancer: lessons from HIV therapy." Nature. (Jul. 2012), vol. 12, pp. 494-501.
Bolen, "Nonreceptor tyrosine protein kinases", Oncogene, 1993, 8(8):2025-31.
Bollrath et al., "gp130-Mediated Stat3 Activation in Enterocytes Regulates Cell Survival and Cell-Cycle Progression during Colitis-Associated Tumorigenesis," Cancer Cell, 15:91-102 (2009).
Borie, et al., "Combined Use of the Jak3 Inhibitor CP-690, 550 with Mycophenolate Mofetil to Prevent Kidney Allograft Rejection in Nonhuman Primates", Transplantation, Dec. 27, 2005;80(12):1756-64.
Bosworth, "JAK1/JAK2 Inhibitor Ruxolitinib Is a Rising Start," Clinical Oncology, Apr. 2011, vol. 06:04, 3 pages.
Boudny, et al., "JAK/STAT signaling pathways and cancer", Neoplasm, 49:349-355, 2002.
Bourcier et al., "Expression of CD40 and CD40 ligand in the human conjunctival epithelium", Invest Ophthalmol Vis Sci, 2000;41:120-126.
Bowman, et al. "STATs in oncogenesis", Oncogene, 19:2474-2488, 2000.
Brett et al., "Structural chemistry of polycyclic heteroaromatic compound. Part 4. Electronic structures of angular dithienopyridines," J Chem Soc, Perkin Trans 2, Jan. 1, 1994, 9:2045.
Brignole et al., "Expression of Fas-Fas Ligand Antigens and Apoptotic Marker APO2-7 by the Human Conjunctival Epithelium. Positive correlation with class II HLA DR expression in inflammatory Ocular Surface Disorders", Exp Eye Res, 1998;67:687-697.
Brignole et al., "Flow cytometric analysis of inflammatory markers in conjunctival epithelial cells of patients with dry eyes", Invest Ophthalmol Vis Sci, 2000; 41:1356-1363.
Brignole et al., "Flow cytometric analysis of inflammatory markers in KCS: 6-month treatment with topical cyclosporin A", Invest Ophthalmol Vis Sci, 2001; 42:90-95.
Brignole et al., "Flow cytometly in conjunctival impression cytology: a new tool for exploring ocular surface pathologies", Exp Eye Res, 2004;78:473-481.
Bromberg et al., "Inflammation and Cancer: IL-6 and STAT3 Complete the Link," Cancer Cell, 15:79-80 (2009).

(56) References Cited

OTHER PUBLICATIONS

Bron, et al., "Grading of corneal and conjunctival staining in the context of other dry eye tests", Cornea, 2003;22(7):640-50.
Bron, et al., "Methodologies to Diagnose and Monitor Dry Eye Disease: Report of the Diagnostic Methodology Subcommittee of the International Dry Eye Workshop (2007)", The Ocular Surface, 5(2), 108-152 (Apr. 2007).
Bunning and Germing, "Myelodysplastic syndromes/neoplasms" in Chapter 5, Swerdlow, et al, eds. WHO Classification of Tumours of Haematopoietic and Lymphoid Tissues. (ed. 4th edition): Lyon, France: IARC Press;2008:88-103.
Burger et al., "Janus kinase inhibitor INCB20 has antiproliferative and apoptotic effects on human myeloma cells in vitro and in vivo", Mol. Cancer Ther. 2009:8(1), Jan. 2009 pp. 26-35.
Burger, et al., "Gp130 and ras mediated signaling in human plasma cell line IN/a-6: a cytokine-regulated tumor model for plasmacytoma", Hematol J., 2:42-53, 2001.
Campas-Moya, C., "Ruxolitinib. Tyrosine-protein kinase JAK1/2 inhibitor, treatment of myelofibrosis, treatment of myeloproliferative neoplasms, treatment of psoriasis", Drugs of the Future, (Jun. 2010) vol. 35, No. 6, pp. 457-465.
Candotti, et al. (2002). "Molecular aspects of primary immunodeficiencies: lessons from cytokine and other signaling pathways.", J Clin Invest, 109(10): 1261-9.
Candotti, F., et al. (1997). "Structural and functional basis for JAK3-deficient severe combined immunodeficiency.", Blood, 90(10): 3996-4003.
Carey and Sundberg, Advanced Organic Chemistry, Part B: Reactions and Synthesis, 4th ed., Kluwer Academic/Plenum Publishers:New York, pp. 111-119 (2001).
Carey and Sundberg, Advanced Organic Chemistry, Part B: Reactions and Synthesis, Oxidations, 4th ed., Kluwer Academic/Plenum Publishers:New York, pp. 747-757 (2001).
Cermak, et al, "Is complete androgen insensitivity syndrome associated with alterations in the meibomium gland and ocular surface", Cornea, 2003;22:516-521.
Cetkovic-Cvrlje, et al. (2003). "Targeting JAK3 with JANEX-1 for prevention of autoimmune type 1 diabetes in NOD mice.", Clin Immunol, 106(3): 213-25.
Chalandon, "Targeting mutated protein tyrosine kinases and their signaling pathways in hematologic malignancies", Haematologica, 90 (7):949-68 (2005).
Changelian, et al., "Prevention of Organ Allograft Rejection by a Specific Janus Kinase 3 Inhibitor", Science, 2003, 302, 875-878.
Chari et al., "Complete Remission Achieved with Single Agent CNTO 328, an Anti-IL-6 Monoclonal Antibody, in Relapsed and Refractory Myeloma," *Clinical Lymphoma, Myeloma & Leukemia*, 2013, 13(3):333-337
Chauhan, et al, "Autoimmunity in Dry Eye due to resistance of Th17 to Treg Suppression", J. Immunology, 182(3):1247-52 (2009).
Chauhan et al., "A concise review on sustained drug delivery system and its opportunities," International Journal on Pharmtech Research, Mar. 2012, 2: 227-238.
Chemical encyclopedia, vol. 1, pp. 242-243, publication "Soviet Encyclopedia," Moscow, 1988.
Chen et al., "Induction of myelodysplasia by myeloid-derived suppressor cells," J Clin Invest, Nov. 2013, 123(11): 4595-611.
Chen et al., *Blood*, 2009, 114(4): 891-900.
Chen, et al., "Stat3 Activation in Human Endometrial and Cervical Cancer", British Journal of Cancer, 96, 591-599, 2007.
Cheson et al., "Report of an international working group to standardize response criteria for myelodysplastic syndromes," Blood, Dec. 2000, 96(12): 3671-4.
Chew, et al., "An instrument for quantifying meibomian lipid on the lid margin: the Meibometer", Curr Eye Res, 1993a;12:247-254.
Chew, et al., "The casual level of meibomian lipids in humans", Current Eye Research, 1993b;12:255-259.
Cho, et al, "Review of the tear break-up time and a closer look at the tear break-up time of Hong Kong Chinese", Optom Vis Sci, 1993;70(1):30-8.

Choi Ha-Soon, et al., "Design and synthesis of 7H-pyrrolo[2,3-d]pyrimidines as focal adhesion inhibitors. Part 1", Bioorg. & Med. Chem. Lett., 16(8):2173-2176 (2006).
Choy et al., "Therapeutic Benefit of Blocking Interleukin-6 Activity With an Anti-Interleukin-6 Receptor Monoclonal Antibody in Rheumatoid Arthritis," Arthritis & Rheumatism, 2002, 46(12) 3143-3150.
Chu-Moyer, et al., "Preparation of the Four Regioisomeric 2-(Methylthio)oxazolopyridines: Useful Synthons for Elaboration to 2-(Amino substituted)oxazolopyridines", J. Org. Chem. 60(17): 5721-5725 (1995).
Cilloni et al., "Emerging drugs for chronic myeloid leukemia", Expert Opinion on Emerging Drugs, (Jun. 2010) vol. 15, No. 2, pp. 175-184.
Claessens et al., "In vitro proliferation and differentitation of erythyroid progenitors from patients with myelodysplastic syndromes: evidence for Fas-dependent apoptosis," Blood, Mar. 2012, 1594-1601.
Clark et al., "Discovery and Development of Janus Kinase (JAK) inhibitors for Inflammatory Diseases," J Med Chem., 2014, pp. A-P.
Claridge; Bioorganic and Medicinal Chemistry Letters, 2008, 18,2793-2798P.
Coligan, J. E. et al, Wiley Press; Methods in Molecular Biology: vol. 225, Inflammation Protocols., Winyard, P.G. and Willoughby, D.A., Humana Press (2003).
Communication dated Jan. 22, 2009 for European Appln. No. 06839328.9 (5 pgs.).
Conklyn, M. et al., "The JAK3 inhibitor CP0690550 selectively reduces NK and CD8+ cell numbers in cynomolgus monkey blood following chronic oral dosing", Journal of Leukocyte Biology, 2004, 76, 1248-1255.
Costa Rican Office Action in CR Application No. 10065, dated Jul. 16, 2013, 8 pages.
Cottet and Schlosser, "Three Chloro(trifluoromethyl)pyridines as Model Substrates for Regioexhaustive Functionalization," Eur J Org Chem, 2004, 18:3793-3798.
Craig et al. "Tear lipid layer structure and stability following expression of the meibomian glands.", Ophthalmic Physiol Opt, 1995, 15(6):569-74.
Current Protocols in Immunology, vol. 3., Coligan, J.E. et al, Wiley Press (1988).
Daniels et al., "Imatinib mesylate inhibits the profibrogenic activity of TGF-? and prevents bleomycinmediated lung fibrosis." J. Clin. Invest., 114(9):1308-1316, Nov. 2004.
Danjo et al., "Observation of precorneal tear film in patients with Sjogren's syndrome", Acta Ophthalmol Scand, 73:501-505 (1995).
De Paiva, et al, "IL-17 disrupts corneal barrier following desiccating stress", Mucosal Immunol. 2(3):243-53 (2009).
De Vos, J., et al. (2000). "JAK2 tyrosine kinase inhibitor tyrphostin AG490 downregulates the mitogen-activated protein kinase (MAPK) and signal transducer and activator of transcription (STAT) pathways and induces apoptosis in myeloma cells.", Br J Haematol, 109(4): 823-8.
Deng Jun, et al, "Rh-catalyzed asymmetric hydrogenation of gamma-phthalimido-substituted esters: an efficient enantioselective synthesis of beta-aryl-gamma-amino acids", Org. Lett. 9(23):4825-4827 (2007).
Deuse, T. et al., "Novel Immunosuppression: R348, a JAK3- and Syk-Inhibitor Attenuates Acute Cardiac Allograft Rejection", Transplantation, 2008, 85(6) 885-892.
Doane, "An instrument for in vivo tear film interferometry", Optom Vis Sci, 1989; 66: 383-8.
Doleschall G., et al., "Thermal and Acid Catalysed Degradations of 3-alkylthio-6,7-dihydro[1.2.4]triazino[1,6-c]quinazolin-5-ium-1-olates", Tetrahedron, 30:3997-4012, 1974.
Dorwald; "Side Reactions in Organic Synthesis: A Guide to Successful Synthesis Design" 2005 Wiley-VCH Verlag GmbH & Co. KGaA, Wienheim, chapter 1, 32 pages.
Dudley, A.C., et al. "AVEGF/JAK2/STAT5 axis may partially mediate endothelial cell tolerance to hypoxia", Biochem. J. 2005, 390(Pt 2):427-36.
Eghtedar, "Phase II Study of the JAK2 Inhibitor, INCB018424, in Patients with Refractory Leukemias Including Post-Myeloprolifera-

(56) References Cited

OTHER PUBLICATIONS tive Disorder Acute Myeloid Leukemia", American Society of Hematology (ASH) annual meeting in Orlando, FL (Dec. 6, 2010), Abstract/poster 509.
Einmahl, et al., "Therapeutic applications of viscous and injectable poly(ortho esters)", Adv. Drug. Deliv. Rev. 53:45-73 (2001).
Eliason, et al., "Staining of the conjunctiva and conjunctival tear film", Br J Ophthalmol, 1990;74:519-22.
Expert Scientific Group on Phase One Clinical Trials Final Report Nov. 30, 2006, pp. C1, C35-C38.
Fabrizio Saettone, "Ocular inserts for topical delivery", Advanced Drug Delivery Reviews 16:95-106 (1998).
Farrell et al., "A classification for dry eyes following comparison of tear thinning time with Schirmer tear test", Acta Ophthalmol (Copenh), 1992; 70(3):357-60.
Farrell et al., "A clinical procedure to predict the value of temporary occlusion therapy in keratoconjunctivitis sicca" Ophthal Physiol Opt, 2003;23:1-8.
Farris, "Tear osmolarity—a new gold standard?" Adv Exp Med Biol, 350:495-503, 1994.
Fayad et al., "Interleukin-6 and interleukin-10 levels in chronic lymphocytic leukemia. correlation with phenotypic characteristics and outcome," Blood, Jan. 2001, 97(1): 256-263.
Fenaux et al., "A randomized phase 3 study of lenalidomide versus placebo in RBC transfusion-dependent patients with Low-/Intermediate-1-risk myelodysplastic syndromes with del5q," Blood, Oct. 2011, 118(14): 3765-76.
Fenaux, et al., "Efficacy of azacitidine compared with that of conventional care regimens in the treatment of higher-risk myelodysplastic syndromes: a randomised, open-label, phase III study," Lancet Oncol, Mar. 2009, 10: 223-32.
Fiskus, W. et al., "Synergistic Activity of Combinations of JAK2 Kinase Inhibitor with PI3K/mTOR, MEK or PIM Kinase Inhibitor Against Human Myeloproliferative Neoplasm Cells Expressing JAK2V617F" J. American Chem. Soc., 52nd Annual Meeting of the American-Society-of-Hematology (ASH); Orlando, FL, USA; Dec. 4-7, 2010, ACS Publications; vol. 116, No. 21 Nov. 1, 2010 p. 349, XP002667216, ISSN: 0002-7863 (1 page).
Flex E., et al., "Somatically acquired JAK1 mutations in adult acute lymphoblastic leukemia", J. Exp Med. 205:751-8, (2008).
Fonesca, J.E. et al., "Interleukin-6 as a key player in systemic inflammation and joint destruction", Autoimmunity Reviews, 8:538-42, (2009).
Fridman, et al., "Preclinical evaluation of local JAK1 and JAK2 inhibition in cutaneous inflammation", Journal of Investigative Dermatology, (Sep. 2011) vol. 131, No. 9, pp. 1838-1844.
Fridman, J. et al. "Selective JAK Inhibition is Efficacious against Multiple Myeloma Cells and Reverses the Protective Effects of Cytokine and Stromal Cell Support" Abstract #0956, presented Sunday, Jun. 15, 2008 at the European Hematology Association, 13th Congress, Jun. 12-15, Copenhagen, Denmark (1 page).
Fridman, Jordan et al. "Discovery and Preclinical Characterization of INCB018424, a Selective JAK2 Inhibitor for the Treatment of Myeloproliferative Disorders" poster presented at the American Society of Hematology, 49th Annual Meeting and Exposition, GA. Abstract #3538, poster #757, Dec. 10, 2007 (1 page).
Fridman, Jordan et al. "Efficacy and Tolerability of Novel JAK Inhibitors in Animal Models of Rheumatoid Arthritis" poster presented at the ACR/ARHP (American College of Rheumatology/ Association of Rheumatology Health Professionals) Scientific Meeting 2007, Boston, MA. Nov. 10, 2007. Abstract 1771, poster 285 (1 page).
Fridman, Jordan, et al. "Discovery and Preclinical Development of Selective JAK Inhibitors for the Treatment of Hematological Malignancies" poster presented at European Hematology Association, 12th Congress, Vienna, Austria. Abstract 0324, Jun. 8, 2007 (1 page).
Fridman, Jordan, et al. "Discovery and Preclinical Development of Selective JAK Inhibitors for the Treatment of Myeloproliferative Disorders" poster presented at the 4th International Congress on Myeloproliferative Diseases and Myelodysplastic Syndromes, New York, NY. Nov 8-10, 2007. Poster 0009 (1 page).
Forbes et al., "Synthesis and evaluation of a series of aryl [e] fused pyrazolo [4,3-c]pyridines with potential anxiolytic activity," J Medicinal Chem., Jan. 1, 1990, 33(9):2640-2645.
Fonseca et al., "Interleukin-6 as a key player in systemic inflammation and joint destruction," Autoimmun Rev, Jun. 2009, 8(7): 538-42.
Fujihara et al., "Evaluation of human conjunctival epithelium by a combination of brush cytology and flow cytometly: an approach to the quantitative technique", Diagn Cytopathol, 1997;17:456-60.
Fujii, C. et al., "Aberrant expression of serine.thereonine kinase Pim-3 in hepatocellular carcinoma development and its role in the proliferation of human hepatoma cell lines" International Journal of Cancer 114: 209-218, (2005).
Fukagawa et al., "Histological evaluation of brush cytology of rabbit conjunctiva", Nippon Ganka Gakkai Zasshi, 1993;97:1173-8 (contains English abstract within the article).
Gaertner, "Cyclization of 1-Alkylamino-3-halo-2-alkanolst o 1-Alkyl-3-azetidinols," J. Org. Chem., 1967, 32, 2972-76.
Gaestel et al., "Targeting innate immunity protein kinase signalling in inflammation," Nat Rev Drug Discov., Jun. 2009, 8(6):480-99.
Ghelardi, et al., "A Mucoadhesive Polymer Extracted from Tamarind Seed Improves the Intraocular Penetration and Efficacy of Rufloxacin in Topical Treatment of Experimental Bacterial Keratitis", Antimicrob. Agents Chemother. 48:3396-3401 (2004).
Glasson et al., "Differences in clinical parameters and tear film of tolerant and intolerant contact lens wearers", Invest Ophthalmol Vis Sci, 2003;44:5116-5124.
Glattfeld, "Improvements in the Preparation of DL-Threonic and DL-Erythronic Acids", J. Am. Chem. Soc. 62:974-977 (1940).
Gilchrist et al., "5H-2-Pyrindines from 2-Bromocyclopentene-1-carboxaldehyde," Tetrahedron, Jan. 1, 1995, pp. 9119-9126.
Gobbels et al., Tear secretion in dry eyes as assessed by objective fluorophotometry. Ger J Ophthalmol, 1992; 1:350-353.
Golding et al., "X-ray and scanning electron microscopic analysis of the structural composition of tear ferns", Cornea Jan. 1994;13(1):58-66.
Gomtsyan, et al, "Design, synthesis, and structure-activity relationship of 6-alkynylpyrimidines as potent adenosine kinase inhibitors", J. Med. Chem. 45(17):3639-3648 (2002).
Goodman, et al., "IL-6 Signaling in Psoriasis Prevents Immune Suppression by Regulatory T Cells," J. Immunol., Sep. 2009, 183: 3170-3176.
Gooseman, et al., "The intramolecular b-fluorine . . . ammonium interaction in 4- and 8-membered rings", Chem. Commun, vol. 30, pp. 3190-3192 (2006).
Gorr, M.E. et al., "Clinical Resistance to STI-571 Cancer Therapy Caused by BCR-ABL Gene Mutation or Amplification." Science, 293:876, 2001.
Gotlieb, Alice, Presentation at the 2008 American Academy of Dermatology, 66th Annual Meeting, San Antonio, TX. Feb. 1, 2008, symposium-303 (12 pp.).
Goto et al., Color mapping of tear lipid layer thickness distribution from the image analysis in DR-1 tear lipid layer interference images (ARVO abstract). ARVO 2004.
Goto et al., "Computer-synthesis of an interference color chart of human tear lipid layer by a colorimetric approach",Invest Ophthalmol Vis Sci, 2003;44:4693-7.
Goto et al., "Differentiation of lipid tear deficiency dry eye by kinetic analysis of tear interference images", Arch Ophthalmol, 2003;121:173-80.
Goto et al., "Evaluation of the tear film stability after laser in situ keratomileusis using the tear film stability analysis system", Am J Ophthalmol, 2004b Jan;137(1):116-20.
Goto et al., "Tear Film Stability Analysis System: Introducing a new application for videokeratography", Cornea, 2004a; Nov;23(8):S65-S70.
Goto, et al., Kinetic analysis of tear interference images in aqueous tear deficiency dry eye before and after punctal occlusion. Invest Ophthalmol Vis Sci, 2003;44:1897-905.
Gottlieb, A.B., et al, "Psoriasis: Emerging Therapeutic Strategies", Nat Rev Drug Disc., 4:19-34 (2005).

(56) References Cited

OTHER PUBLICATIONS

Grabbe, et al., "Immunoregulatory mechanisms involved in elicitation of allergic—contact hypersensitivity", Immunol Today, Jan; 19(1):37-44 (1998) (only 1 page provide and marked "best available copy").
Greene et al., Greene's Protective Groups in Organic Synthesis, 2007, 4th Edition, 54-55.
Green, T.W. and Wuts, P.G.M.. Protective Groups in Organic Synthesis, 3rd. Ed., Wiley & Sons, Inc., New York (1999).
Greenberg, Int J Ped Hem-Onc 1997;4:231-238.
Greenberg, "The myelodysplastic syndromes" in Hoffman, et al, eds. Hematology: Basic Principles and Practice (3rd ed.), Churchill Livingston; 2000:1106-1129.
Gregory, et al., "Clinical and laboratory features of myelofibrosis and limitations of current therapies", Clinical Advances in Hematology and Oncology, (Sep. 2011) vol. 9, No. 9, pp. 1-3.
Grivennikov, et al., "IL-6 and STAT3 are required for survival of intestinal epithelial cells and the development of colitis-associated cancer", Cancer Cell, 15:103-111 (2009).
Groneberg et al., "Animal models of allergic and inflammatory conjunctivitis," Allergy, 2003, 58, 1101-1113.
Grossman, et al., "Interleukin 6 is expressed in high levels in psoriatic skin and stimulates proliferation of cultured human keratinocytes," Proc. Natl. Acad., Sci. USA, Aug. 1989, 86: 63676371.
Guillon, Jean-Pierre, "Tear film photography and contact lens wear", J Br Contact Lens Assoc, 1982;5:84-7.
Gura, Science, vol. 278, No. 5340, pp. 1041-1042 (1997).
Guschin, et al, "A major role for the protein tyrosine kinase JAK1 in the JAKISTAT signal transduction pathway in response to interleukin-6", Embo J 14:1421-1429 (1995).
Hamze' et al., "Synthesis of Various 3-Substituted 1,2,4-Oxadiazole-Containing Chiral β3—and r-Amino Acids from Fmoc-Protected Aspartic Acid," J. Org. Chem., 2003, 68(19), pp. 7316-7321.
Harris, et al., J Clin Oncol 1999;17:3835-3849.
Hardwicke, et al., "GSK1070916, a potent Aurora B/C kinase inhibitor with broad antitumor activity in tissue culture cells and human tumor xenograft models", Molecular Cancer Therapeutics 8(7), 1808-1817 (2009).
Helal et al., "Stereoselective Synthesis of cis-1,3-Disubstituted Cyclobutyl Kinase Inhibitors," Organic Letters, (2004), 6(11), pp. 1853-1856.
Hickenbottom "Reactions of organic compounds," State Scientific-Technical Publishing Association, Chemical Literature Section, Moscow, 1939, pp. 360-362.
Higuchi, et al., "Pro-drugs as Novel Delivery Systems," vol. 14 of the A.C.S. Symposium Series (1975).
Holly et al., "Lacrimation kinetics in Humans as determined by a novel technique", in Holly FJ (ed). The preocular tear film. Lubbock TX, Lubbock Dry Eye Institute, 1986, pp. 76-88).
Hong, et al., "Total Synthesis of Onnamide A", J. Am. Chem. Soc., 113:9693-94 (1991).
Yu et al., "Role of Janus Kinase/Signal Transducers and Activators of Transcription in the Pathogenesis of Pancreatitis and Pancreatic Cancer," Gut and Liver, Oct. 2012, 6(4): 417-422.
Huang, "Inhibition of STAT3 activity with AG490 decreases the invasion of human pancreatic cancer cells in vitro", Cancer Sci. 97(12):1417-23 (2006).
Huttel, et al., "Lithium pyrazole compounds", Liebigs Ann. Chem. Bd., 625:55-65 (1959) (abstract provided).
Hyung-Bae et al., Transplantation, 2010, 90(8):825-835.
International Preliminary Report on Patentability (with Written Opinion) dated Jun. 18, 2008 for International Appln. No. PCT/US2006/047369 (10 pgs.).
International Preliminary Report on Patentability (with Written Opinion) dated Mar. 6, 2012 for International Appln. No. PCT/US2010/047252 (7 pgs).
International Preliminary Report on Patentability (with Written Opinion) dated Nov. 22, 2011 for International Appln. No. PCT/US2010/035728 (8 pgs.).
International Preliminary Report on Patentability (with Written Opinion) dated Nov. 22, 2011 for International Appln. No. PCT/US2010/035783 (5 pgs.).
International Preliminary Report on Patentability for International Appln. No. PCT/US2008/066662 dated Dec. 17, 2009 (7 pgs.).
International Preliminary Report on Patentability for PCT/US2008/66658 mailed Dec. 17, 2009 (7 pages).
International Preliminary Report on Patentability for PCT/US2009/036635 mailed Sep. 14, 2010 (6 pages).
International Preliminary Report on Patentability for PCT/US2009/059203 mailed Apr. 5, 2011 (6 pages).
International Preliminary Report on Patentability for PCT/US2010/021003 mailed Jul. 19, 2011 (11 pages).
International Preliminary Report on Patentability for PCT/US2010/052011 mailed Apr. 11, 2012 (4 pages).
International Preliminary Report on Patentability for PCT/US2011/025433 mailed Aug. 21, 2012 (7 pages).
International Preliminary Report on Patentability for PCT/US2011/027665 mailed Sep. 11, 2012 (7 pages).
International Preliminary Report on Patentability for PCT/US2011/037291 mailed Nov. 27, 2012 (7 pages).
International Preliminary Report on Patentability for PCT/US2011/061351 mailed May 30, 2013 (7 pages).
International Preliminary Report on Patentability for PCT/US2011/061374 mailed May 30, 2013 (5 pages).
International Preliminary Report on Patentability for PCT/US2012/043099 mailed Dec. 23, 2013, 6 pages.
International Preliminary Report on Patentability for PCT/US2012/050210 mailed Feb. 11, 2014, 8 pages.
International Preliminary Report on Patentability for PCT/US2012/051439 mailed Feb. 27, 2014, 7 pages.
International Preliminary Report on Patentability for PCT/US2012/053921 mailed Mar. 20, 2014, 8 pages.
International Preliminary Report on Patentability for PCT/US2013/041601, issued Nov. 18, 2014, 7 pages.
International Search Report and the Written Opinion, PCT/US2012/051439, mailed Nov. 30, 2012 (15 pages).
International Search Report and the Written Opinion, PCT/US2012/053921, mailed Nov. 7, 2012 (19 pages).
International Search Report and Written Opinion dated Feb. 9, 2010 for International Appln. No. PCT/US2009/059203 (10 pages).
International Search Report and Written Opinion for International Appln. No. PCT/US2005/046207 dated May 15, 2007 (6 pages).
International Search Report and Written Opinion for International Appln. No. PCT/US2008/066662 dated Dec. 23, 2008 (11 pages).
International Search Report and Written Opinion for International Appln. No. PCT/US2009/036635 dated Jun. 3, 2009 14 pages.
International Search Report and Written Opinion for PCT/US2006/047369, 16 pages (Apr. 24, 2007).
International Search Report and Written Opinion for PCT/US2008/083319, 29 pages mailed Mar. 13, 2009.
International Search Report and Written Opinion for PCT/US2011/025433, 12 pages (mailed Jul. 20, 2011).
International Search Report and Written Opinion for PCT/US2011/027665 mailed Jun. 27, 2011 (14 pages).
International Search Report and Written Opinion for PCT/US2011/037291, 11 pages (Apr. 19, 2012).
International Search Report and Written Opinion for PCT/US2011/061351 mailed Feb. 17, 2012 (12 pages).
International Search Report and Written Opinion for PCT/US2011/061374 mailed Mar. 27, 2012 (10 pages).
International Search Report and Written Opinion for PCT/US2012/025581, 16 pages (mailed Apr. 26, 2012).
International Search Report and Written Opinion for PCT/US2012/043099, 11 pages (Sep. 13, 2012).
International Search Report and Written Opinion for PCT/US2012/050252 mailed Jan. 2, 2013, 17 pages.
International Search Report for PCT/US2008/66658 mailed Dec. 23, 2008 (4 pages).

(56) References Cited

OTHER PUBLICATIONS

International Search Report for PCT/US2010/021003 mailed Aug. 16, 2010 (8 pages).
International Search Report for PCT/US2010/035728 mailed Jul. 8, 2010 (3 pages).
International Search Report for PCT/US2010/035783 mailed Aug. 23, 2010 (4 pages).
International Search Report for PCT/US2010/047252 mailed Nov. 17, 2010 (4 pages).
International Search Report for PCT/US2010/052011 mailed Nov. 30, 2010 (3 pages).
International Search Report and Written Opinion in International Application No. PCT/US2014/020554, dated Jul. 16, 2014, 17 pages.
International Search Report in International Application No. PCT/US2013/041601, mailed Sep. 3, 2013, 3 pages.
International Search Report and Written Opinion in International Application No. PCT/US2013/067794, mailed Dec. 17, 2013, 14 pages.
International Search Report and Written Opinion in International Application No. PCT/US2014/051678, dated Feb. 11, 2015, 22 pages.
International Search Report and Written Opinion in International Application No. PCT/US2014/049940, dated Nov. 4, 2014, 13 pages.
Iranpoor, N.; Firouzabadi, H.; Aghapour, "A Rapid and Facile Conversion of Primary Amides and Aldoximes to Nitriles and Ketoximes to Amides with Triphenylphosphine and N-Chlorosuccinimide", G Syn. Commun 32:2535-41 (2002).
Ishizaki, et al., "Pharmacological Properties of Y-27632, a Specific Inhibitor of Rho-Associated Kinases", Molecular Pharmacology, 2000, 57, 976-983.
Itagaki, et al, "Expedient Synthesis of Potent Cannabinoid Receptor Agonist (−)-CP55,940", Organic Letters, 2005; 7(19); 4181-4183.
Jädersten et al., "Long-term outcome of treatment of anemia in MDS with erythropoietin and G-CSF," Blood, Aug. 2005, 106(3): 803-11.
James, et al., "A unique clonal JAK2 mutation leading to constitutive signalling causes polycythaemia vera", Nature, 434 (7037):1144-8 (2005).
Janes, M. et al., "Effective and selective targeting of leukemia cells using a TORC1/2 kinase inhibitor.", Nature Medicine (2010) LNKD-PUBMED:20072130, vol. 16, No. 2, pp. 205-213 XP002673719.
Jee, et al., "Overview: animal models of osteopenia and osteoporosis", J Musculoskel. Neuron, Interact., 1(3):193-207 (2001).
Jester, et al., "In vivo biomcroscopy and photography of meibomian glands in a rabbit model of meibomian gland dysfunction", Invest Ophthalmol Vis Sci, 1982;22:660-7.
Johnson, et al., "The effect of instilled fluorescein solution volume on the values and repeatability of TBUT measurements", Cornea, 2005;24:811-7.
Kaercher, T., "Ocular symptoms and signs in patients with ectodermal dysplasia symdromes", Grafes Arch Clin Exp Ophthalmol, 2004;495-500.
Kamb, Nature Reviews Drug Discovery 4, pp. 161-165 (2005).
Kantarjian et al., "Decitabine improves patient outcomes in myelodysplastic syndromes: results of phase III randomized study," Cancer, Apr. 2006, 106(8): 1794-803.
Kaushansky, K., "Lineage-Specific Hematopoietic Growth Factors", NEJM 354:2034-45 (2006).
Kawamura, et al. (1994). "Molecular cloning of L-JAK, a Janus family protein-tyrosine kinase expressed in natural killer cells and activated leukocytes.", Proc Natl Acad Sci U S A, 91(14): 6374-8).
Kharas, et al., "ABL Oncogenes and Phosphoinositide 3-Kinase. Mechanism of Activation and Downstream Effectors.", Cancer Res., 65(6):2047-2053, Mar. 15, 2005.
Killedar et al., "Early pathogenic events associated with Sjogren's syndrome (SjS)-like disease of the NOD mouse using microarray analysis," Lab Invest, Dec. 2006, 86(12): 1243-1260.

Kim, et al., "Zinc-Modified Cyanoborohydride as a Selective Reducing Agent", J. Org. Chem. 50: 1927-1932(1985).
King-Smith et al., "Three interferometric methods for measuring the thickness of layers of the tear film", Optom Vis Sci, 1999; 76:19-32.
Kiss, Robert, "Recent developments on JAK2 inhibitors: A patent review", Expert Opinion on Therapeutic Patents, (Apr. 2010) vol. 20, No. 4, pp. 471-495.
Kojima et al., "A new noninvasive tear stability analysis system for the assessment of dry eyes", Invest Ophthalmol Vis Sci, 2004; May;45(5):1369-74).
Kola, Nature Reviews Drug Discovery 3, pp. 711-715 (2004).
Komuro et al., "Assessment of meibomian gland function by a newly developed laser meibometer", Adv Exp Med Biol, 2002; 506:517-520.
Korb et al., "The effect of two novel lubricant eye drops on tear film lipid layer thickness in subjects with dry eye symptoms", Optom Vis Sci, 2005; 82: 594-601.
Korb, et al., "Increase in tear film lipid layer thickness following treatment of meibomian gland dysfunction", Adv Exp Med Biol, 1994;350:293-8.
Korolev, et al., "Pd-EDTA as an efficient catalyst for Suzuki-Miyaura reactions in water", Tet. Lett. 46: 5751-5754 (2005).
Kortylewski, et al., "Regulation of the IL-23 and IL-12 balance by Stat3 signaling in the tumor microenvironment", Cancer Cell, 15:114-123 (2009).
Kruh et al., "The complete coding sequence of arg defines the Abelson subfamily of cytoplasmic tyrosine kinases ", Proc. Natl. Acad. Sci., 87:5802-5806, Aug. 1990.
Kubinyi, H. "QSAR. Hansch Analysis and Related Approaches," Methods and Principles in Medicinal Chemistry, Manhold, R. ed. Weinhein, NY, 1993.
Kudelacz, et al. "The JAK-3 inhibitor CP-690550 is a potent anti-inflammatory agent in a murine model of pulmonary eosinophilia", European Journal of Pharmacology 582 (2008) 154-161.
Kumar, C., "Kinase drug discovery approaches in chronic myeloproliferative disorders", Oncogene, (Jun. 18, 2009) vol. 28, No. 24, pp. 2305-2323.
Kuo, et al., "Pd-EDTA as an efficient catalyst for Suzuki-Miyaura reactions in water", Chem Commun 301-3 (2007).
Kuppens et al., "Basal tear turnover and topical timolol in glaucoma patients and healthy controls by Fluorophotometry", Invest Ophthalmol Vis Sci, 1992; 33:3442-3448.
Kurzrock et al., "A Phase I, Open-Label Study of Siltuximab, an Anti-IL-6 Monoclonal Antibody, in Patients with B-cell Non-Hodgkin Lymphoma, Multiple Myeloma, or Castleman Disease," Clin. Cancer Res., published online May 9, 2013, 39 pages.
Kurzrock et al., "Serum Interleukin 6 Levels Are Elevated in Lymphoma Patients and Correlate with Survival in Advanced Hodgkin's Disease and with B Symptoms," Cancer Res., May 1993, 52: 2118-2122.
Lai, et al., "Mechanistic Study on the Inactivation of General Acyl-CoA Dehydrogenase by a Metabolite of Hypoglycin A", J. Am. Chem. Soc. 113: 7388-7397 (1991).
Lam, et al, "Tear Cytokine Profiles in Dysfunctional Tear Syndrome", Am J Ophthalmol , 147(2):198-205 (2009).
Larock, R., "Comprehensive Organic Transformations", Wiley-VCH, 2nd Ed. (1999) pp. 1949-50, 1958-59, 1976, and 1983-1985.
Larson, "Myelodysplasia: when to treat and how," Best Pract Res Clin Haematol, 2006, 19(2): 293-300.
Leaf, Clifton, Health Administrator vol. XVII, No. 1:172-183 (2005).
Lemp "Report of National Eye Institute/Industry Workshop on clinical trials in dry eyes", CLAO J, 1995;21:221-232.
Lemp et al., "Corneal desiccation despite normal tear volume", Ann Ophthalmol, 1970 (2) pp. 258-261 & 284.
Lemp et al., "The Definition and Classification of Dry Eye Disease: Report of the Definition and Classification Subcommittee of the International Dry Eye WorkShop", The Ocular Surface, 5(2), 75-92 Apr. 2007.
Letter translation of Office Action, Chilean Application No. 3496-2006 as received from the foreign associate (Jul. 5, 2010) (4 pages).

(56) References Cited

OTHER PUBLICATIONS

Levine, et al., "Activating mutation in the tyrosine kinase JAK2 in polycythemia vera, essential thrombocythemia, and myeloid metaplasia with myelofibrosis", Cancer Cell, vol. 7, 2005: 387-397.
Levitzki, "Tyrosine kinases as targets for cancer therapy", Eur. J. Cancer 38(suppl. 5):S11-S18 (2002).
Levy, et al. "INCB018424 A Selective Janus Kinase ½ Inhibitor" Presentation at the 50th American Society of Hematology Annual Meeting (ASH), Dec. 8, 2008.
Verstovsek, et al., INCB18424 Discussion presentation at the American Society of Hematology, 49th Annual Meeting and Exposition, Atlanta, GA. Abstract #558, Dec. 10, 2007 (25 pages).
Li, et al., "Pim-3, a proto-oncogene with serine/threonine kinase activity, is aberrantly expressed in human pancreatic cancer and phosphorylates Bad-mediated apoptosis in human pancreatic cell lines" Cancer Research 66(13): 6741-7 (2006).
Liesveld and Lichtman, Chapter 88. "Myelodysplastic Syndromes (Clonal Cytopenias and Oligoblastic Myelogenous Leukemia)", in Prchal et al, eds. Williams Hematology. 8th ed., New York: McGraw-Hill; 2010.
Lima and Barreiro, "Bioisosterism: a useful strategy for molecular modification and drug design," Curr Med Chem. 2005;12(1):23-49.
Lin, "Constitutive Activation of JAK3/STAT3 in Colon Carcinoma Tumors and Cell Lines", Am J Pathol. 167(4):969-80 (2005).
Lin, et al., "Enantioselective synthesis of Janus kinase inhibitor INCB018424 via an organocatalytic aza-Michael reaction," Organic Letters, (2009), 11(9), 1999-2002.
List et al., "Efficacy of lenalidomide in myelodysplastic syndromes," N Engl J Med, Feb. 2005, 352(6): 549-57.
Liu, et al., "Combined Inhibition of Janus Kinase ½ for the Treatment of JAK2V617F-Driven Neoplasms: Selective Effects on Mutant Cells and Improvements in Measures of Disease Severity", Clin Cancer Res 2009;15(22) pp. 6891-6900; Nov. 15, 2009; Published Online First on Nov. 3, 2009 as 10.1158/1078-0432.CCR-09-1298.
Lübbert, et al., "Cytogenic responses in high-risk myelodysplastic syndrome following low-dose treatment with the DNA methylation inhibitor 5-aza-2'-deoxycytidine," Br J Haematol, Aug. 2001, 114(2): 349-57.
Lübbert, et al., "Low-dose decitabine versus best supportive care in elderly patients with intermediate- or high-risk myelodysplastic syndrome (MDS) ineligible for intensive chemotherapy: final results of the randomized phase III study of the European Organisation for Research and Treatment of Cancer Leukemia Group and the German MDS Study Group," J Clin Oncol, May 2011, 29(15): 1987-96.
Lucet et al., "The structural basis of Janus kinas 2 inhibition by a potent and specific pan-Janus kinase inhibitor," Blood, 2006, 107(1):176-183.
Macchi, et al., "Mutations of Jak-3 gene in patients with autosomal severe combined immune deficiency (SCID)", Nature 377:65-8 (1995).
Madden et al. Comparative study of two non-invasive tear film stability techniques. Curr Eye Res, 1994; 13(4):263-9.
Madhusudan et al., "Tyrosine kinase inhibitors in cancer therapy", Clin Biochem., 2004, 37(7):618-35.
Maffioli, et al., "Mild and Reversible Dehydration of Primary Amides with PdC12 in Aqueous Acetonitrile", Organic Letters vol. 7 No. 23, 5237-39 (2005).
Main et al, "High throughput synthesis of diverse 2,5-disubstituted indoles using titanium carbenoids bearing boronate functionality", Tetrahedron, 64(5):901-914 (2007).
Mainstone et al., "Tear meniscus measurement in the diagnosis of dry eye", Curr Eye Res, 1996; 15:653-661.
Mancini, M. et al., "RAD 001 (everolimus) prevents mTOR and Akt late re-activation in response to imatinib in chronic myeloid leukemia.", J. Cellular Biochemistry (2010) LNKD-PUBMED:20014066, XP-002673720. vol. 109, No. 2 (2010) pp. 320-328.

Mandal, "Cancer Classification," 2014. Available from: <http://www.news-medical.net/health/Cancer-Classification.aspx, 6 pages.
Manjula, et al., "Rapid Method of Converting Primary Amides to Nitriles and Nitriles to Primary Amides by ZnC12 using Microwaves under Different Reaction Conditions", Syn. Commun 37:1545-50 (2007).
Manning, et al., "The Protein Kinase Complement of the Human Genome", Science. 2002, 298(5600):1912-16 and 1933-34.
March, Jerry, Advanced Organic Chemistry: Reactions, Mechanisms, and Structure, 3rd ed., John Wiley & Sons:New York, pp. 845-855 (1985).
Marquardt et al., "Modification of tear film break-up time test for increased reliability" in Holly ed. The Preocular Tear Film inHealth, Disease and Contact Lens Wear. Lubbock, Texas: Dry Eye Institute, 1986:57-63.
Maruyama et al., "Effect of environmental conditions on tear dynamics in soft contact lens wearers", Invest Ophthalmol Vis Sci, 2004;45(8):2563-8.
Mathers et al., "Assessment of the tear film with tandem scanning confocal microscopy", Cornea, 1997;16:162-8.
Mathers et al., "Tear film changes associated with normal aging", Cornea, 1996; 15:229-334.
Mathers et al., "Tear flow and evaporation in patients with and without dry eye", Ophthalmology, 1996; 103:664-669.
Mathers et al., "Video imaging of the meibomian gland", Arch Ophthalmol, 1994;112:448-9.
Mathers, "Evaporation from the ocular surface", Exp Eye Res, 2004; 78:389-394.
Mascarenhas et al., "Ruxolitinib: The First FDA Approvided Therapy for the Treatment of Myelofibrosis," Clinical Cancer Research, Jun. 2012, 18(11): 3008-3014.
Maxson et al., "Oncogenic *CSF3R* Mutations in Chronic Neutrophilic Leukemia and Atypical CML," *N. Engl. J. Med.*, 2013, 368(19):1781-1790.
Mayo Clinic. Available at: < http://www.mayoclinic.com/health/pancreatic-cancer/DS00357 >. 2 pages, retrieved from the Internet Apr. 3, 2013.
Mayo Clinic. Available at: < http://www.mayoclinic.com/health/prostate-cancer-prevention/MC00027 >. 3 pages, retrieved from the Internet Apr. 3, 2013.
Mayo Clinic. Available at: <http://www.mayoclinic.com/health/crohns-disease/DS00104/DSECTION=treatments-and-drugs> 6 pages, retrieved from the Internet May 27, 2013.
Mayo Clinic. Available at: <http://www.mayoclinic.com/health/multiple-sclerosis/DS00188/DSECTION=treatments-and-drugs>. 3 pages, retrieved from the Internet May 27, 2013.
Mayo Clinic. Available at: <http://www.mayoclinic.com/health/my-asthenia-gravis/DS00375> 2 pages, retrieved from the Internet May 27, 2013.
Mayo Clinic. Available at: <http://www.mayoclinic.com/health/rheumatoid-arthritis/DS00020/DSECTION=treatments-and-drugs> 3 pages, retrieved from the Internet Jun. 26, 2013.
Mayo Clinic. Available at: <http://www.mayoclinic.org/diseases-conditions/type-1-diabetes/basics/prevention> 2014, 19 pages.
McNamara et al., "Fluorometry in contact lens research: The next step", Optom Vis Sci, 1998; 75:316-322.
MD Anderson Cancer Center. "Leukemia Prevention and Screening," 2014, 2 pages.
MD Anderson Cancer Center. "Myeloproliferative Disease Prevention and Screening," 2014, 2 pages.
Mengher et al., "Non-invasive tear film break-up time: sensitivity and specificity", Acta Ophthalmol (Copenh), 1986; 64(4):441-4.
Mesa, et al. "INCB018424, A Selective JAK ½ Inhibitor, Significantly Improves the Compromised Nutritional Status and Frank Cachexia in Patients with Myelofibrosis (MF)" Poster #1760 at the American Society of Hematology Annual Meeting (ASH), Dec. 6, 2008 (19 pages).
Mesa, et al., "Evaluating the serial use of the myelofibrosis symptom assessment form for measuring symptomatic improvement: Performance in 87 myelofibrosis patients on a JAK1 and JAK2 inhibitor (INCB018424) clinical trial", Cancer, (Nov. 1, 2011) vol. 117, No. 21, pp. 4869-4877.

(56) References Cited

OTHER PUBLICATIONS

Mesa, R. et al., "Emerging drugs for the therapy of primary and post essential thrombocythemia, post polycythemia vera myelofibrosis", Expert Opinion on Emerging Drugs England, vol. 14, No. 3 (2009) pp. 471-479.

Methods in Molecular Biology: vol. 225, Inflammation Protocols., Winyard, P.G. and Willoughby, D.A., Humana Press, 2003.

Meydan et al., "Inhibition of acute lymphoblastic leukaemia by a Jak-2 inhibitor", Nature. Feb. 15, 1996;379(6566):645-8.

McMillan, "The systemic inflammation-based Glasgow Prognostic Score: a decade of experience in patients with cancer," Cancer Treat Rev, Aug. 2013, 39(5): 534-40.

Miethchen, "Micelle-activated reactions. I. Micelle-activated iodination and partial dehalogenation of pyrazoles and 1,2,4-triazoles", Journal F. prakt. Chemie, Band 331, Heft 5, S. 799-805 (1989) (1 page abstract also provided).

Milici, A.J., et al., "Cartilage preservation by inhibition of Janus kinase 3 in two rodent models of rheumatoid arthritis", Arthritis Research & Therapy, 2008, 10:R14 (http://arthritis-research.com/content/10/1/R14) (9 pages).

Minegishi, et al., "Human Tyrosine Kinase 2 Deficiency Reveals Its Requisite Roles in Multiple Cytokine Signals Involved in Innate and Acquired Immunity", Immunity 25:745-55 (2006).

Mishchenko et al., "Treatment options for hydroxyurea-refractory disease complications in myeloproliferative neoplasms: JAK2 inhibitors, radiotherapy, splenectomy and transjugular intrahepatic portosystemic shunt", Eur J Haematol. Sep. 2010;85(3):192-9. Epub Jun. 2, 2010.

Mishima, et al., "Determination of tear volume and tear flow", Invest Ophthalmol, 1966; 5:264-276.

Mishima, S., "Some physiological aspects of the precorneal tear film", Arch Ophthalmol, 1965;73:233-241.

Mitsunobu, O., "The Use of Diethyl Axodicarboxylate and Triphenylphosphine in Synthesis and Transformation of Natural Products." Synthesis (1): 1-28 (1981).

Miyata, et al., "Stereospecific nucleophilic addition reactions to olefins.", J. Org. Chem. 56:6556-6564 (1991).

Miyaura et al., "Palladium-Catalyzed Cross-Coupling Reactions of Organoboron Compounds," Chem. Rev., 1995, 95, 2457-2483.

Miyoshi et al., "Interleukin-8 concentrations in conjunctival epithelium brush cytology samples correlate with neutrophil, eosinophil infiltration, and corneal damage", Cornea, 2001;20:743-7.

Molldrem, et al., "Antithymocyte globulin for patients with myelodysplastic syndrome," Br J Haematol, Dec. 1997, 99(3): 699-705.

Moreland, et al. "A Randomized Placebo-Controlled Study of INCB018424, a Selective Janus Kinase 1&2 (JAK 1&2) Inhibitor in Rheumatoid Arthritis (RA)" Presentation at the American College of Rheumatology meeting, Oct. 26, 2008. (20 pages).

Moriarty, et al., "The synthesis and SAR of 2-amino-pyrrolo[2,3-d]pyrimidines: A new class of Aurora-A kinase inhibitors", Bioorganic and Medicinal Chemistry Letters, 16(22), 5778-5783 (2006).

Mosby's Dictionary of Medicine, Nursing, & Health Professions, sicca complex, 2009, Elsevier, printed from http://www.credoreference.com/entry/ehsmosbymed/sicca_complex, 2 pages.

Mullighan, et al, "JAK mutations in high-risk childhood acute lymphoblastic leukemia", Proc Natl Acad Sci USA. 106:9414-8 (2009).

Mundle, et al. Am J Hematol 1999;60:36-47.

Naka T., "The paradigm of IL-6: from basic science to medicine", Arthritis Res., 2002;4 Suppl 3:S233-42.

Nakagawara, Akira, "Trk receptor tyrosine kinases. A bridge between cancer and neural development." Cancer Letters, 169:107-114, 2001.

Nally et al., "Ocular discomfort and tear film break-up time in dry eye patients: A correlation", Invest Ophthalmol Vis Sci, 2000;41:4:1436 (Poster Presentation).

Naqvi, et al., "A potential role of ruxolitinib in leukemia", Expert Opinion on Investigational Drugs, (Aug. 2011) vol. 20, No. 8, pp. 1159-1166.

National Cancer Institute, "FDA Approval for Ruxolitinib Phosphate", http://www.cancer.gov/cancertopics/druginfo/fda-ruxolitinibphosphate posted Nov. 18, 2011 (3 pages).

Naus, et al., "6-(Het)aryl-7-Deazapurine Ribonucleosides as Novel Potent Cytostatic Agents", J. Med. Chem., 53(1):460-470 (2010).

Neidle, Stephen, Cancer Drug Design and Discovery, (Elsevier/Academic Press, 2008) pp. 427-431.

Nelson et al., "Tear film osmolality determination: an evaluation of potential errors in measurement" Curr Eye Res, Sep;5(9):677-81, 1986.

Neubauer, H., et al., "Jak2 Deficiency Defines an Essential Developmental Checkpoint in Definitive Hematopoiesis", Cell, 93(3): 397-409 (1998).

Neuner, et al., J. Invest. Dermatol. 1991, 97, 27-33.

Nicholoff et al., "Recent Insights into the immunopathogenesis of psoriasis provide new therapeutic opportunities", J. Clin. Invest., 113; 1664-1675 (2004).

Nichols et al., "The lack of association between signs and symptoms in patients with dry eye disease", Cornea, vol. 23(8):762-770 (2004).

Nichols et al., "The repeatability of clinical measurements of dry eye", Cornea, vol. 23(3):272-85 (2004).

Nishimoto et. al., "Improvement in Castleman's disease by humanized anti-interleukin-6 receptor antibody theraphy," *Blood*, 2000, 95(1):56-61.

Nishio, et al., "Tyrosine kinase-dependent modulation by interferon-α of the ATP-sensitive K+ current in rabbit ventricular myocytes", FEBS Letters, (1999), 445, 87-91.

Nitta, et al., "Peptide-Titanium Complex as Catalyst for Asymmetric Addition of Hydrogen Cyanide to Aldehyde", J. Am. Chem. Soc., 1992, 114, 7969-75 (1992).

Norman, "Selective JAK1 inhibitor and selective Tyk2 inhibitor patents," *Expert Opinion*, Informa Healthcare. 2012, available at: <http://informahealthcare.com/dol/podfplus/10.1517/13543776.2012.723693>.

Norn, M., "Quantitative tear ferning. Clinical investigations", Acta Ophthalmol (Copenh), Jun. 1994;72(3):369-72.

Notice of Allowance and Fee(s) Due dated Sep. 21, 2007 in connection with U.S. Appl. No. 11/313,394 (6 pages).

Notice of Hearing and Preliminary Report for EP Patent 1966202, dated Mar. 18, 2013 (7 pages).

Office Action (Non-final) dated Aug. 22, 2007 in connection with U.S. Appl. No. 11/115,702 (9 pages).

Office Action (Non-final) dated Dec. 3, 2007 in connection with U.S. Appl. No. 11/524,641 (13 pages).

Office Action (Non-final) dated Feb. 25, 2009 for U.S. Appl. No. 12/137,892 (13 pgs.).

Office Action (Final) dated Feb. 7, 2008 for U.S. Appl. No. 11/115,702 (5 pages).

Office Action (Final) dated Jan. 29, 2014 in U.S. Appl. No. 13/043,986, 10 pages.

Office Action (Final) dated Nov. 30, 2009 for U.S. Appl. No. 12/137,892 (9 pgs.).

Office Action (Non-final) dated Apr. 20, 2007 in connection with U.S. Appl. No. 11/313,394 (16 pages).

Office Action in U.S. Appl. No. 14/186,338, mailed May 5, 2014, 18 pages.

Office Action received for European Application No. 06 839 328.9 (Jan. 22, 2009) (5 pages).

Office Action received for Japanese Application No. 2008-545733 dated Oct. 11, 2011 (5 pages).

Office Action received for New Zealand Application No. 569015 dated Feb. 24, 2010 (2 pages).

Office Action received for Singapore Application No. 2008-04386-1 (Aug. 24, 2010).

Office Action received for Vietnamese Patent Application No. 1-2011-03188 dated Mar. 8, 2012 as translated by foreign associate (10 pages).

Office Action, Canadian Patent Office, Application No. 2,632,466, dated May 8, 2012 (3 pages).

(56) References Cited

OTHER PUBLICATIONS

Office Action, China, Patent Application No. 201080033308.6 dated Aug. 2, 2013, 10 pages.
Office Action, Eurasian Patent Office, prepared Feb. 5, 2010.
Office Action, European Patent Office, Application No. 06 839 328 9 mailed Oct. 21, 2010.
Office Action, European Patent Office, mailed Nov. 6, 2009 Application 06839328.9.
Office Action, Mexico, Patent Appl. No. MX/a/2008/007635 as received from foreign associate dated Jun. 15, 20101 (1 page).
Office Action, Mexico, Patent Appl. No. MX/a/2008/007635 as received from foreign associate dated Nov. 13, 2009 (4 pages).
Office Action/Examination Report received for Pakistan Application No. 211/2009 dated Jan. 18, 2010 (1 page).
Oguz, et al., "The height and radius of the tear meniscus and methods for examining these parameters", Cornea, 2000;19:497-500.
Opposition for EP Patent 1966202, filed on Jun. 21, 2012 (30 pages).
Opposition for India Patent Application No. 2365/KOLNP/2008 dated Nov. 12, 2012 (received by Applicants from Indian associate on Apr. 17, 2013) 37 pages.
Opposition, Costa Rica, translation from Foreign Associate Dated Jun. 13, 2012, 6 pages.
Opposition, Costa Rica, translation from Foreign Associate Dated Nov. 20, 2013, 9 pages.
Opposition, Ecuador Patent Office, mailed Nov. 18, 2008 1 page letter from Foreign Associate enclosing the translation (5 pages) of the Opposition.
Ortmann, et al., "Janus kinases and signal transducers and activators of transcription: their roles in cytokine signaling, development and immunoregulation " Arthritis Res, 2(1): 16-32 (2000).
Ostojic et al., "Ruxolitinib for the treatment of myelofibrosis", Drugs of Today, (Nov. 2011) vol. 47, No. 11, pp. 817-827.
Ousler, et al., "Factors that influence the inter-blink interval (IBI) as measured by the ocular protection index (OPI)", Invest Ophthalmol Vis Sci 2001; 43: E-abstract 56 (Poster presentation) ARVO (2002) 2 pages, downloaded from http://abstracts.iov.s.org/cgi/content/abstract/43/12/56?maxtoshow on Aug. 14, 2009.
Palmer, et al., "Multiple roles of ephrins in morphogenesis, neuronal networking, and brain function." Genes & Dev., 17:1429-1450, 2003.
Panteli et al., "Serum interleukin (IL)-1, IL-2, sIL-2Ra, IL-6 and thrombopoietin levels in patients with chronic myeloproliferative diseases," British Journal of Haematology, 2005, 130, 709-715.
Pardanani A., "JAK2 inhibitor therapy in myeloproliferative disorders: rationale, preclinical studies and ongoing clinical trialsJAK2 inhibitor therapy in MPD", Leukemia 22, 23-30 (Jan. 2008).
Parganas, E., D. Wang, et al., "Jak2 is Essential for Signaling through a Variety of Cytokine Receptors", (1998). Cell, 93(3): 385-95.
Park et al., "Homogeneous Proximity Tyrosine Kinase Assays: Scintillation Proximity Assay versus Homogeneous Time-Resolved Fluorescense", Analytical Biochemistry, 1999, 269, 94-104.
Parks, "Tofacitinib and Other Kinase Inhibitors Offer New Approach to Treating Rheumatoid Arthritis," Rheumatologist, Jun. 2013, pp. 1-12 Available from: <http://www.the-rheumatologist.org/details/article/4871781/Tofacitinib_and_Other_Kinase_Inhibitors_Offer_New_Approach_to_Treating_Rheumatoi.html>, 12 pages.
Kaddis et al., "Second-Line Treatment for Pancreatic Cancer," Journal of the Pancreas, Jul. 2014, XP055147286, Retrieved from the Internet: URL: http://www.serena.unina.it/index.php/jop/article/viewFile/2691/2737 [retrieved on Oct. 17, 2014].
Patani, et al., "Bioisosterism: A Rational Approach in Drug Design", Chem. Rev., 1996, 96, 3147-3176.
Patrick, Graham L , "An Introduction to medicinal chemistry" *Oxford University Press Inc.*, New York, 1995 (31 pages) (cited in Opposition from India dated Nov. 12, 2012.

Pearce et al., "Spatial location studies on the chemical composition of human tear ferns", Ophthalmic Physiol Opt, (2000) vol. 20(4):306-13.
Pearce, et al., "An improved fluorophotometric method for tear turnover assessment", Optom Vis Sci, (2001) 78(1):30-36).
Pedranzini, et al., Cancer Res., 66(19):9714-9721 (2006).
Pensyl et al., "The repeatability of tear mucus ferning grading", Optom Vis Sci, Aug. 1998;75(8):600-4.
Pernis, et al., "JAK-STAT signaling in asthma." J Clin Invest, 109(10): 1279-83 (2002).
Peters, K. G. et al., "Functional Significance of Tie2 Signaling in the Adult Vasculature", 2004, © The Endocrine Society (21 pages).
Pflugfelder, et al., "Evaluation of subjective assessments and objective diagnostic tests for diagnosing tear-film disorders known to cause ocular irritation", Cornea, 1998;17(1):38-56.
Pillonel, Christian, "Evaluation of phenylaminopyrimidines as antifungal protein kinase inhibitors", Pest Management Science, Wiley & Sons, vol. 61, Jun. 13, 2005 pp. 1069-1076.
Pirard, B. et al., "Classification of Kinase Inhibitors Using BCUT Descriptors", J. Chem. Inf. Comput. Sci., 2000, 40, 1431-1440.
Pisella et al., Flow cytometric analysis of conjunctival epithelium in ocular rosacea and keratoconjunctivitis sicca. Ophthalmology, 2000;107:1841-1849.
Pisella, et al., Conjunctival proinflammatory and proapoptotic effects of latanoprost, preserved timolol and unpreserved timolol: an ex vivo and in vitro study. Invest Ophthalmol Vis Sci, 2004;45:1360-1368).
Portnaya, et. al., "Azomethine dyes. IV. Indoaniline dyes derived from heterocyclic N-substituted 1-hydroxy-2-naphthamid", Ts Vses Nauchn Issled Kinofotoinst, Issue 40, (1960) pp. 106-108 (with English abstract 20 pages total).
Prchal et al, eds. Williams Hematology. 8th ed., New York: McGraw-Hill; 2010.
Press Release dated Sep. 18, 2008: "Incyte's Topical JAK Inhibitor Demonstrates Positive Proof-of-Concept Results in Patients with Mild to Moderate Psoriasis" (4 pages).
Prezent, et al., "Boron chelates as intermediates in the synthesis of new functionalized pyridines and pyrimidines from a, a-dioxoketene aminals", Proceedings of the International Conference on the Chemistry of Boron, vol. 11 (2003) (abstract only—1 page).
Punwani, Naresh, et al. "Efficacy and safety of topical INCB018424, a selective Janus kinase 1 & 2(JAK1&2) inhibitor in psoriasis." Journal of the American Academy of Dermatology. vol. 60. No. 3. 360 Park Avenue South, New York, NY 10010-1710 USA: Mosby-Elsevier, 2009.
Punwani et al., Poster/presentation, "Initial Efficacy and Safety of Topical INCYB018424 Cream, a Selective Janus Kinase 1&2 (JAK 1&2) Inhibitor in Psoriasis" 17th Congress of the European Academy of Dermatology and Venereology, Paris, France, Sep. 17, 2008 (15 pages).
Quesada et al, "One-pot conversion of activated alcohols into 1,1-dibromoalkenes and terminal alkynes using tandem oxidation processes with manganese dioxide", Tetrahedron, 62 (2006) 6673-6680.
Quintas-Cardama et al., "Preclinical characterization of the selective JAK1/2 inhibitor INCB018424: therapeutic implications for the treatment of myeloproliferative neoplasms", Blood First Edition Paper, prepublished online Feb. 3, 2010, American Society of Hematology; DOI 10.1182/blood-2009-04-214957, 115(15):3109-3117.
Ravin, L., "Preformulation", Remington's Pharmaceutical Sciences, 17th ed., Mack Publishing Company, Easton, Pa., 1985, Chapter 76, pp. 1409-1423.
Raza et al., "Apoptosis in bone marrow biopsy samples involving stromal and hematopoietic cells in 50 patients with myelodysplastic syndromes," Blood, Jul. 1995, 86(1): 268-76.
Raza, et al, Int J Hematol 1996a;63:265-278.
Raza, et al., Leuk Res 1996b;20:881-890.
Raza et al., "Phase 2 Study of lenalidomide in transfusion-dependent, low-risk, and intermediate-1 risk myelodysplastic syndromes with karyotypes other than deletion 5q," Blood, Jan. 2008, 111(1): 86-93.

(56) References Cited

OTHER PUBLICATIONS

Ren et al., "Compounds and Compositions as Protein Kinase Inhibitors," U.S. App. No. 60/578,491, filed Jun. 10, 2004 (56 pages).
Response and Amendment dated Aug. 25, 2009 to non-final Office Action for U.S. Appl. No. 12/137,892 (34 pgs.).
Response and Amendment in Reply to Action of Apr. 20, 2007 filed Jul. 17, 2007 for U.S. Appl. No. 11/313,394 (39 pages).
Response to Action of Aug. 22, 2007 dated Nov. 19, 2007, U.S. Appl. No. 11/115,702 (7 pages).
Response to Restriction Requirement dated May 29, 2007, U.S. Appl. No. 11/115,702 (8 pages).
Restriction Requirement dated Mar. 6, 2007 in connection with U.S. Appl. No. 11/115,702 (8 pages).
Reuters, "Jakafi (ruxolitinib) improved advanced pancreas cancer outcomes in mid-stage trial," Internet Citation, Aug. 21, 2013, pp. 1-2, XP002717211, Retrieved from Internet: URL: http://www.curetoday.com/index.cfm/fuseaction/news.showNewsArticle/id/I3/news_id/3785 [retrieved on Nov. 29, 2013].
Roberts, Jr., et al., JAMA 292(17):2130-2140 (2004).
Robin et al., In vivo transillumination biomicroscopy and photography of meibomian gland dysfunction. Ophthalmology, 1985;92:1423-6.
Rodig, et al., "Disruption of the Jak1 gene demonstrates obligatory and nonredundant roles of the Jaks in cytokine-induced biologic responses." Cell, 93(3): 373-83 (1998).
Rolando et al., "Tear mucus crystallization in children with cystic fibrosis", Ophthalmologica, 1988;197(4):202-6).
Rolando et al., "Tear mucus ferning test in keratoconjunctivitis sicca", Holly FJ, Lamberts DW, MacKeen DL (eds.): The preocular tear film in health, disease, and contact lens wear,. 1st Intern Tear Film Symposium. Lubbok (Texas, USA), Dry Eye Institute, 1986, 203-210.
Rolando et al., "The effect of hyperosmolarity on tear mucus ferning", Fortschr Ophthalmol, 1986;83:644-646.
Rolando et al., The Ocular Surface and Tear Film and Their Dysfuntion in Dry Eye Disease, Survey of Ophthalmology, Mar. 2001, vol. 45, Supplement 2, S203-S210.
Rolando, M. "Tear mucus ferning test in normal and keratoconjunctivitis sicca eyes." Chibret Int J Ophthalmol, 1984;2(4):32-41.
Roudebush et al., "Pharmacologic manipulation of a four day marine delayed type hyper sensitivity model", Agents Actions, 1993, 38(1-2):116-21.
Rousvoal, G. et al. "Janus kinase 3 inhibition with CP-690,550 prevents allograft vasculopathy", Transpl Int., 2006 19(12):1014-21.
Saemann, et al., "Prevention of CD40-triggered dendritic cell maturation and induction of T-cell hyporeactivity by targeting of Janus kinase 3." Am J Transplant, 3(11): 1341-9 (2003).
Saettone et al. "Ocular inserts for topical delivery," Advanced Drug Delivery Reviews, 16: 95-106, 1995.
Samanta et al., "Janus kinase 2: a critical target in chronic myelogenous leukemia", Cancer Res. Jul. 1, 2006;66(13):6468-72.
Sawada et al, "Increased Lipophilicity and Subsequent Cell Partitioning Decrease Passive Transcellular Diffusion of Novel, Highly Lipophilic Antioxidants", The Journal of Pharmacology and Experimental Therapeutics, 1999, No. 288, vol. 3, pp. 1317-1326, p. 1321, compound 26.
Schiffer, "Clinical issues in the management of patients with myelodysplasia," Hematology Am Soc Hematol Educ Program, 2006: 205-10.
Schiffer, "Myelodysplasia: the good, the fair and the ugly," Best Pract Res Clin Haematol, Mar. 2007, 20(1): 49-55.
Schindler et al., "Hormones and Signaling: Cytokines and STAT Signaling", Adv Pharmacol. 2000; 47:113-74.
Schrader et al., "Animal Models of Dry Eye," Developmental Opthalmology, Karger 2008, 41, 298-312.
Scott, et al., "Jaks, STATs, Cytokines, and Sepsis." Clin Diagn Lab Immunol, 9(6): 1153-9 (2002).

Search Report in TW Application No. 100117866, dated Dec. 2014, 1 page.
Seefeld, et al, "Discovery of 5-pyrrolopyridinyl-2-thiophenecarboxamides as potent AKT kinase", Bioorganic & Medicinal Chemistry Letters, 19(8):2244-2248 (2009).
Seela, et al., "Synthesis of Pyrrolo[2,3-d]pyrimidine 2', 3'-Dideoxyribenucleosides Related to 2',3 '—Dideoxyadenosine and 2',3 '-Dideoxgtuanosine and Inhibitory Activity of 5'-Triphosphates on HIV-1 Reverse Transcriptase", Helvetica Chimica, Acta, 1991, 74(3), 554-64.
Seki, "STAT3 and MAPK in human lung cancer tissues and suppression of oncogenic growth by JAB and dominant negative STAT3", Int J Oncol. 24(4):931-4 (2004).
Seto, et al. (2003). "Enhanced Th2 cell-mediated allergic inflammation in Tyk2-deficient mice." J Immunol, 170(2): 1077-83.
Shah et al., "Multiple BCR-ABL kinase domain mutations confer polyclonal resistance to the tyrosine kinase inhibitor imatinib (STI571) in chronic phase and blast crisis chronic myeloid leukemia " Cancer Cell, 2:117-125, Aug. 2002.
Shi, et al., "The pharmacokinetics, pharmacodynamics, and safety of orally dosed INCB018424 phosphate in healthy volunteers", Journal of Clinical Pharmacology, (Dec. 2011) vol. 51, No. 12, pp. 1644-1654.
Shimazaki et al., "Meibomian gland dysfunction in patients with Sjogren syndrome", Ophthalmology, 1998;105(8):1485-8.
Silverman et al., "Further analysis of trials with azacitidine in patients with myelodysplastic syndrome: studies 8421, 8921, and 9221 by the Cancer and Leukemia Group B," J Clin Oncol, Aug. 2006, 24(24): 3895-903.
Silverman et al., "Randomized controlled trial of azacitidine in patients with the myelodysplastic syndrome: a study of the cancer and leukemia group B," J Clin Oncol, May 2002, 20(10): 2429-40.
Sloand et al., "Factors affecting response and survival in patients with myelodysplasia treated with immunosuppressive therapy," J Clin Oncol, May 2008, 26(15): 2505-11.
Smith et al, "Basic pathogenic mechanisms operating in experimental model acute anterior uveitis," Immunology and Cell Biology, 1998, 76, 497-512.
Smolen, et al, "Effect of interleukin-6 receptor inhibition with tocilizumab in patients with rheumatoid arthritis (OPTION study): a double-blind, placebo-controlled, randomized trial", Lancet 371:987, 2008 (2008).
Sonbol et al., "Comprehensive review of JAK inhibitors in myeloproliferative neoplasms," Therapeutic Advances in Hematology, 2013, 4(1): 15-35.
Song et al. "JAK1 Activates STAT3 Activity in Non-Small-Cell Lung Cancer cells and IL-6 Neutralizing Antibodies can Suppress JAK1-STAT3 Signaling," Mol Cancer Ther., Mar. 2011, 10(3): 481-94.
Spoerl et al., *Blood*, 2014, 123(24): 3832-3842.
Sriram, K. et al., "Induction of gp130-related Cytokines and Activation of JAK2/STAT3 Pathway in Astrocytes Precedes Up-regulation of Glial Fibrillary Acidic Protein in the 1-Methyl-4-phenyl-1,2,3,6-tetrahydropyridine Model of Neurodengeneration", J. Biol. Chem., 2004, 279(19):19936-47. Epub Mar. 2, 2004.
Staerk, J., et. al., "JAK1 and Tyk2 activation by the homologous polycythemia vera JAK2 V617F mutation: cross-talk with IGF1 receptor", J Biol Chem., 280:41893-41899 (2005).
State Intellectual Property Office, PR China, Office Action, dated Sep. 3, 2010 Pat. Appl. No. 200680052750.7 (8 pages).
Stirewalt et al., "Predictors of relapse and overall survival in Philadelphia chromosome-positive acute lymphoblastic leukemia after transplantation", Biol Blood Marrow Transplant. Mar. 2003;9(3):206-12.
STN Search conducted Aug. 30, 2010 (17 pages).
STN Search conducted Jun. 24, 2011 (24 pages).
STN Search conducted Nov. 5, 2010 (5 pages).
STN Search conducted Nov. 9, 2010 (43 pages).
STN Search, Nov. 12, 2009 (180 pages).
STN Search, Oct. 20, 2009 (601 pages).
STN Search, Sep. 20, 2009 (864 pages).

(56) References Cited

OTHER PUBLICATIONS

Strassmann et al., "Suramin Interferes with Interleukin-6 Receptor Binding in Vitro and Inhibits Colon-26-mediated Experimental Cancer Cachexia in Vivo," J. Clin. Invest., Nov. 1993, 92: 2152-2159.
Sullivan et al., "4th International Conference on the Lacrimal Gland, Tear Film & Ocular Surface and Dry Eye Syndromes, Nov. 20, 2004" (2 pages).
Symington et al., Transplantation, 1992, 54(3): 457-462.
Swerdlow, et al., WHO Classification of Tumours of Haematopoietic and Lymphoid Tissues. 4th Edition. Lyon France: IARC Press; 2008:88-103.
Santini, et al., PLoS One, 6(8), e23109, pp. 1-8 (2011).
Takahashi, et al., "Solvent-Free Reaction Using Pmospwonium Salts: Chlorination of Hydroxyheteroaromatics and dehydration of Primary Amides", Heterocycles 68: 1973-1979 (2006).
Takano et al , "Inflammatory cells in brush cytology samples correlate with the severity of corneal lesions in atopic keratoconjunctivitis", Br J Ophthalmol, 2004;88:1504-5.
Takemoto, et al. (1997). "Proliferation of adult T cell leukemia/lymphoma cells is associated with the constitutive activation of JAK/STAT proteins." Proc Natl Acad Sci U S A, 94(25): 13897-902.
Tamura et al., "Involvement of Human Interleukin 6 in Experimental Cachexia Induced by a Human Uterine Cervical Carcinoma Xenograft," Clin. Cancer Res., Nov. 1995, 1: 1353-1358.
Tan, et al, "Racemization processes at a quaternary carbon center in the context of the asymmetric Michael reaction", Tetrahedron Lett., 42(30):5021-5023 (2001).
Tang et al., "Knowledge-based design of 7-azaindoles as selective B-Raf inhibitors", Bioorganic & Medicinal Chemistry Letters (2008), 18(16):4610-4614.
Tasian et al., "Understanding the biology of CRLF2-overexpressing acute lymphoblastic leukemia", Critical Reviews in Oncogenesis, (2011) vol. 16, No. 1-2, pp. 13-24.
Tefferi, A. et al. "The Clinical Phenotype of Myelofibrosis Encompasses a Chronic Inflammatory State that is Favorably Altered by INCB018424, A Selective Inhibitor of JAK1/2" Poster #2804 at the American Society of Hematology Annual Meeting (ASH), Dec. 7, 2008, (18 pages).
Tefferi, Ayalew, "Primary myelofibrosis: 2012 update on diagnosis, risk stratification, and management", American Journal of Hematology, (Dec. 2011) vol. 86, No. 12, pp. 1017-1026.
Tefferi, et al., "Serious adverse events during ruxolitinib treatment discontinuation in patients with myelofibrosis", Mayo Clinic Proceedings, (Dec. 2011) vol. 86, No. 12, pp. 1188-1191.
Thompson, J., et al., "Photochemical Preparation of a Pyridone Containing Tetracycle: A Jak Protein Kinase Inhibitor", Bioorganic & Medicinal Chemistry Letters, 12 (2002) 1219-1223.
Tiffany et al., Meniscometry using the Tearscope-plus (ARVO abstract). Invest Ophthalmol Vis Sci, (2001);42, s37 (1 page).
Tiffany, J., "Refractive index of meibomian and other lipids", Curr Eye Res, (1986);5:887-9.
Ting, et al., "The Synthesis of substituted bipiperidine amide compounds as CCR3 antagonists", Bioorg. Med. Chem. Lett., vol. 15, No. 5, 1 (2005) pp. 1375-1378.
Toyonaga, "Blockade of constitutively activated Janus kinase/signal transducer and activator of transcription-3 pathway inhibits growth of human pancreatic cancer", Cancer Lett. 201(1):107-16 (2003).
Trikha et al., "Targeted anti-interleukin-6 monoclonal antibody therapy for cancer: a review of the rationale and clinical evidence," Clinical Cancer Research, 2003, 9: 4653-4665.
Tsubota et al., "Brush cytology for the evaluation of dry-eye", Nippon Ganka Gakkai Zasshi, 1990a ;94:224-30; in Japanese with English abstract.
Tsubota et al., "Conjunctival brush cytology", Acta Cytol, (1990) vol. 34(2):233-5.
Tsubota et al., "Detection by brush cytology of mast cells and eosinophils in allergic and vernal conjunctivitis"; Cornea, (1991) vol. 10(6):525-31.
Ueda et al., "1,2-Benzisoxazol-3-yl Diphenyl Phosphate: A New, Reactive Activating Agent for the Synthesis of Amides, Esters, and Peptides via Condensation", J. Org. Chem. 50:760-763 (1985).
van Best et al., "Measurement of basal tear turnover using a standardized protocol", Graefe's Arch Clin Exp Ophthalmol, 1995; 233:1-7.
van Bijsterveld, O., "Diagnostic tests in the sicca syndrome", Arch Ophthalmol, 1969;82:10-14.
van Rhee et al., "Anti-Interleukin-6 Monoclonal man's Disease," J. Clin. Oncol., 2010, 28(23):3701-3708.
Vaillant et al., "Turbidity of pulpy fruit juice: A key factor for predicting cross-flow microfiltration performance," J Membrane Sci., 2008, 325:404-412.
Vanhoutte, Arthritis Rheum 64.10 (2012): S1051-1.
Vannucchi A. et al., "The mTOR Inhibitor, RAD001, Inhibits the Growth of Cells From Patients with Myeloproliferative Neoplasms", Blood: ASH Annual Meeting Absracts, $51^{st}$ Annual Meeting of the American Society of Hematology, vol. 114, No. 22 (2009) 2 pages.
Vannucchi, A. et al , "Inhibitorsof PI3K/Akt and/or mTOR Inhibit the Growth of Cells of Myeloproliferative Neoplasms and Synergize with JAK2 Inhibitor and Interferon", Blood, vol. 118, No. 21, pp. 1638-1639, XP008150742ASH Annual Meeting Abstract 3835 American Society of Hematology (2011).
Vannucchi, A. et al., "RAD001, An Inhibitor of mTOR, Shows Clinical Activity in a Phase I/II Study in Patients with Primary Myelofibrosis (PMF) and Post Polycythemia Vera/Essential Thrombocythemia Myelofibrosis (PPV/PET MF)", Blood, ASH Annual Meeting Abstracts 307, vol. 114, No. 22 (2009) 2 pages.
Vardiman, et al., Blood 2002;100:2292-2302.
Vardiman, et al., Blood 2009;114:937-951.
Vasilevsky, et al., "Ethyl Vinyl Ether—an Agent for Protection of the Pyrazole NH-Fragment. A Convenient Method for the Preparation of N-Unsubstituted 6Alkynylpyrazoles", Heterocycles, 60(4):879-886 (2003).
Venugopal et al., "Special clinical concerns/problems in the management of MDS and secondary acute myeloid leukemias," Cancer Treat Res, 2001, 108: 257-65.
Verma, et al., "Jak family of kinases in cancer", Cancer and Metastasis Reviews, vol. 22, No. 4, 423-434, DOI: 10.1023/A:1023805715476 (2003).
Verstovsek, "Therapeutic Potential of JAK2 Inhibitors", Hematology Am Soc Hematol Educ Program, 2009:636-42.
Verstovsek, S. et al. "The JAK Inhibitor INCB018424 Demonstrates Durable and Marked Clinical Responses in Primary Myelofibrosis (PMF) and Post-Polycythemia/Essential Thrombocythemia Myelofibrosis (Post-PV/ET-MF)" Poster #1762 at the American Society of Hematology Annual Meeting (ASH), Dec. 6, 2008 (19 pages).
Verstovsek, S. et al. "The selective Janus kinase (JAK) inhibitor, INCB018424, shows efficacy in phase I/II trial in patients with primary myelofibrosis (PMF) and post polycythemia vera/essential thrombocythemia myelofibrosis (Post-PV/ET MF)" Abstract #0444, presented Saturday, Jun. 14, 2008 at the European Hematology Association, 13th Congress, Jun. 12-15, Copenhagen, Denmark (2 pages).
Verstovsek, S. et al. INCB18424, an Oral, Selective JAK2 Inhibitor, Shows Significant Clinical Activity in a Phase I/II Study in Patient with Primary Myelofibrosis (PMF) and Post Polycythemia Vera/Essential Thrombocythemia Myelofibrosis (Post-PV/ET MF), presentation at the American Society of Hematology 49th Annual Meeting and Exposition, Dec. 10, 2007 (16 pages).
Verstovsek, Srdan et al., "Characterization of JAKS V617F Allele Burden in Advanced Myelofibrosis (MF) Patients: No Change in V617F:WT JAK2 Ratio in Patients with High Allele Burdens despite Profound Clinical Improvement Following Treatment with the JAKL Inhibitor, INCB018424,"50th ASH Annual Meeting and Exposition, Abstract No. 2802 (2008).
Verstovsek, et al., Blood (ASH Annual Meeting Abstracts) 2007 110: Abstract 558.
Verstovsek, et al., Blood (ASH Annual Meeting Abstracts) 2009 114: Abstract 311.

(56) References Cited

OTHER PUBLICATIONS

Verstovsek, et al., Blood (ASH Annual Meeting Abstracts) 2010 116: Abstract 313.
Vitali et al. "The European Community Study Group on diagnostic criteria for Sjogren's syndrome. Sensitivity and specificity of tests for ocular and oral involvement in Sjogren's syndrome." 1994; Ann Rheum Dis, 53(10): 637-47.
Wagh, et al., "Polymers used in ocular dosage form and drug delivery systems", Asian J. Pharm., pp. 12-17 (Jan. 2008).
WebMD. "Diabetes Health Center." Available at: < http.//diabetes. webmd.com/guide/diabetestreatment_care >. 3 pages, retrieved from the Internet May 28, 2013.
Webster's New World Medical Dictionary, Sjogren's syndrome, 2003, Wiley Publishing, printed fro http://www.credoreference. com/entry/webstermed/sjogren_s_syndrome, 2 pages.
Weiss, et al., "Evaluation of a Series of Naphthamides as Potent, Orally Active Vascular Endothelial Growth Factor Receptor-2 Tyrosine Kinase Inhibitors", J. Med Chem., 51:1668-1680 (2008).
Welch et al., "An approach to a more standardized method of evaluating tear film break-up time", Invest Ophthalmol Vis Sci, 2003; 2485/B324 (abstract only—2 pages).
White et al., "Human basic tear fluid osmolality. I. Importance of sample collection strategy", Acta Ophthalmol (Copenh), Aug;71(4):524-9, 1993.
Williams et al., "Carbodiimide Chemistry: Recent Advances", Chem. Rev. 81:589-636 (1981).
Williams, et al. "Initial Efficacy of INCB018424, a selective Janus Kinase1& 2 (JAK1&2) Inhibitor in Rheumatoid Arthritis (RA)," European League Against Rheumatism (EULAR) meeting presentation and abstract (Jun. 11-14, 2008, Paris, France). Annals Rheum Dis 67SII:62, 2008.
Wolf, et al., "Burger's Medicinal Chemistry and Drug Discovery", 5th Ed. Part I, pp. 975-977 (1995).
Wu et al., One-Pot Two-Step Microwave-Assisted Reaction in Construction 4,5-Disubstituted Pyrazolopyrimidines Organic Letters, 2003, 5(20), 3587-3590.
Ling et al., "Knockdown of STAT3 Expression by RNA Interference Inhibits the Induction of Breast Tumors in Immunocompetent Mice", Cancer Res Apr. 1, 2005 65; 2532.
Xiong, "Inhibition of JAK1, 2/STAT3 Signaling Induces Apoptosis, Cell Cycle Arrest, and Reduces Tumor Cell Invasion in Colorectal Cancer Cells," Neoplasia, Mar. 2008, 10(3): 287-297.
Yamamura et al., "Circulating interleukin-6 levels are elevated in adult T-cell leukaemia/lymphoma patients and correlate with adverse clinical features and survival," Br. J. Haematol., 1998, 100: 129-134.
Yamaoka et al., "Janus kinase (JAK) inhibitors in rheumatoid arthritis", Current Rheumatology Reviews, (Nov. 2011) vol. 7, No. 4, pp. 306-312.
Yang et al., "Constitutive NF-kB activation confers interleukin 6 (IL6) independence and resistance to dexamethasone and Janus kinase inhibitor INCB018424 in murine plasmacytoma cells", Journal of Biological Chemistry, (Aug. 12, 2011) vol. 286, No. 32, pp. 27988-27997.
Yao, et al. "Glucocorticoid-Induced Bone Loss in Mice Can Be Reversed by the Actions of Parathyroid Hormone and Risedronate on Different Pathways for Bone Formation and Mineralization", Arthritis and Rheumatism, 58(11):3485-3497 (2008).
Yao, et al., "Glucocorticoid Excess in Mice Results in Early Activation of Osteoclastogenesis and Adipogenesis and Prolonged Suppression of Osteogenesis", Arthritis and Rheumatism, 58(6), 1674-1686 (2008).
Li et al., "The synthesis and the antitumor activity of 5,7-disubstituted pyrazolo [1,5-a] pyrimidines," . Chinese J Med Chem., Feb. 28, 2007, 17(1):18-22.
Yokoi et al., "A newly developed video-meibography system featuring a newly designed probe", Jpn J Ophthalmol, 2007; 51: 53-6).
Yokoi et al., "Assessment of meibomian gland function in dry eye using meibometry", Arch Ophthalmol, 1999;117:723-9).
Yokoi et al., "Correlation of tear lipid layer interference patterns with the diagnosis and severity of dry eye", Am J Ophthalmol, 1996;122:818-24.
Yokoi et al., "Non-invasive methods of assessing the tear film", Exp Eye Res, 2004;78:399-407).
Mao et al., "Advances in research of tyrosine kinases inhibitor of vascular endothelial growth factor receptor," Chinese J New Drugs, Dec. 31, 2008, 17(7):544-550.
Younes, J. Clin. Oncol., 30(33):1461-1467 (2012).
Yu, et al., "Constitutive activation of the Janus kinase-STAT pathway in T lymphoma overexpressing the Lck protein tyrosine kinase", J Immunol. 159(11):5206-10 (1997).
Zheng, et al., "Discovery of INCB108201PF-4178903, a potent, selective, and orally bioavailable dual CCR2 and CCR5 antagonist", Bioorganic & Medicinal Chemistry Letters 21 (2011) 1442-45.
Zoppellaro, et al., "A Multifunctional High-Spin Bimdical Pyrazolylbipyridine-bisnitronylnitroxide", Org. Lett. 6(26):4929-4932 (2004).
Zou, et al., "Signaling Pathways Activated by Oncogenic Forms of Abl Tyrosine Kinase " Journal of Biological Chemistry, 274(26):18141-18144, 1999.

\* cited by examiner

SUSTAINED RELEASE DOSAGE FORMS FOR A JAK1 INHIBITOR

This application claims the benefit of priority of U.S. Prov. Appl. No. 61/863,325, filed Aug. 7, 2013, and U.S. Prov. Appl. No. 61/913,066, filed Dec. 6, 2013, each of which is incorporated herein by reference in its entirety.

TECHNICAL FIELD

This application relates to a sustained release dosage form comprising {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or a pharmaceutically acceptable salt thereof, and doses and methods related thereto.

BACKGROUND

Protein kinases (PKs) regulate diverse biological processes including cell growth, survival, differentiation, organ formation, morphogenesis, neovascularization, tissue repair, and regeneration, among others. Protein kinases also play specialized roles in a host of human diseases including cancer. Cytokines, low-molecular weight polypeptides or glycoproteins, regulate many pathways involved in the host inflammatory response to sepsis. Cytokines influence cell differentiation, proliferation and activation, and can modulate both pro-inflammatory and anti-inflammatory responses to allow the host to react appropriately to pathogens. Signaling of a wide range of cytokines involves the Janus kinase family (JAKs) of protein tyrosine kinases and Signal Transducers and Activators of Transcription (STATs). There are four known mammalian JAKs: JAK1 (Janus kinase-1), JAK2, JAK3 (also known as Janus kinase, leukocyte; JAKL; and L-JAK), and TYK2 (protein-tyrosine kinase 2).

Cytokine-stimulated immune and inflammatory responses contribute to pathogenesis of diseases: pathologies such as severe combined immunodeficiency (SCID) arise from suppression of the immune system, while a hyperactive or inappropriate immune/inflammatory response contributes to the pathology of autoimmune diseases (e.g., asthma, systemic lupus erythematosus, thyroiditis, myocarditis), and illnesses such as scleroderma and osteoarthritis (Ortmann, R. A., T. Cheng, et al. (2000) *Arthritis Res* 2(1): 16-32).

Deficiencies in expression of JAKs are associated with many disease states. For example, Jak1–/– mice are runted at birth, fail to nurse, and die perinatally (Rodig, S. J., M. A. Meraz, et al. (1998) *Cell* 93(3): 373-83). Jak2–/– mouse embryos are anemic and die around day 12.5 postcoitum due to the absence of definitive erythropoiesis.

The JAK/STAT pathway, and in particular all four JAKs, are believed to play a role in the pathogenesis of asthmatic response, chronic obstructive pulmonary disease, bronchitis, and other related inflammatory diseases of the lower respiratory tract. Multiple cytokines that signal through JAKs have been linked to inflammatory diseases/conditions of the upper respiratory tract, such as those affecting the nose and sinuses (e.g., rhinitis and sinusitis) whether classically allergic reactions or not. The JAK/STAT pathway has also been implicated in inflammatory diseases/conditions of the eye and chronic allergic responses.

Activation of JAK/STAT in cancers may occur by cytokine stimulation (e.g. IL-6 or GM-CSF) or by a reduction in the endogenous suppressors of JAK signaling such as SOCS (suppressor or cytokine signaling) or PIAS (protein inhibitor of activated STAT) (Boudny, V., and Kovarik, J., *Neoplasm*. 49:349-355, 2002). Activation of STAT signaling, as well as other pathways downstream of JAKs (e.g., Akt), has been correlated with poor prognosis in many cancer types (Bowman, T., et al. *Oncogene* 19:2474-2488, 2000). Elevated levels of circulating cytokines that signal through JAK/STAT play a causal role in cachexia and/or chronic fatigue. As such, JAK inhibition may be beneficial to cancer patients for reasons that extend beyond potential anti-tumor activity.

JAK2 tyrosine kinase can be beneficial for patients with myeloproliferative disorders, e.g., polycythemia vera (PV), essential thrombocythemia (ET), myeloid metaplasia with myelofibrosis (MMM) (Levin, et al., *Cancer Cell*, vol. 7, 2005: 387-397). Inhibition of the JAK2V617F kinase decreases proliferation of hematopoietic cells, suggesting JAK2 as a potential target for pharmacologic inhibition in patients with PV, ET, and MMM.

Inhibition of the JAKs may benefit patients suffering from skin immune disorders such as psoriasis, and skin sensitization. The maintenance of psoriasis is believed to depend on a number of inflammatory cytokines in addition to various chemokines and growth factors (JCI, 113:1664-1675), many of which signal through JAKs (*Adv Pharmacol*. 2000; 47:113-74).

Due to the usefulness of compounds which inhibit JAK in targeting augmentation or suppression of the immune and inflammatory pathways (such as immunosuppressive agents for organ transplants), as well as the treatment of autoimmune diseases, diseases involving a hyperactive inflammatory response (e.g., eczema), allergies, cancer (e.g., prostate, leukemia, multiple myeloma), and some immune reactions (e.g., skin rash or contact dermatitis or diarrhea) caused by other therapeutics, there is a need for improved formulations for administering JAK kinases. The dosages forms described herein, as well as the doses and methods described supra are directed toward this need and other ends.

SUMMARY

JAK inhibitors are described in U.S. Ser. No. 13/043,986 (US 2011/0224190), filed Mar. 9, 2011, which is incorporated herein by reference in its entirety, including {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, which is depicted below as Formula I.

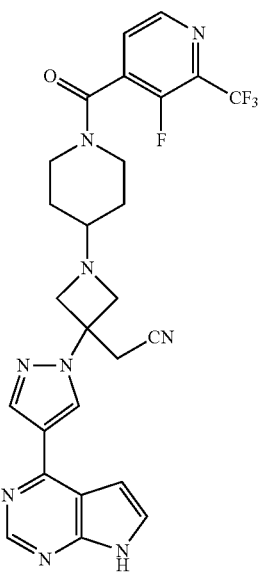

The present application provides, inter alia, sustained-release dosage forms comprising about 25 mg to about 600 mg (e.g., 25 mg, 100 mg, 200 mg, 300 mg, or 600 mg) on a free base basis of {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or a pharmaceutically acceptable salt thereof.

The present invention further provides one or more sustained release dosage forms each comprising {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or a pharmaceutically acceptable salt thereof wherein said one or more sustained release dosage forms together provide a once-daily oral dosage of about 400 mg to about 600 mg on a free base basis of {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or a pharmaceutically acceptable salt thereof, to a patient.

The present invention also provides a dose, comprising one or more sustained release dosage forms each comprising {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or a pharmaceutically acceptable salt thereof wherein said dose provides a once-daily oral dosage of about 400 mg to about 600 mg on a free base basis of {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or a pharmaceutically acceptable salt thereof, to a patient.

The present application further provides one or more sustained release dosage forms as described herein, which together provide a once-daily oral dosage of about 600 mg on a free base basis of {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or a pharmaceutically acceptable salt thereof, to a patient.

The present application also provides a dose comprising one or more sustained release dosage forms as described herein, which together provide a once-daily oral dosage of about 600 mg on a free base basis of {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or a pharmaceutically acceptable salt thereof, to a patient.

The present application further provides methods of treating an autoimmune disease, a cancer, a myeloproliferative disorder, an inflammatory disease, a bone resorption disease, or organ transplant rejection in a patient in need thereof, comprising orally administering to said patient one or more sustained release dosage forms as described herein.

The present application also provides methods of treating an autoimmune disease, a cancer, a myeloproliferative disorder, an inflammatory disease, a bone resorption disease, or organ transplant rejection in a patient in need thereof, comprising orally administering to said patient a once-daily dose of about 400 mg to about 600 mg on a free base basis of {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or a pharmaceutically acceptable salt thereof, wherein the dose comprises one or more sustained release dosage forms each comprising {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or a pharmaceutically acceptable salt thereof.

The present application further provides methods of treating an autoimmune disease, a cancer, a myeloproliferative disorder, an inflammatory disease, a bone resorption disease, or organ transplant rejection in a patient in need thereof, comprising orally administering to said patient one or more sustained release dosage as described herein.

The present application also provides methods of treating an autoimmune disease, a cancer, a myeloproliferative disorder, an inflammatory disease, a bone resorption disease, or organ transplant rejection in a patient in need thereof, wherein the method comprises orally administering to said patient the one or more sustained release dosage forms as a once-daily dosage of about 600 mg on a free base basis of {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or a pharmaceutically acceptable salt thereof.

DESCRIPTION OF DRAWINGS

FIG. 4(b) as a function of total average concentration (Cavg)).

DETAILED DESCRIPTION

Figure 1A:
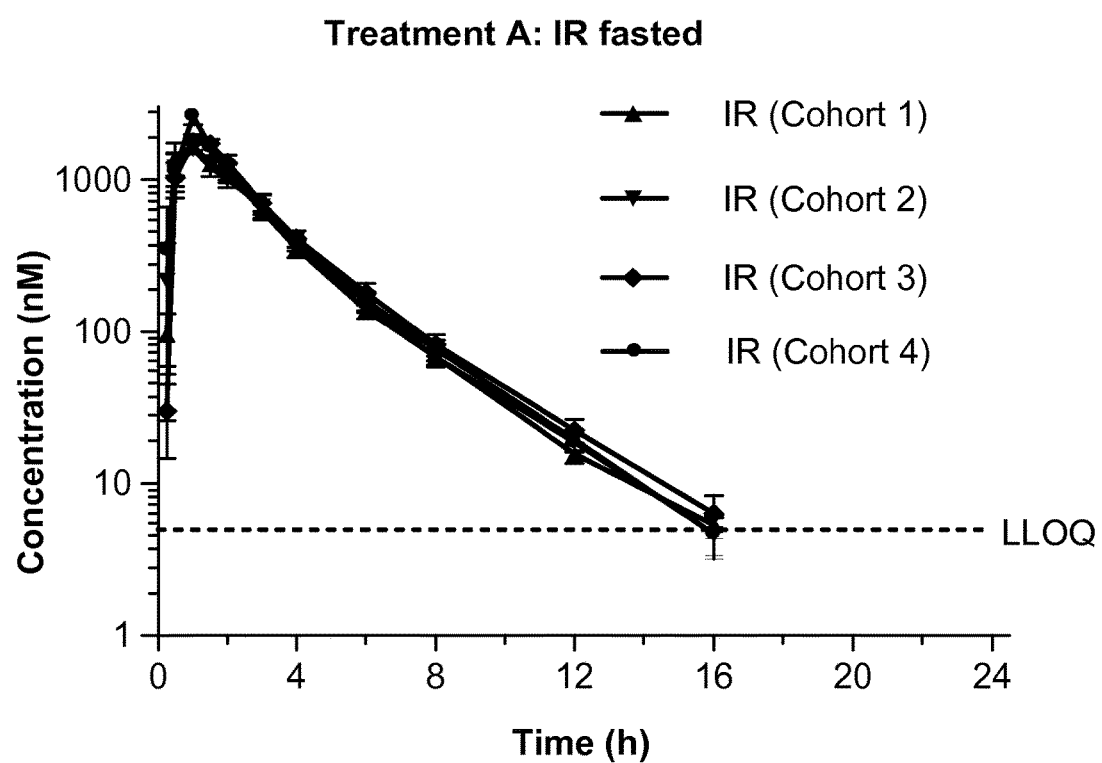
FIG. 1A-C depicts plasma concentrations for the compound of Formula I (Mean±SE) in healthy subjects receiving single doses of 300 mg IR capsules (1A: Cohorts 1-4, fasted), SR1, SR2, SR3, and SR4 tablets (2B: Cohorts 1-4, fasted; and 2C: Cohorts 1-4, fed a high-fat meal).

The present application provides sustained-release dosage forms comprising {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or a pharmaceutically acceptable salt thereof. In some embodiments, the present application provides a sustained-release dosage form comprising about 25 mg to about 600 mg on a free base basis of {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or a pharmaceutically acceptable salt thereof.

In some embodiments, the sustained-release dosage form comprises about 300 mg on a free base basis of {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or a pharmaceutically acceptable salt thereof.

In some embodiments, the sustained-release dosage form comprises about 200 mg on a free base basis of {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or a pharmaceutically acceptable salt thereof.

In some embodiments, the sustained-release dosage form comprises about 100 mg on a free base basis of {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or a pharmaceutically acceptable salt thereof.

In some embodiments, the sustained-release dosage form comprises about 300 mg on a free base basis of {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile adipic acid salt.

In some embodiments, the sustained-release dosage form comprises about 200 mg on a free base basis of {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile adipic acid salt.

In some embodiments, the sustained-release dosage form comprises about 100 mg on a free base basis of {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile adipic acid salt.

In some embodiments of the sustained-release dosage form comprising about 100 mg, oral administration of three of said dosage forms to a fasted individual provides a mean peak plasma concentration ($C_{max}$) of {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile of about 100 nM to about 1000 nM. As used in this context, oral administration means that a single dose is administered to the individual (in this case, 3×100 mg) and the PK parameter is calculated from the measurements of plasma concentration over time. In this context, the PK parameter (in this case, $C_{max}$) is being used to characterize the single sustained release dosage form (i.e., the claims are directed to a single dosage form, not three dosage forms).

In some embodiments of the sustained-release dosage form comprising about 100 mg, oral administration of three of said dosage forms to a fasted individual provides a mean peak plasma concentration ($C_{max}$) of {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile of about 400 nM to about 700 nM.

In some embodiments of the sustained-release dosage form comprising about 100 mg, oral administration of three of said dosage forms to a fasted individual provides a mean time to peak plasma concentration ($T_{max}$) of {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile of about 0.5 hours to about 3 hours.

In some embodiments of the sustained-release dosage form comprising about 100 mg, oral administration of three of said dosage forms to a fasted individual provides a mean time to peak plasma concentration ($T_{max}$) of {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile of at least 0.5 hours.

In some embodiments of the sustained-release dosage form comprising about 100 mg, oral administration of three of said dosage forms to a fasted individual provides a ratio of mean peak plasma concentration ($C_{max}$) to mean 12-hour plasma concentration ($C_{12h}$) of {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile of about 5 to about 50.

In some embodiments of the sustained-release dosage form comprising about 100 mg, oral administration of three of said dosage forms to a fasted individual provides a ratio of mean peak plasma concentration ($C_{max}$) to mean 12-hour plasma concentration ($C_{12h}$) of {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile of about 9 to about 40.

In some embodiments of the sustained-release dosage form comprising about 100 mg, oral administration of three of said dosage forms to a fasted individual provides a ratio of mean peak plasma concentration ($C_{max}$) to mean 12-hour plasma concentration ($C_{12h}$) of {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile of about 15 to about 30.

In some embodiments of the sustained-release dosage form comprising about 100 mg, oral administration of three of said dosage forms to a fasted individual provides a mean half-life ($t_{1/2}$) of {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile of about 5 hours to about 15 hours.

In some embodiments of the sustained-release dosage form comprising about 100 mg, oral administration of three of said dosage forms to a fasted individual provides a mean half-life ($t_{1/2}$) of {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile of about 7 hours to about 12 hours.

In some embodiments of the sustained-release dosage form comprising about 100 mg, oral administration of three of said dosage forms to a fasted individual provides a mean half-life ($t_{1/2}$) of {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile of about 1 hour to about 20 hours.

In some embodiments of the sustained-release dosage form comprising about 100 mg, oral administration of three of said dosage forms to a fasted individual provides a mean bioavailability ($AUC_{0-\infty}$) of {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile of about 1000 nM*h to about 4000 nM*h.

In some embodiments of the sustained-release dosage form comprising about 100 mg, oral administration of three of said dosage forms to a fasted individual provides a mean bioavailability ($AUC_{0-\infty}$) of {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile of about 1500 nM*h to about 3100 nM*h.

In some embodiments of the sustained-release dosage form comprising about 100 mg, oral administration of three of said dosage forms to an individual after a high-fat meal provides a mean peak plasma concentration ($C_{max}$) of {1-{1-[3-fluoro-2-(trifluoromethyl)isonicotinoyl]piperidin-4-yl}-

3-[4-(7H-pyrrolo[2,3-d]pyrimidin-4-yl)-1H-pyrazol-1-yl]azetidin-3-yl}acetonitrile of about 200 nM to about 2000 nM.

In some embodiments of the sustained-release dosage form comprising about 100 mg, oral administration of three of said dosage forms to an individual after a high-fat meal provides a mean peak plasma concentration ($C_{max}$) of {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile of about 500 nM to about 1500 nM.

In some embodiments of the sustained-release dosage form comprising about 100 mg, oral administration of three of said dosage forms to an individual after a high-fat meal provides a mean time to peak plasma concentration ($T_{max}$) of {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile of about 1 hour to about 9 hours.

In some embodiments of the sustained-release dosage form comprising about 100 mg, oral administration of three of said dosage forms to an individual after a high-fat meal provides a mean time to peak plasma concentration ($T_{max}$) of {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile of at least 1.5 hours.

In some embodiments of the sustained-release dosage form comprising about 100 mg, oral administration of three of said dosage forms to an individual after a high-fat meal provides a ratio of mean peak plasma concentration ($C_{max}$) to mean 12-hour plasma concentration ($C_{12h}$) of {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile of about 10 to about 70.

In some embodiments of the sustained-release dosage form comprising about 100 mg, oral administration of three of said dosage forms to an individual after a high-fat meal provides a ratio of mean peak plasma concentration ($C_{max}$) to mean 12-hour plasma concentration ($C_{12h}$) of {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile of about 15 to about 50.

In some embodiments of the sustained-release dosage form comprising about 100 mg, oral administration of three of said dosage forms to an individual after a high-fat meal provides a ratio of mean peak plasma concentration ($C_{max}$) to mean 12-hour plasma concentration ($C_{12h}$) of {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile of about 25 to about 45.

In some embodiments of the sustained-release dosage form comprising about 100 mg, oral administration of three of said dosage forms to an individual after a high-fat meal provides a mean half-life ($t_{1/2}$) of {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile of about 1 hour to about 7 hours.

In some embodiments of the sustained-release dosage form comprising about 100 mg, oral administration of three of said dosage forms to an individual after a high-fat meal provides a mean half-life ($t_{1/2}$) of {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile of about 2 hours to about 5 hours.

In some embodiments of the sustained-release dosage form comprising about 100 mg, oral administration of three of said dosage forms to an individual after a high-fat meal provides a mean bioavailability ($AUC_{0-\infty}$) of {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile of about 2000 nM*h to about 5000 nM*h.

In some embodiments of the sustained-release dosage form comprising about 100 mg, oral administration of three of said dosage forms to an individual after a high-fat meal provides a mean bioavailability ($AUC_{0-\infty}$) of {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile of about 3000 nM*h to about 4000 nM*h.

In some embodiments, the percent geometric mean ratio of the sustained release dosage form relative to an immediate release dosage form for $C_{max}$ is about 15% to about 30%, wherein one or more immediate release dosage forms and one or more sustained release dosage forms are independently orally administered to fasted individuals as a single dose, wherein the same size dose of {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or a pharmaceutically acceptable salt, is administered.

In some embodiments, the percent geometric mean ratio of the sustained release dosage form relative to an immediate release dosage form for $C_{max}$ is about 15% to about 30%, wherein one or more immediate release dosage forms and one or more sustained release dosage forms are independently orally administered to fasted individuals as a single dose, wherein the same size dose of {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or a pharmaceutically acceptable salt, is administered.

In some embodiments, the percent geometric mean ratio of the sustained release dosage form relative to an immediate release dosage form for $AUC_{0-\infty}$ is about 40% to about 55%, wherein one or more immediate release dosage forms and one or more sustained release dosage forms are independently orally administered to fasted individuals as a single dose, wherein the same size dose of {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or a pharmaceutically acceptable salt, is administered.

In some embodiments, the percent geometric mean ratio for $C_{max}$ of the sustained release dosage form orally administered to an individual after a high-fat meal relative to the sustained release dosage form orally administered to a fasted individual is about 150% to about 250%.

In some embodiments, the percent geometric mean ratio for $AUC_{0-\infty}$ of the sustained release dosage form orally administered to an individual after a high-fat meal relative to the sustained release dosage form orally administered to a fasted individual is about 125% to about 170%.

In some embodiments, the sustained-release dosage forms of the invention may include a sustained-release matrix former. Example sustained-release matrix formers include cellulosic ethers such as hydroxypropyl methylcellulose (HPMC, hypromellose) which is a high viscosity polymer, and methyl celluloses. Example hydroxypropyl methylcelluloses include Methocel™ K15M, Methocel™ K4M, Methocel™ K100LV, Methocel™ E3, Methocel™ E5, Methocel™ E6, Methocel™ E15, Methocel™ E50, Methocel™ E10M, Methocel™ E4M, and Methocel™ E10M. In some embodiments, the sustained release dosage form comprises one or more hypromelloses. In some embodiments, the sustained release dosage form comprises a first hypromellose characterized by having an apparent viscosity at a concentration of 2% in water of about 80 cP to about 120 cP and a second hypromellose characterized by having an apparent viscosity at a concentration of 2% in water of about 3000 cP to about 5600 cP. In some embodiments, the sustained release dosage form comprises about 8% to about 20% by weight of one or more hypromelloses. In some embodiments, the sustained release dosage form comprises about 10% to about 15% by weight of one or more hypromelloses.

In some embodiments, the sustained-release dosage forms of the invention can further include one or more fillers, glidants, disintegrants, binders, or lubricants as inactive ingredients. In some embodiments, the filler comprises microcrystalline cellulose, lactose monohydrate, or both. In some embodiments, the sustained release dosage form comprises about 16% to about 22% by weight of microcrystalline cellulose. In some embodiments, the sustained release dosage form comprises about 45% to about 55% by weight of lactose monohydrate.

In some embodiments, lubricants can be present in the dosage forms of the invention in an amount of 0 to about 5% by weight. Non-limiting examples of lubricants include magnesium stearate, stearic acid (stearin), hydrogenated oil, polyethylene glycol, sodium stearyl fumarate, and glyceryl behenate. In some embodiments, the formulations include magnesium stearate, stearic acid, or both. In some embodiments, the sustained release dosage form comprises about 0.3% to about 0.7% by weight of magnesium stearate.

In some embodiments, glidants may be present in the dosage forms. In some embodiments, glidants can be present in the dosage forms of the invention in an amount of 0 to about 5% by weight. Non-limiting examples of glidants include talc, colloidal silicon dioxide, and cornstarch. In some embodiments, the glidant is colloidal silicon dioxide.

In some embodiments, film-coating agents can be present in an amount of 0 to about 5% by weight. Non-limiting illustrative examples of film-coating agents include hypromellose or polyvinyl alcohol based coating with titanium dioxide, talc and optionally colorants available in several commercially available complete coating systems.

In some embodiments, the sustained release dosage form comprises pregelatinized starch.

In some embodiments, the sustained release dosage form is a tablet.

In some embodiments, the sustained release dosage form is prepared by process comprising wet granulation.

In some embodiments, the sustained release dosage form comprises one or more excipients independently selected from hypromelloses and microcrystalline celluloses.

In some embodiments, the sustained release dosage form comprises one or more excipients independently selected from hypromelloses, microcrystalline celluloses, magnesium stearate, lactose, and lactose monohydrate.

In some embodiments, the sustained release dosage form comprises one or more excipients independently selected from hypromelloses, microcrystalline celluloses, magnesium stearate, lactose, lactose monohydrate, and pregelatinized starch.

The present invention further provides one or more sustained release dosage forms each comprising {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or a pharmaceutically acceptable salt thereof; wherein said one or more sustained release dosage forms together provide a once-daily oral dosage of about 400 mg to about 600 mg on a free base basis of {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or a pharmaceutically acceptable salt thereof, to a patient.

The present invention also provides a dose, comprising one or more sustained release dosage forms each comprising {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or a pharmaceutically acceptable salt thereof; wherein said dose provides a once-daily oral dosage of about 400 mg to about 600 mg on a free base basis of {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or a pharmaceutically acceptable salt thereof, to a patient.

The present application further provides one or more sustained release dosage forms as described herein, which together provide a once-daily oral dosage of about 600 mg on a free base basis of {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or a pharmaceutically acceptable salt thereof, to a patient.

The present application further provides one or more sustained release dosage forms as described herein, which together provide a once-daily oral dosage of about 500 mg on a free base basis of {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or a pharmaceutically acceptable salt thereof, to a patient.

The present application further provides one or more sustained release dosage forms as described herein, which together provide a once-daily oral dosage of about 400 mg on a free base basis of {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or a pharmaceutically acceptable salt thereof, to a patient.

In some embodiments, the one or more sustained release dosage forms are six dosage forms of about 100 mg on a free base basis of {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or a pharmaceutically acceptable salt thereof, are provided. In some embodiments, the one or more sustained release dosage forms are three dosage forms of about 200 mg on a free base basis of {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or a pharmaceutically acceptable salt thereof, are provided. In some embodiments, the one or more sustained release dosage forms are two dosage forms of about 300 mg on a free base basis of {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or a pharmaceutically acceptable salt thereof, are provided. In some embodiments, the one or more sustained release dosage forms is one dosage form of about 600 mg on a free base basis of {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or a pharmaceutically acceptable salt thereof, is provided.

The present application also provides a dose comprising one or more sustained release dosage forms as described herein, which provide a once-daily oral dosage of about 600 mg on a free base basis of {1-{1-[3-fluoro-2-(trifluoromethyl)isonicotinoyl]piperidin-4-yl}-3-[4-(7H-pyrrolo[2,3-d]

pyrimidin-4-yl)-1H-pyrazol-1-yl]azetidin-3-yl}acetonitrile, or a pharmaceutically acceptable salt thereof, to a patient.

The present application also provides a dose comprising one or more sustained release dosage forms as described herein, which provide a once-daily oral dosage of about 500 mg on a free base basis of {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or a pharmaceutically acceptable salt thereof, to a patient.

The present application also provides a dose comprising one or more sustained release dosage forms as described herein, which provide a once-daily oral dosage of about 400 mg on a free base basis of {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or a pharmaceutically acceptable salt thereof, to a patient.

In some embodiments, the dose comprises six dosage forms of about 100 mg on a free base basis of {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or a pharmaceutically acceptable salt thereof. In some embodiments, the dose comprises three dosage forms of about 200 mg on a free base basis of {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or a pharmaceutically acceptable salt thereof. In some embodiments, the dose comprises two dosage forms of about 300 mg on a free base basis of {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or a pharmaceutically acceptable salt thereof. In some embodiments, the dose comprises one dosage form of about 600 mg on a free base basis of {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or a pharmaceutically acceptable salt thereof.

The present application further provides a kit comprising one or more sustained release dosage forms as described herein, which together provide a once-daily oral dosage of about 400 mg to about 600 mg on a free base basis of {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or a pharmaceutically acceptable salt thereof, to a patient. In some embodiments, the kit further comprises an instruction to administer the one or more sustained release dosage forms as a once-daily dose of about 400 mg to about 600 mg on a free base basis of {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or a pharmaceutically acceptable salt thereof.

The present application further provides a kit comprising one or more sustained release dosage forms as described herein, which together provide a once-daily oral dosage of about 600 mg on a free base basis of {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or a pharmaceutically acceptable salt thereof, to a patient. In some embodiments, the kit further comprises an instruction to administer the one or more sustained release dosage forms as a once-daily dose of about 600 mg on a free base basis of {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or a pharmaceutically acceptable salt thereof.

The present application further provides a kit comprising one or more sustained release dosage forms as described herein, which together provide a once-daily oral dosage of about 500 mg on a free base basis of {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or a pharmaceutically acceptable salt thereof, to a patient. In some embodiments, the kit further comprises an instruction to administer the one or more sustained release dosage forms as a once-daily dose of about 600 mg on a free base basis of {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or a pharmaceutically acceptable salt thereof.

The present application further provides a kit comprising one or more sustained release dosage forms as described herein, which together provide a once-daily oral dosage of about 400 mg on a free base basis of {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or a pharmaceutically acceptable salt thereof, to a patient. In some embodiments, the kit further comprises an instruction to administer the one or more sustained release dosage forms as a once-daily dose of about 600 mg on a free base basis of {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or a pharmaceutically acceptable salt thereof.

In some embodiments, the kit comprises six dosage forms of about 100 mg on a free base basis of {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or a pharmaceutically acceptable salt thereof. In some embodiments, the kit comprises three dosage forms of about 200 mg on a free base basis of {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or a pharmaceutically acceptable salt thereof. In some embodiments, the kit comprises two dosage forms of about 300 mg on a free base basis of {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or a pharmaceutically acceptable salt thereof. In some embodiments, the kit comprises one dosage form of about 600 mg on a free base basis of {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or a pharmaceutically acceptable salt thereof.

As used herein, "sustained-release" is used as generally understood in the art and refers to a formulation designed to slowly release the active ingredient into a patient after oral administration.

As used herein, "dose" refers to the total amount of the compound of Formula I orally administered to the individual or patient. The dose may be in a single dosage form, or a plurality of dosage forms (e.g., a 600 mg dose may be one 600 mg dosage form, two 300 mg dosage forms, three 200 mg dosage forms, six 100 mg dosage forms, etc.). Hence, a dose can refer to a plurality of pills to be taken by a patient at nearly simultaneously.

As used herein, "a fasted individual" means an individual who has fasted for at least 10 hours prior to administration of the dose.

As used herein, "mean" when preceding a pharmacokinetic value (e.g. mean $C_{max}$) represents the arithmetic mean value of the pharmacokinetic value taken from a population of patients unless otherwise specified.

As used herein, "$C_{max}$" means the maximum observed plasma concentration.

As used herein, "$C_{12h}$" refers to the plasma concentration measured at 12 hours from administration.

As used herein, "$T_{max}$" refers to the time at which the maximum blood plasma concentration is observed.

As used herein, "$T_{1/2}$" refers to the time at which the plasma concentration is half of the observed maximum.

As used herein, "AUC" refers to the area under the plasma concentration-time curve which is a measure of total bioavailability.

As used herein, "$AUC_{0-\infty}$" refers to the area under the plasma concentration-time curve extrapolated to infinity.

As used herein, "$AUC_{0-t}$" refers to the area under the plasma concentration-time curve from time 0 to the last time point with a quantifiable plasma concentration, usually about 12-36 hours.

As used herein, "$AUC_{0-\tau}$" refers to the area under the plasma concentration-time curve from time 0 to the time of the next dose.

As used herein, "Cl/F" refers to oral clearance.

The present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol, or butanol) or acetonitrile (ACN) are preferred. Lists of suitable salts are found in *Remington's Pharmaceutical Sciences*, 17th ed., Mack Publishing Company, Easton, Pa., 1985, p. 1418 and *Journal of Pharmaceutical Science*, 66, 2 (1977), each of which is incorporated herein by reference in its entirety. In some embodiments, the compounds described herein include the N-oxide forms.

Methods

The present application further provides methods of treating an autoimmune disease, a cancer, a myeloproliferative disorder, an inflammatory disease, a bone resorption disease, or organ transplant rejection in a patient in need thereof, comprising orally administering to said patient one or more sustained release dosage forms as described herein.

The present application also provides a method of treating an autoimmune disease, a cancer, a myeloproliferative disorder, an inflammatory disease, a bone resorption disease, or organ transplant rejection in a patient in need thereof, comprising orally administering to said patient a once-daily dose of about 400 mg to about 600 mg on a free base basis of {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or a pharmaceutically acceptable salt thereof, wherein the dose comprises one or more sustained release dosage forms each comprising {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or a pharmaceutically acceptable salt thereof.

The present application further provides a method of treating an autoimmune disease, a cancer, a myeloproliferative disorder, an inflammatory disease, a bone resorption disease, or organ transplant rejection in a patient in need thereof, comprising orally administering to said patient one or more sustained release dosage as described herein.

The present application also provides a method of treating an autoimmune disease, a cancer, a myeloproliferative disorder, an inflammatory disease, a bone resorption disease, or organ transplant rejection in a patient in need thereof, wherein the method comprises orally administering to said patient the one or more sustained release dosage forms as a once-daily dosage of about 600 mg on a free base basis of {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or a pharmaceutically acceptable salt thereof.

The present application also provides a method of treating an autoimmune disease, a cancer, a myeloproliferative disorder, an inflammatory disease, a bone resorption disease, or organ transplant rejection in a patient in need thereof, wherein the method comprises orally administering to said patient the one or more sustained release dosage forms as a once-daily dosage of about 500 mg on a free base basis of {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or a pharmaceutically acceptable salt thereof.

The present application also provides a method of treating an autoimmune disease, a cancer, a myeloproliferative disorder, an inflammatory disease, a bone resorption disease, or organ transplant rejection in a patient in need thereof, wherein the method comprises orally administering to said patient the one or more sustained release dosage forms as a once-daily dosage of about 400 mg on a free base basis of {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or a pharmaceutically acceptable salt thereof.

In some embodiments of the methods in the preceding three paragraphs, the one or more sustained release dosage forms are six dosage forms of about 100 mg on a free base basis of {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or a pharmaceutically acceptable salt thereof, are provided. In some embodiments of the methods in the preceding three paragraphs, the one or more sustained release dosage forms are three dosage forms of about 200 mg on a free base basis of {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or a pharmaceutically acceptable salt thereof, are provided. In some embodiments of the methods in the preceding three paragraphs, the one or more sustained release dosage forms are two dosage forms of about 300 mg on a free base basis of {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or a pharmaceutically acceptable salt thereof, are provided. In some embodiments of the methods in the preceding three paragraphs, the one or more sustained release dosage forms is one dosage form of about 600 mg on a free base basis of {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or a pharmaceutically acceptable salt thereof, is provided.

In some embodiments, oral administration of one or more sustained release dosage forms to a fasted individual provides a mean time to peak plasma concentration ($T_{max}$) of {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile of about 0.5 hours to about 3 hours.

In some embodiments, oral administration of one or more sustained release dosage forms to a fasted individual provides a mean time to peak plasma concentration ($T_{max}$) of {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile of at least 0.5 hours.

In some embodiments, oral administration of one or more sustained release dosage forms to a fasted individual provides a ratio of mean peak plasma concentration ($C_{max}$) to mean 12-hour plasma concentration ($C_{12h}$) of {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile of about 5 to about 50.

In some embodiments, oral administration of one or more sustained release dosage forms to a fasted individual provides a ratio of mean peak plasma concentration ($C_{max}$) to mean 12-hour plasma concentration ($C_{12h}$) of {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile of about 9 to about 40.

In some embodiments, oral administration of one or more sustained release dosage forms to a fasted individual provides a ratio of mean peak plasma concentration ($C_{max}$) to mean 12-hour plasma concentration ($C_{12h}$) of {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile of about 15 to about 30.

In some embodiments, oral administration of one or more sustained release dosage forms to a fasted individual provides a mean half-life ($t_{1/2}$) of {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile of about 1 hour to about 20 hours.

In some embodiments, oral administration of one or more sustained release dosage forms to an individual after a high-fat meal provides a mean time to peak plasma concentration ($T_{max}$) of {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile of about 1 hour to about 9 hours.

In some embodiments, oral administration of one or more sustained release dosage forms to an individual after a high-fat meal provides a mean time to peak plasma concentration ($T_{max}$) of {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile of at least 1.5 hours.

In some embodiments, oral administration of one or more sustained release dosage forms to an individual after a high-fat meal provides a ratio of mean peak plasma concentration ($C_{max}$) to mean 12-hour plasma concentration ($C_{12h}$) of {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile of about 10 to about 70.

In some embodiments, oral administration of one or more sustained release dosage forms to an individual after a high-fat meal provides a ratio of mean peak plasma concentration ($C_{max}$) to mean 12-hour plasma concentration ($C_{12h}$) of {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile of about 15 to about 50.

In some embodiments, oral administration of one or more sustained release dosage forms to an individual after a high-fat meal provides a ratio of mean peak plasma concentration ($C_{max}$) to mean 12-hour plasma concentration ($C_{12h}$) of {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile of about 25 to about 45.

In some embodiments, oral administration of one or more sustained release dosage forms to an individual after a high-fat meal provides a mean half-life ($t_{1/2}$) of {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile of about 1 hour to about 7 hours.

In some embodiments, oral administration of one or more sustained release dosage forms to an individual after a high-fat meal provides a mean half-life ($t_{1/2}$) of {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile of about 2 hours to about 5 hours.

In some embodiments, the one or more sustained release dosage forms are each a tablet. In some embodiments, the one or more sustained release dosage forms are prepared by process comprising wet granulation.

In some embodiments, the one or more sustained release dosage forms each comprises one or more hypromelloses. In some embodiments, the one or more sustained release dosage forms each comprises one or more excipients independently selected from hypromelloses and microcrystalline celluloses. In some embodiments, the one or more sustained release dosage forms each comprises one or more excipients independently selected from hypromelloses, microcrystalline celluloses, magnesium stearate, lactose, and lactose monohydrate. In some embodiments, the one or more sustained release dosage forms each comprises a first hypromellose characterized by having an apparent viscosity at a concentration of 2% in water of about 80 cP to about 120 cP and a second hypromellose characterized by having an apparent viscosity at a concentration of 2% in water of about 3000 cP to about 5600 cP.

In some embodiments, the one or more sustained release dosage forms each comprises about 10% to about 15% by weight of one or more hypromelloses. In some embodiments, the one or more sustained release dosage forms each comprises about 16% to about 22% by weight of microcrystalline cellulose. In some embodiments, the one or more sustained release dosage forms each comprises about 45% to about 55% by weight of lactose monohydrate. In some embodiments, the one or more sustained release dosage forms each comprises about 0.3% to about 0.7% by weight of magnesium stearate.

In some embodiments, the present application provides a method of treating myelofibrosis in a patient, comprising orally administering to said patient a once-daily dose of about 400 mg to about 600 mg on a free base basis of {1-{1-[3-fluoro-2-(trifluoromethyl)isonicotinoyl]piperidin- 4-yl}-3-[4-(7H-pyrrolo[2,3-d]pyrimidin-4-yl)-1H-pyrazol-1-yl]azetidin-3-yl}acetonitrile, or a pharmaceutically acceptable salt thereof, wherein the dose comprises one or more sustained release dosage forms each comprising {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or a pharmaceutically acceptable salt thereof; wherein the method results in a reduced total symptom score (TSS) of said patient compared with baseline. In some embodiments, the present application provides a method of treating myelofibrosis in a patient, comprising orally administering to said patient the one or more sustained release dosage forms as a once-daily dosage of about 600 mg on a free base basis of {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or a pharmaceutically acceptable salt thereof; wherein the method results in a reduced total symptom score (TSS) of said patient compared with baseline.

In some embodiments, the present application provides a method of treating myelofibrosis in a patient, comprising orally administering to said patient the one or more sustained release dosage forms as a once-daily dosage of about 500 mg on a free base basis of {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or a pharmaceutically acceptable salt thereof; wherein the method results in a reduced total symptom score (TSS) of said patient compared with baseline.

In some embodiments, the present application provides a method of treating myelofibrosis in a patient, comprising orally administering to said patient the one or more sustained release dosage forms as a once-daily dosage of about 400 mg on a free base basis of {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or a pharmaceutically acceptable salt thereof; wherein the method results in a reduced total symptom score (TSS) of said patient compared with baseline.

In some embodiments of the methods in the preceding three paragraphs, the one or more sustained release dosage forms are six dosage forms of about 100 mg on a free base basis of {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or a pharmaceutically acceptable salt thereof, are provided. In some embodiments of the methods in the preceding three paragraphs, the one or more sustained release dosage forms are three dosage forms of about 200 mg on a free base basis of {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or a pharmaceutically acceptable salt thereof, are provided. In some embodiments of the methods in the preceding three paragraphs, the one or more sustained release dosage forms are two dosage forms of about 300 mg on a free base basis of {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or a pharmaceutically acceptable salt thereof, are provided. In some embodiments of the methods in the preceding three paragraphs, the one or more sustained release dosage forms is one dosage form of about 600 mg on a free base basis of {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or a pharmaceutically acceptable salt thereof, is provided.

In some embodiments, "total symptom score (TSS)" refers to the TSS derived from the modified Myelofibrosis Symptom Assessment Form (MFSAF) (e.g., v3.0) electronic diary as compared with baseline (baseline is the patient's baseline TSS before treatment). In some embodiments, myelofibrosis is primary myelofibrosis (PMF), post-polycythemia vera MF, or post-essential thrombocythemia MF.

The present application also provides a method of treating an autoimmune disease, a cancer, a myeloproliferative disorder, an inflammatory disease, a bone resorption disease, or organ transplant rejection in a patient in need thereof, comprising orally administering to said patient a once-daily dose of about 400 mg to about 600 mg on a free base basis of {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or a pharmaceutically acceptable salt thereof, wherein the dose comprises one or more sustained release dosage forms each comprising {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or a pharmaceutically acceptable salt thereof; wherein said method results in reduced anemia.

The present application also provides a method of treating an autoimmune disease, a cancer, a myeloproliferative disorder, an inflammatory disease, a bone resorption disease, or organ transplant rejection in a patient in need thereof, wherein the method comprises orally administering to said patient the one or more sustained release dosage forms as a once-daily dosage of about 600 mg on a free base basis of {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or a pharmaceutically acceptable salt thereof; wherein said method results in reduced anemia.

The present application also provides a method of treating an autoimmune disease, a cancer, a myeloproliferative disorder, an inflammatory disease, a bone resorption disease, or organ transplant rejection in a patient in need thereof, wherein the method comprises orally administering to said patient the one or more sustained release dosage forms as a once-daily dosage of about 500 mg on a free base basis of {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or a pharmaceutically acceptable salt thereof; wherein said method results in reduced anemia.

The present application also provides a method of treating an autoimmune disease, a cancer, a myeloproliferative disorder, an inflammatory disease, a bone resorption disease, or organ transplant rejection in a patient in need thereof, wherein the method comprises orally administering to said patient the one or more sustained release dosage forms as a once-daily dosage of about 400 mg on a free base basis of {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or a pharmaceutically acceptable salt thereof; wherein said method results in reduced anemia. In some embodiments, the one or more sustained release dosage forms are six dosage forms of about 100 mg on a free base basis of {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or a pharmaceutically acceptable salt thereof, are provided. In some embodiments, the one or more sustained release dosage forms are three dosage forms of about 200 mg on a free base basis of {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or a pharmaceutically acceptable salt thereof, are provided. In some embodiments, the one or more sustained release dosage forms are two dosage forms of about 300 mg on a free base basis of {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or a pharmaceutically acceptable salt thereof, are provided. In some embodiments, the one or more sustained release dosage forms is one dosage form of about 600 mg on a free base basis of {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or a pharmaceutically acceptable salt thereof, is provided.

Reduced anemia is relative to that experienced for a twice-daily dose of 200 mg on a free base basis of {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or a pharmaceutically acceptable salt thereof, wherein the dose comprises one or more sustained release dosage forms each comprising {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or a pharmaceutically acceptable salt thereof.

The compound of Formula I is a JAK inhibitor. A JAK1 selective inhibitor is a compound that inhibits JAK1 activity preferentially over other Janus kinases. JAK1 plays a central role in a number of cytokine and growth factor signaling pathways that, when dysregulated, can result in or contribute to disease states. For example, IL-6 levels are elevated in rheumatoid arthritis, a disease in which it has been suggested to have detrimental effects (Fonesca, J. E. et al., Autoimmunity Reviews, 8:538-42, 2009). Because IL-6 signals, at least in part, through JAK1, antagonizing IL-6 directly or indirectly through JAK1 inhibition is expected to provide clinical benefit (Guschin, D., N., et al Embo J 14:1421, 1995; Smolen, J. S., et al. Lancet 371:987, 2008). Moreover, in some cancers JAK1 is mutated resulting in constitutive undesirable tumor cell growth and survival (Mullighan C G, Proc Natl Acad Sci USA. 106:9414-8, 2009; Flex E., et al. J Exp Med. 205:751-8, 2008). In other autoimmune diseases and cancers elevated systemic levels of inflammatory cytokines that activate JAK1 may also contribute to the disease and/or associated symptoms. Therefore, patients with such diseases may benefit from JAK1 inhibition. Selective inhibitors of JAK1 may be efficacious while avoiding unnecessary and potentially undesirable effects of inhibiting other JAK kinases.

Selective inhibitors of JAK1, relative to other JAK kinases, may have multiple therapeutic advantages over less selective inhibitors. With respect to selectivity against JAK2, a number of important cytokines and growth factors signal through JAK2 including, for example, erythropoietin (Epo) and thrombopoietin (Tpo) (Parganas E, et al. Cell. 93:385-95, 1998). Epo is a key growth factor for red blood cells production; hence a paucity of Epo-dependent signaling can result in reduced numbers of red blood cells and anemia (Kaushansky K, NEJM 354:2034-45, 2006). Tpo, another example of a JAK2-dependent growth factor, plays a central role in controlling the proliferation and maturation of megakaryocytes—the cells from which platelets are produced (Kaushansky K, NEJM 354:2034-45, 2006). As such, reduced Tpo signaling would decrease megakaryocyte numbers (megakaryocytopenia) and lower circulating platelet counts (thrombocytopenia). This can result in undesirable and/or uncontrollable bleeding. Reduced inhibition of other JAKs, such as JAK3 and Tyk2, may also be desirable as humans lacking functional version of these kinases have been shown to suffer from numerous maladies such as severe-combined immunodeficiency or hyperimmunoglobulin E syndrome (Minegishi, Y, et al. Immunity 25:745-55, 2006; Macchi P, et al. Nature. 377:65-8, 1995). Therefore a JAK1 inhibitor with reduced affinity for other JAKs would have significant advantages over a less-selective inhibitor with respect to reduced side effects involving immune suppression, anemia and thrombocytopenia.

Another aspect of the present invention pertains to methods of treating a JAK-associated disease or disorder in an individual (e.g., patient) by administering to the individual in need of such treatment a sustained-release dosage form of the invention. A JAK-associated disease can include any disease, disorder or condition that is directly or indirectly linked to expression or activity of the JAK, including overexpression and/or abnormal activity levels. A JAK-associated disease can also include any disease, disorder or condition that can be prevented, ameliorated, or cured by modulating JAK activity.

Examples of JAK-associated diseases include diseases involving the immune system including, for example, organ transplant rejection (e.g., allograft rejection and graft versus host disease).

Further examples of JAK-associated diseases include autoimmune diseases such as multiple sclerosis, rheumatoid arthritis, juvenile arthritis, psoriatic arthritis, type I diabetes, lupus, psoriasis, inflammatory bowel disease, ulcerative colitis, Crohn's disease, myasthenia gravis, immunoglobulin nephropathies, myocarditis, autoimmune thyroid disorders, chronic obstructive pulmonary disease (COPD), and the like. In some embodiments, the autoimmune disease is an autoimmune bullous skin disorder such as pemphigus vulgaris (PV) or bullous pemphigoid (BP).

Further examples of JAK-associated diseases include allergic conditions such as asthma, food allergies, eszematous dermatitis, contact dermatitis, atopic dermatitis (atropic eczema), and rhinitis. Further examples of JAK-associated diseases include viral diseases such as Epstein Barr Virus (EBV), Hepatitis B, Hepatitis C, HIV, HTLV 1, Varicella-Zoster Virus (VZV) and Human Papilloma Virus (HPV).

Further examples of JAK-associated disease include diseases associated with cartilage turnover, for example, gouty arthritis, septic or infectious arthritis, reactive arthritis, reflex sympathetic dystrophy, algodystrophy, Tietze syndrome, costal athropathy, osteoarthritis deformans endemica, Mseleni disease, Handigodu disease, degeneration resulting from fibromyalgia, systemic lupus erythematosus, scleroderma, or ankylosing spondylitis.

Further examples of JAK-associated disease include congenital cartilage malformations, including hereditary chondrolysis, chondrodysplasias, and pseudochrondrodysplasias (e.g., microtia, enotia, and metaphyseal chrondrodysplasia).

Further examples of JAK-associated diseases or conditions include skin disorders such as psoriasis (for example, psoriasis vulgaris), atopic dermatitis, skin rash, skin irritation, skin sensitization (e.g., contact dermatitis or allergic contact dermatitis). For example, certain substances including some pharmaceuticals when topically applied can cause skin sensitization. In some embodiments, co-administration or sequential administration of at least one JAK inhibitor of the invention together with the agent causing unwanted sensitization can be helpful in treating such unwanted sensitization or dermatitis. In some embodiments, the skin disorder is treated by topical administration of at least one JAK inhibitor of the invention.

In further embodiments, the JAK-associated disease is cancer including those characterized by solid tumors (e.g., prostate cancer, renal cancer, hepatic cancer, pancreatic cancer, gastric cancer, breast cancer, lung cancer, cancers of the head and neck, thyroid cancer, glioblastoma, Kaposi's sarcoma, Castleman's disease, uterine leiomyosarcoma, melanoma etc.), hematological cancers (e.g., lymphoma, leukemia such as acute lymphoblastic leukemia (ALL), acute myelogenous leukemia (AML) or multiple myeloma), and skin cancer such as cutaneous T-cell lymphoma (CTCL) and cutaneous B-cell lymphoma. Example CTCLs include Sezary syndrome and mycosis fungoides.

In some embodiments, the dosage forms described herein, or in combination with other JAK inhibitors, such as those reported in U.S. Ser. No. 11/637,545, which is incorporated herein by reference in its entirety, can be used to treat inflammation-associated cancers. In some embodiments, the cancer is associated with inflammatory bowel disease. In some embodiments, the inflammatory bowel disease is ulcerative colitis. In some embodiments, the inflammatory bowel disease is Crohn's disease. In some embodiments, the inflammation-associated cancer is colitis-associated cancer. In some embodiments, the inflammation-associated cancer is colon cancer or colorectal cancer. In some embodiments, the cancer is gastric cancer, gastrointestinal carcinoid tumor, gastrointestinal stromal tumor (GIST), adenocarcinoma, small intestine cancer, or rectal cancer.

JAK-associated diseases can further include those characterized by expression of: JAK2 mutants such as those having at least one mutation in the pseudo-kinase domain (e.g., JAK2V617F); JAK2 mutants having at least one mutation outside of the pseudo-kinase domain; JAK1 mutants; JAK3 mutants; erythropoietin receptor (EPOR) mutants; or deregulated expression of CRLF2.

JAK-associated diseases can further include myeloproliferative disorders (MPDs) such as polycythemia vera (PV), essential thrombocythemia (ET), myelofibrosis with myeloid metaplasia (MMM), primary myelofibrosis (PMF), chronic myelogenous leukemia (CML), chronic myelomonocytic leukemia (CMML), hypereosinophilic syndrome (HES), systemic mast cell disease (SMCD), and the like. In some embodiments, the myeloproliferative disorder is myelofibrosis (e.g., primary myelofibrosis (PMF) or post polycythemia vera/essential thrombocythemia myelofibrosis (Post-PV/ET MF)). In some embodiments, the myeloproliferative disorder is post-essential thrombocythemia myelofibrosis (Post-ET). In some embodiments, the myeloproliferative disorder is post polycythemia vera myelofibrosis (Post-PV MF).

In some embodiments, dosage forms described herein can be used to treat pulmonary arterial hypertension.

The present invention further provides a method of treating dermatological side effects of other pharmaceuticals by administration of the dosage forms of the invention. For example, numerous pharmaceutical agents result in unwanted allergic reactions which can manifest as acneiform rash or related dermatitis. Example pharmaceutical agents that have such undesirable side effects include anticancer drugs such as gefitinib, cetuximab, erlotinib, and the like. The dosage forms of the invention can be administered systemically in combination with (e.g., simultaneously or sequentially) the pharmaceutical agent having the undesirable dermatological side effect.

Further JAK-associated diseases include inflammation and inflammatory diseases. Example inflammatory diseases include sarcoidosis, inflammatory diseases of the eye (e.g., iritis, uveitis, scleritis, conjunctivitis, or related disease), inflammatory diseases of the respiratory tract (e.g., the upper respiratory tract including the nose and sinuses such as rhinitis or sinusitis or the lower respiratory tract including bronchitis, chronic obstructive pulmonary disease, and the like), inflammatory myopathy such as myocarditis, and other inflammatory diseases. In some embodiments, the inflammation disease of the eye is blepharitis.

The dosage forms described herein can further be used to treat ischemia reperfusion injuries or a disease or condition related to an inflammatory ischemic event such as stroke or cardiac arrest. The dosage forms described herein can further be used to treat endotoxin-driven disease state (e.g., complications after bypass surgery or chronic endotoxin states contributing to chronic cardiac failure). The dosage forms described herein can further be used to treat anorexia, cachexia, or fatigue such as that resulting from or associated with cancer. The dosage forms described herein can further be used to treat restenosis, sclerodermitis, or fibrosis. The dosage forms described herein can further be used to treat conditions associated with hypoxia or astrogliosis such as, for example, diabetic retinopathy, cancer, or neurodegeneration. See, e.g., Dudley, A. C. et al. *Biochem. J.* 2005, 390(Pt 2):427-36 and Sriram, K. et al. *J. Biol. Chem.* 2004, 279 (19):19936-47. Epub 2004 Mar. 2, both of which are incorporated herein by reference in their entirety. The JAK inhibitors described herein can be used to treat Alzheimer's disease.

The dosage forms described herein can further be used to treat other inflammatory diseases such as systemic inflammatory response syndrome (SIRS) and septic shock.

The dosage forms described herein can further be used to treat gout and increased prostate size due to, e.g., benign prostatic hypertrophy or benign prostatic hyperplasia.

Further JAK-associated diseases include bone resorption diseases such as osteoporosis, osteoarthritis. Bone resorption can also be associated with other conditions such as hormonal imbalance and/or hormonal therapy, autoimmune disease (e.g. osseous sarcoidosis), or cancer (e.g. myeloma). The reduction of the bone resorption due to the compound of Formula I can be about 10%, about 20%, about 30%, about 40%, about 50%, about 60%, about 70%, about 80%, or about 90%.

In some embodiments, the dosage forms described herein can further be used to treat a dry eye disorder. As used herein, "dry eye disorder" is intended to encompass the disease states summarized in a recent official report of the Dry Eye Workshop (DEWS), which defined dry eye as "a multifactorial disease of the tears and ocular surface that results in symptoms of discomfort, visual disturbance, and tear film instability with potential damage to the ocular surface. It is accompanied by increased osmolarity of the tear film and inflammation of the ocular surface." Lemp, "The Definition and Classification of Dry Eye Disease: Report of the Definition and Classification Subcommittee of the International Dry Eye Workshop", *The Ocular Surface*, 5(2), 75-92 April 2007, which is incorporated herein by reference in its entirety. In some embodiments, the dry eye disorder is selected from aqueous tear-deficient dry eye (ADDE) or evaporative dry eye disorder, or appropriate combinations thereof. In some embodiments, the dry eye disorder is Sjogren syndrome dry eye (SSDE). In some embodiments, the dry eye disorder is non-Sjogren syndrome dry eye (NSSDE).

In a further aspect, the present invention provides a method of treating conjunctivitis, uveitis (including chronic uveitis), chorioditis, retinitis, cyclitis, sclieritis, episcleritis, or iritis; treating inflammation or pain related to corneal transplant, LASIK (laser assisted in situ keratomileusis), photorefractive keratectomy, or LASEK (laser assisted sub-epithelial keratomileusis); inhibiting loss of visual acuity related to corneal transplant, LASIK, photorefractive keratectomy, or LASEK; or inhibiting transplant rejection in a patient in need thereof, comprising administering to the patient a dosage form of the invention.

Additionally, the dosage forms of the invention, or in combination with other JAK inhibitors, such as those reported in U.S. Ser. No. 11/637,545, which is incorporated herein by reference in its entirety, can be used to treat respiratory dysfunction or failure associated with viral infection, such as influenza and SARS.

In some embodiments, the present invention provides a dosage form as described in any of the embodiments herein, for use in a method of treating any of the diseases or disorders described herein. In some embodiments, the present invention provides the use of a dosage form as described in any of the embodiments herein, for the preparation of a medicament for use in a method of treating any of the diseases or disorders described herein.

In some embodiments, the present invention provides a dosage form as described herein, or a pharmaceutically acceptable salt thereof, for use in a method of modulating JAK1. In some embodiments, the present invention also provides use of a dosage form as described herein, or a pharmaceutically acceptable salt thereof, for the preparation of a medicament for use in a method of modulating JAK1.

As used herein, the term "individual" is a human. In some embodiments, the human is an adult subject.

As used herein, the term "treating" or "treatment" refers to one or more of (1) inhibiting the disease; for example, inhibiting a disease, condition or disorder in an individual who is experiencing or displaying the pathology or symptomatology of the disease, condition or disorder (i.e., arresting further development of the pathology and/or symptomatology); and (2) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease.

Combination Therapies

One or more additional pharmaceutical agents such as, for example, chemotherapeutics, anti-inflammatory agents, steroids, immunosuppressants, as well as Bcr-Abl, Flt-3, RAF and FAK kinase inhibitors such as, for example, those described in WO 2006/056399, which is incorporated herein by reference in its entirety, or other agents can be used in combination with the dosage forms described herein for treatment of JAK-associated diseases, disorders or conditions. The one or more additional pharmaceutical agents can be administered to a patient simultaneously or sequentially.

Example chemotherapeutics include proteosome inhibitors (e.g., bortezomib), thalidomide, revlimid, and DNA-damaging agents such as melphalan, doxorubicin, cyclophosphamide, vincristine, etoposide, carmustine, and the like.

Example steroids include corticosteroids such as dexamethasone or prednisone.

Example Bcr-Abl inhibitors include the compounds, and pharmaceutically acceptable salts thereof, of the genera and species disclosed in U.S. Pat. No. 5,521,184, WO 04/005281, and U.S. Ser. No. 60/578,491, all of which are incorporated herein by reference in their entirety.

Example suitable Flt-3 inhibitors include compounds, and their pharmaceutically acceptable salts, as disclosed in WO 03/037347, WO 03/099771, and WO 04/046120, all of which are incorporated herein by reference in their entirety.

Example suitable RAF inhibitors include compounds, and their pharmaceutically acceptable salts, as disclosed in WO 00/09495 and WO 05/028444, both of which are incorporated herein by reference in their entirety.

Example suitable FAK inhibitors include compounds, and their pharmaceutically acceptable salts, as disclosed in WO 04/080980, WO 04/056786, WO 03/024967, WO 01/064655, WO 00/053595, and WO 01/014402, all of which are incorporated herein by reference in their entirety.

In some embodiments, one or more of the dosage forms of the invention can be used in combination with one or more other kinase inhibitors including imatinib, particularly for treating patients resistant to imatinib or other kinase inhibitors.

In some embodiments, one or more dosage forms of the invention can be used in combination with a chemotherapeutic in the treatment of cancer, such as multiple myeloma, and may improve the treatment response as compared to the response to the chemotherapeutic agent alone, without exacerbation of its toxic effects. Examples of additional pharmaceutical agents used in the treatment of multiple myeloma, for example, can include, without limitation, melphalan, melphalan plus prednisone [MP], doxorubicin, dexamethasone, and Velcade (bortezomib). Further additional agents used in the treatment of multiple myeloma include Bcr-Abl, Flt-3, RAF and FAK kinase inhibitors. Additive or synergistic effects are desirable outcomes of combining a dosage form of the present invention with an additional agent. Furthermore, resistance of multiple myeloma cells to agents such as dexamethasone may be reversible upon treatment with a dosage form of the present invention. The agents can be combined with the present compounds in a single or continuous dosage form, or the agents can be administered simultaneously or sequentially as separate dosage forms.

In some embodiments, a corticosteroid such as dexamethasone is administered to a patient in combination with at the dosage form of the invention where the dexamethasone is administered intermittently as opposed to continuously.

In some further embodiments, combinations of one or more JAK inhibitors of the invention with other therapeutic agents can be administered to a patient prior to, during, and/or after a bone marrow transplant or stem cell transplant.

In some embodiments, the additional therapeutic agent is fluocinolone acetonide (Retisert®), or rimexolone (AL-2178, Vexol, Alcon).

In some embodiments, the additional therapeutic agent is cyclosporine (Restasis®).

In some embodiments, the additional therapeutic agent is a corticosteroid. In some embodiments, the corticosteroid is triamcinolone, dexamethasone, fluocinolone, cortisone, prednisolone, or flumetholone.

In some embodiments, the additional therapeutic agent is selected from Dehydrex™ (Holles Labs), Civamide (Opko), sodium hyaluronate (Vismed, Lantibio/TRB Chemedia), cyclosporine (ST-603, Sirion Therapeutics), ARG101(T) (testosterone, Argentis), AGR1012(P) (Argentis), ecabet sodium (Senju-Ista), gefarnate (Santen), 15-(s)-hydroxyeicosatetraenoic acid (15(S)-HETE), cevilemine, doxycycline (ALTY-0501, Alacrity), minocycline, iDestrin™ (NP50301, Nascent Pharmaceuticals), cyclosporine A (Nova22007, Novagali), oxytetracycline (Duramycin, MOLI1901, Lantibio), CF101 (2S,3S,4R,5R)-3,4-dihydroxy-5-[6-[(3-iodophenyl)methylamino]purin-9-yl]-N-methyl-oxolane-2-carbamyl, Can-Fite Biopharma), voclosporin (LX212 or LX214, Lux Biosciences), ARG103 (Agentis), RX-10045 (synthetic resolvin analog, Resolvyx), DYN15 (Dyanmis Therapeutics), rivoglitazone (DE011, Daiichi Sanko), TB4 (RegeneRx), OPH-01 (Ophtalmis Monaco), PCS101 (Pericor Science), REV1-31 (Evolutec), Lacritin (Senju), rebamipide (Otsuka-Novartis), OT-551 (Othera), PAI-2 (University of Pennsylvania and Temple University), pilocarpine, tacrolimus, pimecrolimus (AMS981, Novartis), loteprednol etabonate, rituximab, diquafosol tetrasodium (INS365, Inspire), KLS-0611 (Kissei Pharmaceuticals), dehydroepiandrosterone, anakinra, efalizumab, mycophenolate sodium, etanercept (Embrel®), hydroxychloroquine, NGX267 (TorreyPines Therapeutics), actemra, gemcitabine, oxaliplatin, L-asparaginase, or thalidomide.

In some embodiments, the additional therapeutic agent is an anti-angiogenic agent, cholinergic agonist, TRP-1 receptor modulator, a calcium channel blocker, a mucin secretagogue, MUC 1 stimulant, a calcineurin inhibitor, a corticosteroid, a P2Y2 receptor agonist, a muscarinic receptor agonist, an mTOR inhibitor, another JAK inhibitor, Bcr-Abl kinase inhibitor, Flt-3 kinase inhibitor, RAF kinase inhibitor, and FAK kinase inhibitor such as, for example, those described in WO 2006/056399, which is incorporated herein by reference in its entirety. In some embodiments, the additional therapeutic agent is a tetracycline derivative (e.g., minocycline or doxycline). In some embodiments, the additional therapeutic agent binds to FKBP12.

In some embodiments, the additional therapeutic agent is an alkylating agent or DNA cross-linking agent; an antimetabolite/demethylating agent (e.g., 5-fluorouracil, capecitabine or azacitidine); an anti-hormone therapy (e.g., hormone receptor antagonists, SERMs, or aromatase inhibitor); a mitotic inhibitor (e.g. vincristine or paclitaxel); an topoisomerase (I or II) inhibitor (e.g. mitoxantrone and irinotecan); an apoptotic inducers (e.g. ABT-737); a nucleic acid therapy (e.g. antisense or RNAi); nuclear receptor ligands (e.g., agonists and/or antagonists: all-trans retinoic acid or bexarotene); epigenetic targeting agents such as histone deacetylase inhibitors (e.g. vorinostat), hypomethylating agents (e.g. decitabine); regulators of protein stability such as Hsp90 inhibitors, ubiquitin and/or ubiquitin like conjugating or deconjugating molecules; or an EGFR inhibitor (erlotinib).

In some embodiments, the additional therapeutic agent(s) are demulcent eye drops (also known as "artificial tears"), which include, but are not limited to, compositions containing polyvinylalcohol, hydroxypropyl methylcellulose, glycerin, polyethylene glycol (e.g. PEG400), or carboxymethyl cellulose. Artificial tears can help in the treatment of dry eye by compensating for reduced moistening and lubricating capacity of the tear film. In some embodiments, the additional therapeutic agent is a mucolytic drug, such as N-acetyl-cysteine, which can interact with the mucoproteins and, therefore, to decrease the viscosity of the tear film.

In some embodiments, the additional therapeutic agent includes an antibiotic, antiviral, antifungal, anesthetic, anti-inflammatory agents including steroidal and non-steroidal anti-inflammatories, and anti-allergic agents. Examples of suitable medicaments include aminoglycosides such as amikacin, gentamycin, tobramycin, streptomycin, netilmycin, and kanamycin; fluoroquinolones such as ciprofloxacin, norfloxacin, ofloxacin, trovafloxacin, lomefloxacin, levofloxacin, and enoxacin; naphthyridine; sulfonamides; polymyxin; chloramphenicol; neomycin; paramomycin; colistimethate; bacitracin; vancomycin; tetracyclines; rifampin and its derivatives ("rifampins"); cycloserine; beta-lactams; cephalosporins; amphotericins; fluconazole; flucytosine; natamycin; miconazole; ketoconazole; corticosteroids; diclofenac; flurbiprofen; ketorolac; suprofen; cromolyn; lodoxamide; levocabastin; naphazoline; antazoline; pheniramine; or azalide antibiotic.

It is further appreciated that certain features of the invention, which are, for clarity, described in the context of separate embodiments, can also be provided in combination in a single embodiment (as if the embodiments of the specification are written as multiply dependent claims).

EXAMPLE 1

Preparation of Sustained Release Formulations

Sustained release tablets were prepared with the excipients being in the amounts shown in the table below. Protocol A was used for the SR1 tablets, protocol B was used for the SR2 tablets, Protocol C was used for the SR3 tablets and the 25 mg SR tablets, and Protocol D was used for the SR4 tablets.

Protocol A:

Step 1. Individually screen the adipic acid salt of the compound of Formula I, microcrystalline cellulose, hypromelloses (Methocel K100 LV and Methocel K4M), and lactose monohydrate.

Step 2. Transfer the screened material from Step 1 to a suitable blender and mix.

Step 3. Transfer the blend from Step 2 to a suitable granulator and mix.

Step 4. Add purified water while mixing.

Step 5. Transfer the granules from Step 4 into a suitable dryer and dry until LOD is less than 3%.

Step 6. Screen the granules from Step 5.

Step 7. Mix screened Magnesium Stearate with granules in Step 6 in a suitable blender.

Step 8. Compress the final blend in Step 7 on a suitable rotary tablet press.

Protocol B:

Step 1. Individually screen the adipic acid salt of the compound of Formula I, microcrystalline cellulose, hypromellose and pregelatinized starch.

Step 2. Transfer the screened material from Step 1 to a suitable blender and mix.

Step 3. Transfer the blend from Step 2 to a suitable granulator and mix.

Step 4. Add purified water while mixing.

Step 5. Transfer the granules from Step 4 into a suitable dryer and dry until LOD is less than 3%.

Step 6. Screen the granules from Step 5.

Step 7. Individually screened polyox, butylated hydroxytoluene and colloidal silicone dioxide.

Step 8. Transfer the granules from Step 6 and material from Step 7 into a suitable blender and mix.

Step 9. Add screened Magnesium Stearate to the material in Step 8 and continue blending.

Step 10. Compress the final blend in Step 9 on a suitable rotary tablet press.

Protocol C:

Step 1. Individually screen lactose monohydrate, the adipic acid salt of the compound of Formula I, microcrystalline cellulose and hypromelloses through a suitable screen.

Step 2. Transfer the screened material from Step 1 to a suitable blender and mix.

Step 3. Transfer the blend from Step 2 to a suitable granulator and mix.

Step 4. Add purified water while mixing.

Step 5. Screen wet granules through a suitable screen.

Step 6. Transfer the granules from Step 5 into a suitable dryer and dry until LOD is less than 3%.

Step 7. Mill the granules from Step 6.

Step 8. Mix screened magnesium stearate with granules in Step 7 in a suitable blender.

Step 9. Compress the final blend in Step 8 on a suitable rotary tablet press.

Protocol D:

Step 1. Individually screen pregelatinized starch, the adipic acid salt of the compound of Formula I, hypromellose, and a portion of required microcrystalline cellulose through a suitable screen.

Step 2. Transfer the screened material from Step 1 to a suitable blender and mix.

Step 3. Transfer the blend from Step 2 to a suitable granulator and mix.

Step 4. Add purified water while mixing.

Step 5. Screen wet granules through a suitable screen.

Step 6. Transfer the granules from Step 5 into a suitable dryer and dry until LOD is less than 3%.

Step 7. Mill the granules from Step 6.

Step 8. Screen the remaining portion of microcrystalline cellulose and half of the sodium bicarbonate.

Step 9. Transfer the milled granules from Step 7 and screened materials from Step 8 into a suitable blender and mix.

Step 10. Screen the remaining portion of sodium bicarbonate and mix with blend in Step 9.

Step 11. Screen magnesium stearate and mix with blend in Step 10.

Step 12. Compress the final blend in Step 11 on a suitable rotary tablet press.

SR1: Composition of 100 mg Sustained Release Tablets

| Component | Function | Weight (mg/tablet) | Composition (wt %) |
|---|---|---|---|
| Adipic acid salt of the compound of Formula I [a] | Active | 126.42 [a] | 21.1 |
| Microcrystalline Cellulose | Filler | 60.0 | 10.0 |
| Hypromellose (Methocel K100LV) | Release Control | 60.0 | 10.0 |
| Hypromellose (Methocel K4M) | Release Control | 60.0 | 10.0 |
| Lactose Monohydrate | Filler | 290.58 | 48.4 |
| Magnesium Stearate [b] | Lubricant | 3.0 | 0.5 |
| Purified Water [c] | Granulating Liquid | q.s. | — |
| Total | | 600.0 | 100 |

[a] Conversion factor for adipate salt to free base is 0.7911
[b] Added after granulation
[c] Removed during processing SR2: Composition of 100 mg Sustained Release Tablets

| Component | Function | Weight (mg/tablet) | Composition (wt %) |
|---|---|---|---|
| Adipic acid salt of the compound of Formula I [a] | Active | 126.4 [a] | 21.1 |
| Microcrystalline Cellulose | Filler | 180.0 | 30.0 |
| Hypromellose (Methocel K100LV) | Binder | 6.0 | 1.0 |
| Polyethylene Oxide (Polyox WRS 1105) [b] | Release Control | 180.0 | 30.0 |
| Pregelatinized Starch | Filler | 101.6 | 16.9 |
| Colloidal Silicon Dioxide [b] | Glidant | 3.0 | 0.5 |
| Butylated Hydroxytoluene [b] | Antioxidant | 0.012 | 0.002 |
| Magnesium Stearate [b] | Lubricant | 3.0 | 0.5 |
| Purified Water [c] | Granulating Liquid | q.s. | — |
| Total | | 600.0 | 100.0 |

[a] Conversion factor for adipate salt to free base is 0.7911
[b] Added after granulation
[c] Removed during processing SR3 (100 mg): Composition of 100 mg Sustained Release Tablets

| Component | Function | Weight (mg/tablet) | Composition (wt %) |
|---|---|---|---|
| Adipic acid salt of the compound of Formula I [a] | Active | 126.4 [a] | 21.1 |
| Microcrystalline Cellulose | Filler | 108.0 | 18.0 |
| Hypromellose (Methocel K100LV) | Release Control | 42.0 | 7.0 |
| Hypromellose (Methocel K4M) | Release Control | 30.0 | 5.0 |
| Lactose Monohydrate | Filler | 290.6 | 48.4 |
| Magnesium Stearate [b] | Lubricant | 3.0 | 0.5 |
| Purified Water [c] | Granulating Liquid | q.s. | — |
| Total | | 600.0 | 100.0 |

[a] Conversion factor for adipate salt to free base is 0.7911
[b] Added after granulation
[c] Removed during processing SR4: Composition of 100 mg Sustained Release Tablets

| Excipient | Function | Weight (mg/tablet) | Composition (wt %) |
|---|---|---|---|
| Adipic acid salt of the compound of Formula I [a] | Active | 126.4 [a] | 21.1 |
| Microcrystalline Cellulose [d] | Filler | 104.6 | 17.4 |
| Hypromellose (Methocel K100LV) | Release Control | 210.0 | 35.0 |
| Pregelatinized Starch | Filler | 60.0 | 10.0 |
| Sodium Bicarbonate [b] | Gastric Floating Aid | 96.0 | 16.0 |
| Magnesium Stearate [b] | Lubricant | 3.0 | 0.5 |
| Purified Water [c] | Granulation Liquid | q.s. | — |
| Total | | 600.0 | 100.0 |

[a] Conversion factor for adipate salt to free base is 0.7911
[b] Added after granulation
[c] Removed during processing
[d] Partial added before and partial added after granulation 25 mg SR: Composition of 25 mg Sustained Release Tablets

| Component | Function | Weight (mg/tablet) | Composition (wt %) |
|---|---|---|---|
| Adipic acid salt of the compound of Formula I [a] | Active | 31.6 [a] | 12.6 |
| Microcrystalline Cellulose | Filler | 105.0 | 42.0 |
| Hypromellose, (Methocel K100LV) | Release Control | 25.0 | 10.0 |
| Hypromellose, (Methocel K4M) | Release Control | 25.0 | 10.0 |
| Lactose Monohydrate | Filler | 62.15 | 24.9 |
| Magnesium Stearate [b] | Lubricant | 1.25 | 0.5 |
| Purified Water [c] | Granulating Liquid | q.s. | — |
| Total | | 250 | 100.0 |

[a] Conversion factor for adipate salt to free base is 0.7911
[b] Added after granulation
[c] Removed during processing

EXAMPLE 2

Preparation of the IR Formulation of the Compound of Formula I

The IR formulation used in the studies in Example 3 was prepared as 50 mg capsules with the composition shown in the table below according to Protocol E below.
Protocol E:
Step 1. Pre-mix the required amount of the adipic acid salt of the compound of Formula I and an approximately equal amount of silicified microcrystalline cellulose (SMCC).
Step 2. Pass the mixture in Step 1 through a suitable screen (for example 40 mesh).
Step 3. Screen the remaining SMCC through the same screen used in Step 2.
Step 4. Blend the screened SMCC from Step 3 along with mixture from Step 2 in a suitable blender (for example Turbula blender) for approximately 5 minutes.
Step 5. Fill the blend into capsules to desired fill weight.

| INGREDIENT | WEIGHT COMPOSITION (%) | QUANTITY PER UNIT (mg) |
|---|---|---|
| Adipic acid salt of the compound of Formula I | 35.11 | 63.20* |
| Silicified Microcrystalline Cellulose, NF (Prosolv SMCC HD 90) | 64.89 | 116.80 |
| TOTAL | 100.00% | 180.00 |
| #2 Capsules, Hard Gelatin, White Opaque | NA | 1 each |

*Adipic acid salt of the compound of Formula I with salt conversion factor of 0.7911

EXAMPLE 3

Relative Bioavailability Study of Sustained Release Dosage Forms

A total of 72 healthy adult subjects were enrolled in 6 cohorts (12 subjects per cohort) and randomized to treatment sequences within each cohort according to a randomization schedule. All treatments were single-dose administrations of the compound of Formula I. There was a washout period of 7 days between the treatment periods.

The SR1, SR2, SR3, and SR4 formulations were evaluated in Cohort 1, Cohort 2, Cohort 3, and Cohort 4, respectively (see Example 1 for SR1, SR2, SR3, SR4, and 25 mg SR tablets used in study). The subjects received the IR and SR treatments according to a 3-way crossover design:

Treatment A: 300 mg (6×50 mg capsule) IR formulation of the compound of Formula I administered orally after an overnight fast of at least 10 hours.

Treatment B: 300 mg (3×100 mg tablets) SR formulation of the compound of Formula I administered orally after an overnight fast of at least 10 hours.

Treatment C: 300 mg (3×100 mg tablets) SR formulation of the compound of Formula I administered orally after a high-fat meal.

The subjects in Cohort 5 received the following treatments in a 2-way crossover design:

Treatment A: 300 mg (3×100 mg tablets of the compound of Formula I) SR3 administered orally after an overnight fast of at least 10 hours.

Treatment B: 300 mg (3×100 mg tablets of the compound of Formula I) SR3 administered orally after a medium-fat meal.

The subjects in Cohort 6 received the following treatments in a 3-way crossover design:

Treatment A: 50 mg (2×25 mg tablets of the compound of Formula I (25 mg SR tablets from Example 1)) administered orally after an overnight fast of at least 10 hours.

Treatment B: 50 mg (2×25 mg tablets of the compound of Formula I (25 mg SR tablets from Example 1)) administered orally after a high-fat meal.

Treatment C: 100 mg (1×100 mg tablets) SR3 administered orally after an overnight fast of at least 10 hours.

Blood samples for determination of plasma concentrations of the compound of Formula I were collected using lavender top (K2EDTA) Vacutainer® tubes at 0, 0.25, 0.5, 1, 1.5, 2, 3, 4, 6, 8, 12, 16, 24, 36, and 48 hours post dose.

Plasma samples were assayed by a validated, GLP, LC/MS/MS method with a linear range of 5.0 to 5000 nM. Table 1 summarizes the accuracy and precision (CV %) of the assay quality control samples during the analysis of the plasma samples from this study.

TABLE 1

Accuracy and Precision of the Plasma Assay Quality Control Samples

| Analyte (Unit) | | Low QC | | | Middle QC | | | High QC | |
|---|---|---|---|---|---|---|---|---|---|
| | Theo | Accuracy | CV % | Theo | Accuracy | CV % | Theo | Accuracy | CV % |
| Compound of Formula I | 15.0 | 99.0% | 4.6% | 250 | 101% | 4.2% | 4000 | 99.5% | 2.2% |

CV % = percent coefficient of variability; QC = quality control; Theo = theoretical or nominal concentration.

For the PK analysis, the actual sample collection times were used. For any sample with missing actual collection time, the scheduled time was used provided that there was no protocol deviation noted for the collection of these samples.

Standard noncompartmental PK methods were used to analyze the data for the plasma concentration of the compound of Formula using Phoenix WinNonlin version 6.0 (Pharsight Corporation, Mountain View, Calif.). Thus, $C_{max}$ and $T_{max}$ were taken directly from the observed plasma concentration data. The terminal-phase disposition rate constant ($\lambda_z$) was estimated using a log-linear regression of the concentration data in the terminal disposition phase, and $t_{1/2}$ was estimated as $\ln(2)/\lambda_z$. $AUC_{0-t}$ was estimated using the linear trapezoidal rule for increasing concentrations and the log-trapezoidal rule for decreasing concentrations, and the total $AUC_{0-\infty}$ was calculated as $AUC_{0-t}+C_t/\lambda_z$. The oral-dose clearance (CL/F) was estimated as $Dose/AUC_{0-\infty}$ and the terminal-phase volume of distribution ($V_z/F$) was estimated as $Dose/[AUC_{0-\infty}*\lambda_z]$.

The log-transformed $C_{max}$ and AUC values (after dose normalization, where the doses were different) were compared between the fasted and fed dosing treatments, and between the SR and IR dosing treatments, using a crossover ANOVA (fixed factor=treatment, sequence and period, random effect=subject (sequence)). The adjusted geometric mean ratios of $C_{max}$ and AUC between the treatments (reference=IR or fasted administration of SR) and the corresponding 90% confidence intervals (CIs) were determined. In addition, the correlation between the observed food effect of a high-fat meal on $AUC_{0-\infty}$ and the relative bioavailability of the SR formulations (with reference to the IR capsule) were explored by a quantile plot using the data from all subjects who completed Treatment A, B, and C in Cohorts 1 to 4. The statistical analysis was performed using Phoenix WinNonlin version 6.0.

Figure 1B:
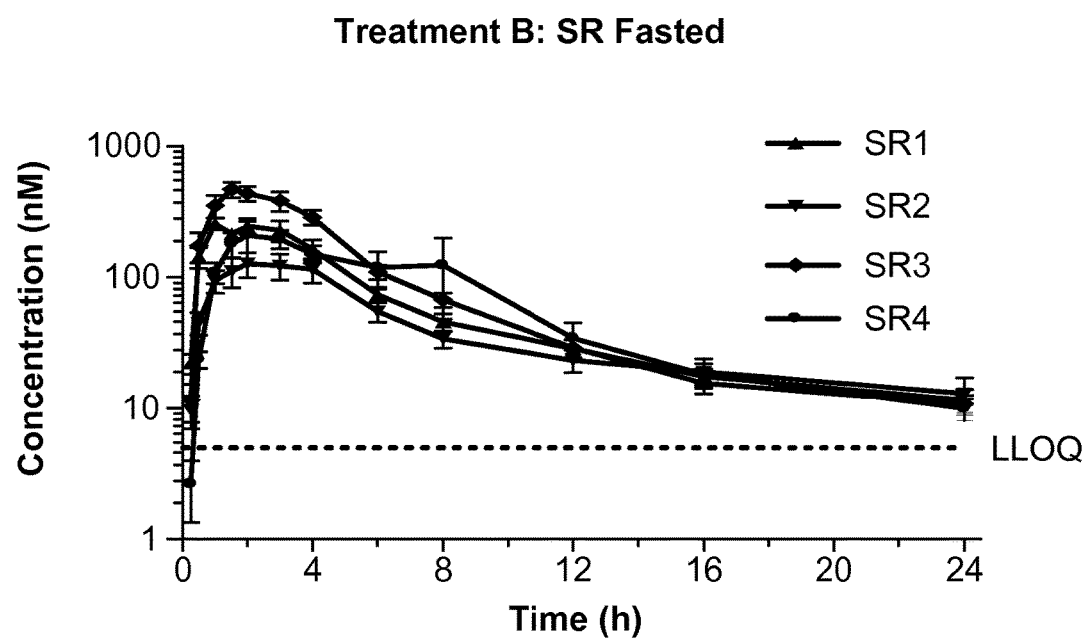
Figure 1C:
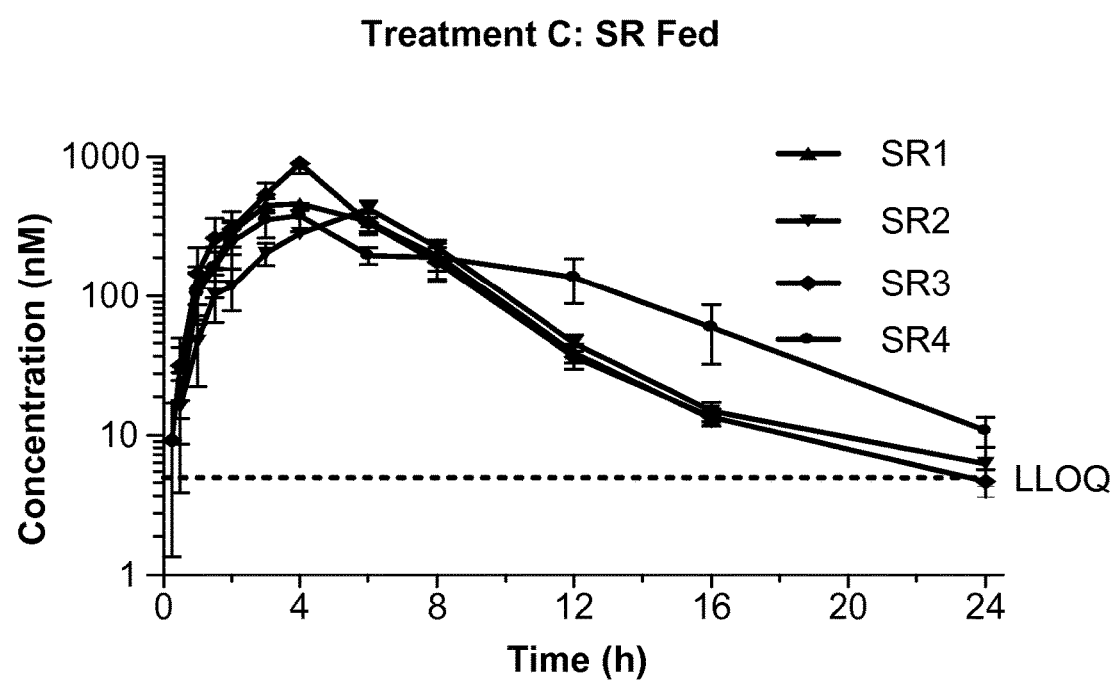
Figure 2A:
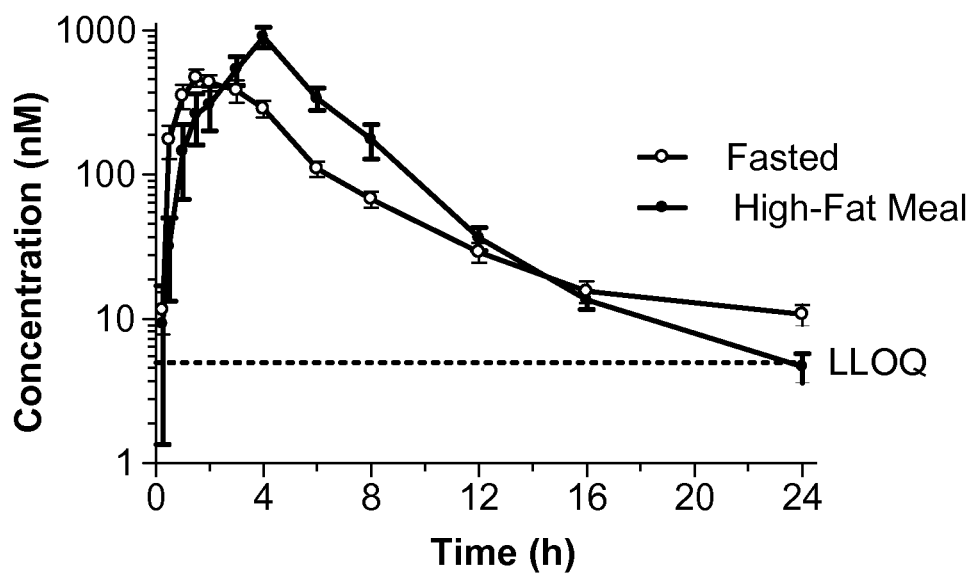
FIG. 2A-B depicts single-dose 300 mg SR3 PK profiles (Mean±SE) (2A: Cohort 3, SR3, fasted versus high-fat meal; and 2B: Cohort 5, SR3, fasted versus medium-fat meal).
Figure 2B:
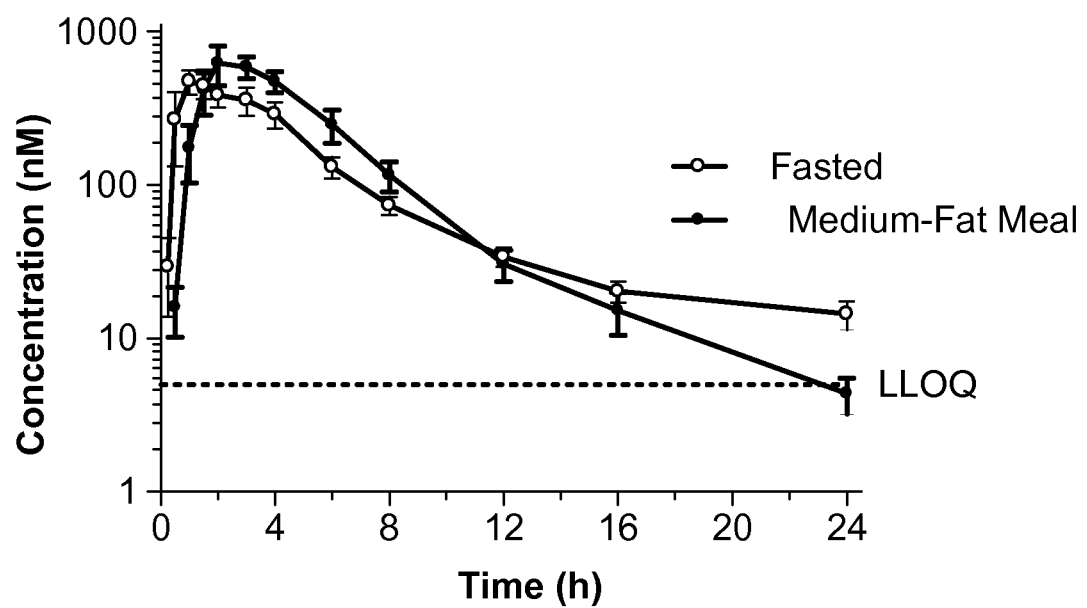
Figure 3:
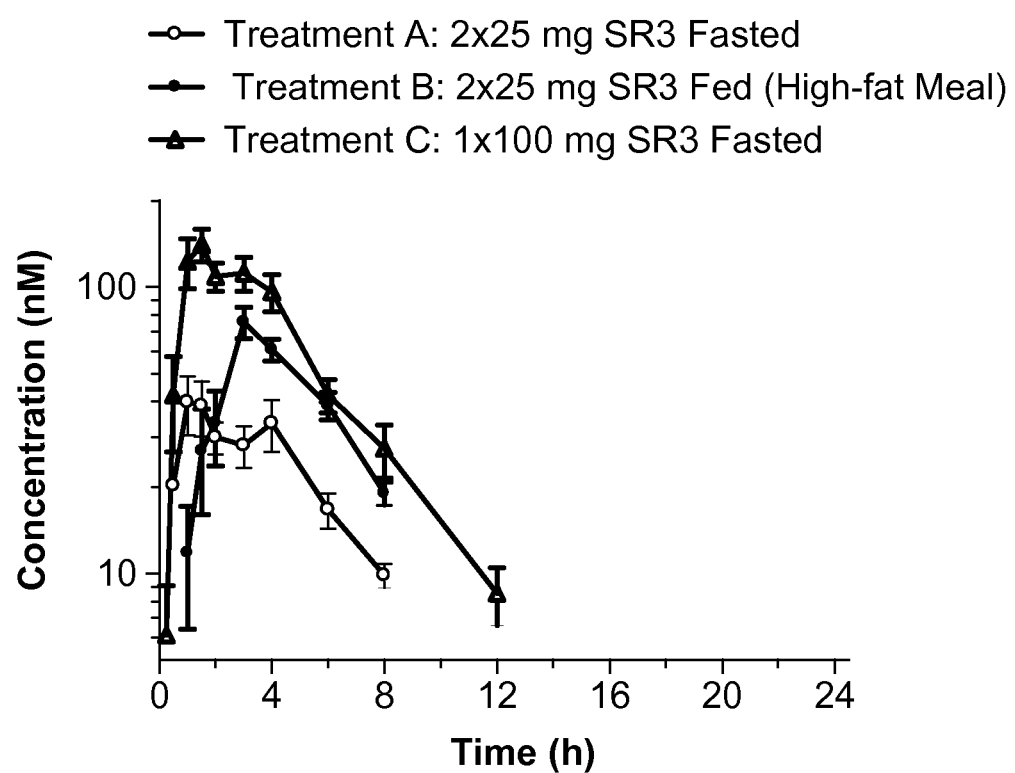
FIG. 3 depicts a comparison of PK profiles (mean±SE) between the 25 mg and 100 mg SR3 tablets (treatment A vs C) and the food effect of a high-fat meal on the 25 mg SR3 tablet (treatment B vs A).

FIG. 1 presents plasma concentrations of the compound of Formula I (mean±SE) for the subjects in Cohorts 1 to 4 following Treatment A (300 mg IR administration in fasted state), Treatment B (300 mg SR administration in fasted state), and Treatment C (300 mg SR administration with a high-fat meal). FIG. 2 compares the effect of a high-fat meal and medium-fat meal on the mean PK profile following a single-dose 300 mg (3×100 mg) administration of the compound of Formula I SR3 tablets. FIG. 3 presents plasma concentrations of the compound of Formula I (mean±SE) for the subjects in Cohort 6 following Treatment A (2×25 mg SR tablet administration in fasted state), Treatment B (2×25 mg SR tablet with a high-fat meal), and Treatment C (1×100 mg SR3 administration in fasted state).

Tables 2A, 2B, 3A and 3B summarize mean PK parameters for subjects in Cohorts 1 to 4, the relative bioavailability (reference=IR capsule) and food effect (high-fat meal) for the 100 mg strength SR1-SR4 tablets. Table 4A and 4B summarize mean PK parameters for subjects in Cohort 5, and food effect (medium-fat meal) for the 100 mg strength SR3 tablet. Table 5A and 5B summarizes mean PK parameters for subjects in Cohort 6, the dose-normalized relative bioavailability (reference=100 mg SR3 tablet), and the food effect (high-fat meal) for the 25 mg SR tablet.

TABLE 2A

| Cohort/Treatment | n | $C_{max}$ (μM) | $T_{max}$ (h) | $C_{max}/C_{12\,h}$ | $t_{1/2}$ (h) |
|---|---|---|---|---|---|
| Cohort 1 | | | | | |
| 300 mg IR (fasted) | 12 | 2.29 ± 0.50 / 2.24 | 1.0 (0.50-2.0) | 197 ± 147 / 159 | 2.0 ± 0.27 / 2.0 |
| 300 mg SR1 (fasted) | 12 | 0.341 ± 0.13 / 0.317 | 1.3 (0.50-3.0) | 13.2 ± 7.8 / 11.6 | 9.2 ± 4.5 / 8.3 |
| 300 mg SR1 (high-fat meal) | 12 | 0.610 ± 0.14 / 0.595 | 4.0 (2.0-8.0) | 18.0 ± 6.4 / 16.8 | 3.2 ± 1.4 / 3.0 |
| Cohort 2 | | | | | |
| 300 mg IR (fasted) | 12 | 2.05 ± 0.67 / 1.92 | 1.0 (0.50-3.0) | 130 ± 72.9 / 112 | 2.1 ± 0.34 / 2.1 |
| 300 mg SR2 (fasted) | 12 | 0.191 ± 0.10 / 0.172 | 2.5 (1.0-4.0) | 11.4 ± 9.9 / 8.60 | 11 ± 8.4 / 9.23 |
| 300 mg SR2 (high-fat meal) | 12 | 0.470 ± 0.16 / 0.443 | 6.0 (1.5-6.0) | 11.0 ± 4.0 / 10.4 | 3.5 ± 2.6 / 3.0 |
| Cohort 3 | | | | | |
| 300 mg IR (fasted) | 11 | 2.35 ± 0.41 / 2.31 | 1.0 (0.50-2.0) | 136 ± 70.8 / 120 | 2.2 ± 0.53 / 2.2 |
| 300 mg SR3 (fasted) | 11 | 0.553 ± 0.24 / 0.502 | 1.5 (0.50-3.0) | 22.9 ± 13.4 / 19.3 | 9.8 ± 8.5 / 7.2 |
| 300 mg SR3 (high-fat meal) | 12 | 1.05 ± 0.47 / 0.968 | 4.0 (1.5-8.0) | 34.9 ± 15.8 / 30.8 | 3.3 ± 1.2 / 3.1 |
| Cohort 4 | | | | | |
| 300 mg IR (fasted) | 12 | 2.94 ± 0.98 / 2.78 | 1.0 (0.25-1.5) | 170 ± 58.6 / 162 | 2.1 ± 0.58 / 2.1 |
| 300 mg SR4 (fasted) | 12 | 0.321 ± 0.27 / 0.249 | 2.0 (1.5-8.1) | 10.3 ± 6.0 / 8.92 | 7.3 ± 5.3 / 6.0 |
| 300 mg SR4 (high-fat meal) | 12 | 0.549 ± 0.28 / 0.481 | 4.0 (2.0-16) | 12.8 ± 14.8 / 6.06 | 4.9 ± 2.6 / 4.4 |

TABLE 2B

| Cohort/Treatment | $AUC_{0-t}$ (μM*h) | $AUC_{0-\infty}$ (μM*h) | CL/F (L/h) |
|---|---|---|---|
| Cohort 1 | | | |
| 300 mg IR (fasted) | 4.43 ± 1.00 / 4.33 | 4.45 ± 1.00 / 4.35 | 127 ± 27.1 / 124 |
| 300 mg SR1 (fasted) | 1.55 ± 0.54 / 1.47 | 1.65 ± 0.54 / 1.57 | 359 ± 106 / 345 |
| 300 mg SR1 (high-fat meal) | 2.88 ± 0.65 / 2.82 | 2.91 ± 0.65 / 2.85 | 194 ± 39.9 / 190 |
| Cohort 2 | | | |
| 300 mg IR (fasted) | 4.45 ± 1.36 / 4.24 | 4.47 ± 1.36 / 4.27 | 134 ± 50.1 / 127 |
| 300 mg SR2 (fasted) | 1.00 ± 037 / 0.95 | 1.17 ± 0.43 / 1.11 | 510 ± 148 / 488 |
| 300 mg SR2 (high-fat meal) | 2.48 ± 0.70 / 2.38 | 2.52 ± 0.72 / 2.42 | 235 ± 83.5 / 224 |
| Cohort 3 | | | |
| 300 mg IR (fasted) | 5.00 ± 1.33 / 4.83 | 5.03 ± 1.34 / 4.87 | 115 ± 32.4 / 111 |
| 300 mg SR3 (fasted) | 2.28 ± 0.71 / 2.17 | 2.39 ± 0.70 / 2.29 | 248 ± 82.8 / 236 |
| 300 mg SR3 (high-fat meal) | 3.55 ± 1.13 / 3.40 | 3.59 ± 1.13 / 3.44 | 165 ± 50.2 / 158 |
| Cohort 4 | | | |
| 300 mg IR (fasted) | 5.23 ± 2.16 / 4.88 | 5.25 ± 2.15 / 4.90 | 117 ± 39.8 / 111 |
| 300 mg SR4 (fasted) | 1.61 ± 1.23 / 1.31 | 1.70 ± 1.25 / 1.40 | 456 ± 259 / 387 |
| 300 mg SR4 (high-fat meal) | 3.00 ± 1.17 / 2.78 | 3.13 ± 1.20 / 2.92 | 200 ± 80.0 / 186 |

TABLE 3A

| Cohort/Treatment | $C_{max}$ (μM) | $T_{max}$ (h) | $C_{max}/C_{12h}$ | $t_{1/2}$ (h) |
|---|---|---|---|---|
| SR1 fasted vs IR | 14.2% (11.4%-17.5%) | | | |
| SR1 fed vs fasted | 188% (152%-232%) | | | |
| SR2 fasted vs IR | 8.9% (6.7%-11.9%) | | | |
| SR2 fed vs fasted | 258% (193%-344%) | | | |
| SR3 fasted vs IR | 22.3% (17.4%-28.6%) | | | |
| SR3 fed vs fasted | 191% (150%-244%) | | | |
| SR4 fasted vs IR | 9.0% (6.8%-11.9%) | | | |
| SR4 fed vs fasted | 193% (146%-256%) | | | |

PK parameter values are mean ± SD and geometric mean except for $T_{max}$, where median (90% confidence interval) is reported.

TABLE 3B

| Cohort/Treatment | $AUC_{0-t}$ (μM*h) | $AUC_{0-\infty}$ (μM*h) | CL/F (L/h) |
|---|---|---|---|
| Geometric Mean Relative Bioavailability and the 90% Confidence Intervals | | | |
| SR1 fasted vs IR | 34.1% (31.3%-37.0%) | 36.1% (33.3%-39.2%) | |
| SR1 fed vs fasted | 191% (176%-208%) | 181% (167%-196%) | |
| SR2 fasted vs IR | 22.4% (18.3%-27.4%) | 26.0% (21.6%-31.3%) | |
| SR2 fed vs fasted | 250% (204%-306%) | 218% (181%-262%) | |
| SR3 fasted vs IR | 45.4% (39.6%-52.0%) | 47.5% (41.9%-53.9%) | |
| SR3 fed vs fasted | 151% (132%-173%) | 145% (128%-164%) | |
| SR4 fasted vs IR | 26.9% (21.6%-33.4%) | 28.5% (23.2%-35.1%) | |
| SR4 fed vs fasted | 213% (171%-264%) | 215% (172%-268%) | |

PK parameter values are mean ± SD and geometric mean except for $T_{max}$, where median (90% confidence interval) is reported.

TABLE 4A

| Cohort/Treatment | n | $C_{max}$ (μM) | $T_{max}$ (h) | $C_{max}/C_{12h}$ | $t_{1/2}$ (h) |
|---|---|---|---|---|---|
| Cohort 5 | | | | | |
| 300 mg SR3 (fasted) | 12 | 0.619 ± 0.41 0.523 | 1.75 (0.50-4.0) | 22.8 ± 16.7 17.8 | 7.7 ± 5.2 6.2 |
| 300 mg SR3 (medium-fat meal) | 12 | 0.875 ± 0.47 0.764 | 2.5 (1.5-6.0) | 40.6 ± 22.7 31.2 | 3.6 ± 2.0 3.3 |
| Geometric Mean Relative Bioavailability and the 90% Confidence Intervals | | | | | |
| SR3 fed vs fasted | | 146% (105%-202%) | | | |

Pharmacokinetic parameter values are mean ± SD and geometric mean except for $T_{max}$, where median (90% confidence interval) is reported.

TABLE 4B

| Cohort/Treatment | $AUC_{0-t}$ (μM*h) | $AUC_{0-\infty}$ (μM*h) | CL/F (L/h) |
|---|---|---|---|
| Cohort 5 | | | |
| 300 mg SR3 (fasted) | 2.46 ± 1.13 2.23 | 2.58 ± 1.12 2.36 | 251 ± 105 230 |
| 300 mg SR3 (medium-fat meal) | 2.98 ± 1.34 2.72 | 3.02 ± 1.35 2.76 | 215 ± 94.2 196 |
| Geometric Mean Relative Bioavailability and the 90% Confidence Intervals | | | |
| SR3 fed vs fasted | 122% (102%-146%) | 117% (99.9%-137%) | |

Pharmacokinetic parameter values are mean ± SD and geometric mean except for $T_{max}$, where median (90% confidence interval) is reported.

TABLE 5A

| Cohort/Treatment | n | $C_{max}$ (nM) | $T_{max}$ (h) | $C_{max}/C_{12h}$ | $t_{1/2}$ (h) |
|---|---|---|---|---|---|
| Cohort 6 | | | | | |
| 2 × 25 mg SR3 (fasted) | 12 | 55.1 ± 30.3 48.0 | 1.3 (0.50-4.0) | NR | 4.0 ± 2.6 3.4 |
| 2 × 25 mg SR3 (high-fat meal) | 12 | 80.3 ± 27.3 76.7 | 3.0 (1.5-6.0) | NR | 2.2 ± 0.4 2.2 |
| 1 × 100 mg SR3 (fasted) | 11 | 174 ± 69.5 161 | 1.8 (0.50-4.0) | NR | 3.0 ± 1.3 2.7 |
| Geometric Mean Relative Bioavailability and the 90% Confidence Confidence Intervals | | | | | |
| 2 × 25 mg SR3 fed vs fasted | | 160% (129%-199%) | | | |
| 2 × 25 mg SR3 vs 1 × 100 mg SR3 (fasted) | | 58.7%[i] (46.9%-73.5%) | | | |

NC = not calculated because of significant numbers of mismatching $T_{last}$ within the subjects between treatments; NR = not reported because significant numbers of $C_{12h}$ values were BQL.
PK parameter values are mean ± SD and geometric mean except for $T_{max}$, where median (90% confidence interval) is reported.
[i]Statistical comparison was dose-normalized.

TABLE 5B

| Cohort/Treatment | $AUC_{0-t}$ (nM*h) | $AUC_{0-\infty}$ (nM*h) | CL/F (L/h) |
|---|---|---|---|
| Cohort 6 | | | |
| 2 × 25 mg SR3 (fasted) | 205 ± 103 183 | 243 ± 99.9 226 | 429 ± 167 400 |
| 2 × 25 mg SR3 (high-fat meal) | 333 ± 104 319 | 376 ± 94.6 366 | 253 ± 57.7 247 |
| 1 × 100 mg SR3 (fasted) | 671 ± 230 639 | 704 ± 230 673 | 280 ± 81.5 268 |
| Geometric Mean Relative Bioavailability and the 90% Confidence Intervals | | | |
| 2 × 25 mg SR3 fed vs fasted | 174% (150%-202%) | 158% (138%-182%) | |
| 2 × 25 mg SR3 vs 1 × 100 mg SR3 (fasted) | NC | 66.1%[i] (57.5%-75.9%) | |

NC = not calculated because of significant numbers of mismatching $T_{last}$ within the subjects between treatments; NR = not reported because significant numbers of $C_{12h}$ values were BQL.
PK parameter values are mean ± SD and geometric mean except for $T_{max}$, where median (90% confidence interval) is reported.
[i]Statistical comparison was dose-normalized.

The mean PK profiles following the fasting single-dose administration of 300 mg IR capsules were similar among the subjects in Cohorts 1 to 4 (FIG. 1). Compared to the IR formulation, following fasting single-dose administration of the SR1-SR4 formulations (3×100 mg tablets), the observed plasma median $T_{max}$ values were moderately prolonged (by 0.3 to 1.5 hours) with significantly reduced mean $C_{max}$ values (the upper bounds of the 90% CI for the geometric mean $C_{max}$ ratios were <30%), suggesting decreased absorption rate of the compound of Formula I for the SR tablets. The apparent mean disposition $t_{1/2}$ observed in the terminal phase was significantly longer, ranging from 7.3 to 11 hours for SR1-SR4, as compared to about 2 hours for the IR capsule, indicating that the systemic elimination of the compound of Formula I was likely rate-limited by its absorption, which was sustained in the terminal disposition phase. As a result of lower $C_{max}$ and longer disposition $t_{1/2}$, the $C_{max}/C_{12h}$ ratios were significantly lower for the SR tablets compared to the IR capsule for the same subjects studied. The geometric mean $C_{max}/C_{12h}$ ratios were 11.6-, 8.6-, 19.3-, and 8.9-fold, respectively, for SR1, SR2, SR3, and SR4 tablets, as compared to 112- to 162-fold for the IR capsules administered in the fasted state.

For administration in the fasted state, the 4 SR tablets showed reduced relative bioavailability compared to the IR capsule dosed in the same subjects. The percent geometric mean ratios (90% CI) of $C_{max}$ were 14.2% (11.4%-17.5%), 8.9% (6.7%-11.9%), 22.3% (17.4%-28.6%) and 9.0% (6.8%-11.9%) for SR1, SR2, SR3, and SR4, respectively. The percent geometric mean ratios (90% CI) of $AUC_{0-\infty}$ were 36.1% (33.3%-39.2%), 26.0% (21.6%-31.3%), 47.5% (41.9%-53.9%), and 28.5% (23.2%-35.1%) for SR1, SR2, SR3, and SR4, respectively. SR3 and SR1 demonstrated the best and second best relative bioavailability, respectively, among the SR formulations tested.

Dosed in the fasted state, the intersubject variability as measured by percent coefficient of variability (CV %) in plasma exposure was significantly higher for the gastroretentive formulation SR4, but comparable among the 3 regular SR tablets designed for intestinal release. The intersubject CV % for the 100 mg SR1 tablet was 39% and 33% for $C_{max}$ and $AUC_{0-\infty}$, respectively. The intersubject CV % for the 100 mg SR2 tablet was 50% and 37% for $C_{max}$ and $AUC_{0-\infty}$, respectively. The intersubject CV % for the 100 mg SR3 tablet was 43% and 29% for $C_{max}$ and $AUC_{0-\infty}$, respectively. The intersubject CV % for the 100 mg SR4 tablet was 83% and 73% for $C_{max}$ and $AUC_{0-\infty}$, respectively. Pooling all subjects in Cohorts 1-5 (n=59) who were administered 300 mg IR in the fasted state, the intersubject CV % was 49% and 39% for $C_{max}$ and $AUC_{0-\infty}$, respectively, comparable to the CV % values observed for SR1, SR2, and SR3.

A positive food effect was observed for all SR formulations studied at the 300 mg (3×100 mg) dose level. Administered after a high-fat meal, geometric mean $C_{max}$ and $AUC_{0-\infty}$ values increased by 88% and 81%, respectively, for SR1; by 158% and 118%, respectively; for SR2; by 91% and 45%; respectively; for SR3; and by 93% and 115%; respectively; for SR4. The food effect was moderate for a medium-fat meal as compared to a high-fat meal, as suggested by the data for SR3 in Cohort 5. For SR3, $C_{max}$ and $AUC_{0-\infty}$ values increased by 46% and 17%, respectively, when it was administered following a standardized medium-fat meal. Administration with food did not significantly change the intersubject CV % in compound of Formula I plasma exposure for SR1, SR2, and SR3, which are SR formulations designed for intra-intestinal release. For SR4, which is a gastroretentive SR formulation, the intersubject CV % in plasma exposures appeared to be significantly reduced with a concomitant high-fat meal.

This study also explored the dose-normalized relative bioavailability of the 25 mg SR tablet in reference to the 100 mg SR3 tablet. For the subjects in Cohort 6, the dose-normalized $C_{max}$ and $AUC_{0-\infty}$ percent geometric mean ratio for the 2×25 mg SR3 treatment was 59% and 66%, respectively, versus the 1×100 mg SR3 administration in the fasted state. However, due to the supralinear dose-exposure relationship for the compound of Formula I, the relative bioavailability of the 25 mg SR tablet may be underestimated. For the 2×25 mg SR dose, a high-fat meal increased compound of Formula I $C_{max}$ and $AUC_{0-\infty}$ by 60% and 58%, respectively.

For the four SR formulations evaluated, the observed apparent disposition $t_{1/2}$ was comparable, and the $C_{max}/C_{12h}$ ratios from a fasting single-dose administration (which is used as a proxy for P/T ratio from twice-daily administration) were similar among SR1, SR2, and SR4 (~10-fold) and moderately higher for SR3 (~20-fold). Overall, all 4 SR formulations demonstrated a significantly flatter PK profile compared the IR capsule, meeting an important objective for sustained release. Bioavailability of orally administered drug products may be defined by the rate and extent of the drug absorption into systemic circulation. A reduction in drug absorption rate by limiting the drug release rate from drug products is a design requirement in sustained release formulations. Therefore, for SR formulations, the extent of the compound of Formula I absorption as measured by the plasma $AUC_{0-\infty}$ is used as the primary endpoint to assess the relative bioavailability. Thus, the mean relative bioavailability is similar between SR2 (26%) and SR4 (29%), which was slightly lower than that of SR1 (36%). The best relative bioavailability was observed for SR3 (48%). The results are in line with the in vitro dissolution profiles obtained before conducting this study.

There was an apparent inverse correlation between the food effect and relative bioavailability for the SR formulations. On average, dosed with a high-fat meal, the food-effect measured by the increase in $AUC_{0-\infty}$ was the greatest for SR2 (118%) and SR4 (115%), which was lower than that for SR1 (81%). The smallest food effect was observed for SR3 (45%). This correlation was also apparent when the data from all the subjects were pooled together. A quantile plot using the pooled individual data (divided into 5 bins with 9 subjects per bin) suggests that the food effect was more significant (>2-fold increase in AUC) for the subjects with relative bioavailability less than 35%, regardless of the formulation. The food effect was moderate (~50% or less increase in AUC) for the subjects with relative bioavailability greater than 40%, regardless of formulation. SR3 delivered a mean relative bioavailability of 48% and is likely to be associated with a moderate food effect. In fact, when the SR3 tablet (3×100 mg) was dosed with a medium-fat meal (which is a more typical daily diet), the observed increase in geometric mean $AUC_{0-\infty}$ was only 17%, suggesting that this formulation may be administered without regard to medium- or low-fat meals. From the perspective of avoiding significant food effect, SR3 is superior to the other formulations.

EXAMPLE 4

Clinical Results in Phase 2a in Patients with Active Rheumatoid Arthritis (RA)

An initial 28 day part of the study was conducted in order to select doses moving forward, guiding dose selection for the 3 month second part of the study. Part 2 of the study was randomized, double-blind, placebo controlled (sponsor unblinded) with treatment for 84 days. Sixty subjects to be randomized, using the same population as in Part 1: single cohort, five parallel treatment groups, 12 subjects each: 100 mg SR3 tablets BID; 300 mg (3×100 mg SR3 tablets) QD; 200 mg (2×100 mg SR3 tablets) BID; 600 mg (6×100 mg SR3 tablets) QD; and placebo. Interim data was submitted to ACR (American College of Rheumatology) 2013 (n=40 subjects who completed day 84). The ACR scores at 3 months are shown in Table 6. The ACR scores for the 600 mg QD are unprecedented as compared to other JAK inhibitors that are approved for treatment of RA. For example, the approved product for tofacitinib citrate (5 mg BID) showed much lower ACR scores at 3 months: 59% (ACR20), 31% (ACR50), and 15% (ACR70) (Table 5 of XELJANZ®—tofacitinib citrate tablet—label).

TABLE 6

|  | Placebo | 100 mg BID | 300 mg QD | 200 mg BID | 600 mg QD |
|---|---|---|---|---|---|
| ACR20 | 38 | 50 | 44 | 50 | 100 |
| ACR50 | 25 | 38 | 44 | 38 | 71 |
| ACR70 | 13 | 25 | 22 | 13 | 57 |

Figure 4A:
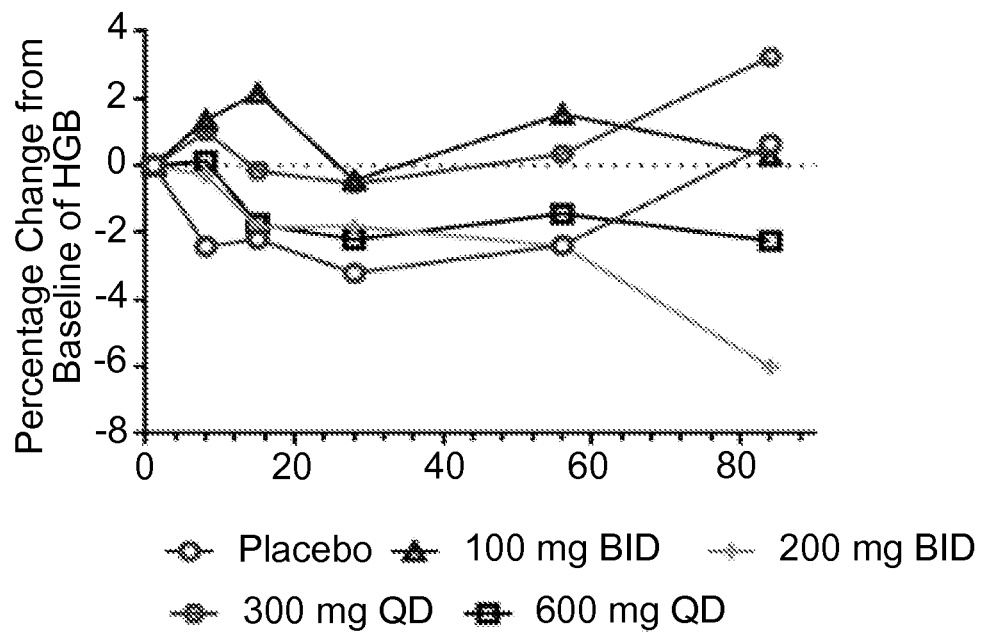
FIG. 4(a)-(b) depicts the percent change from baseline for hemoglobin for several dosing regimens for sustained release tablets versus placebo ((FIG. 4(a) as a function of days.
Figure 4B:
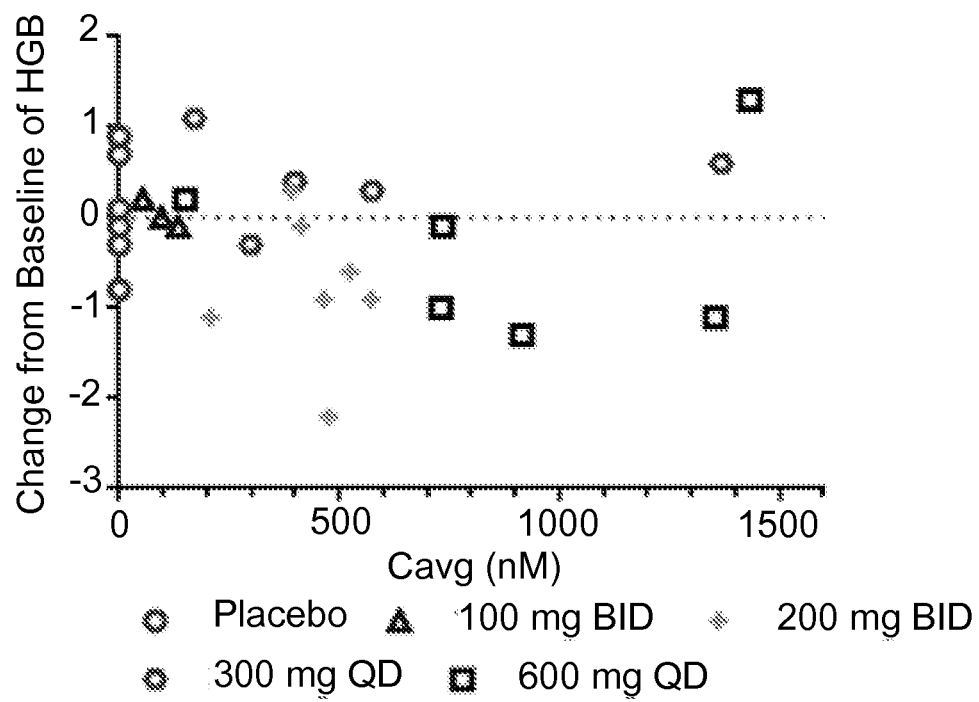

The percent change from baseline for hemoglobin was also studied for each of the dosing regimens (FIG. 4(a) as a function of days; FIG. 4(b) as a function of total average concentration (Cavg)). As can be seen in FIG. 4(a)-(b), the 200 mg BID dose showed a drop away from the baseline compared to the other doses which tended to stay close to the placebo levels. For example, the 600 mg QD dose did not show the same downward trend as shown for the BID dose. However, as can be seen in Table 6, the once-daily dosing (600 mg QD) did not compromise efficacy compared with the BID doses. This indicates that the once-daily dosing (such as 600 mg QD) may achieve maximal efficacy without inducing side-effects such anemia. As shown in FIG. 4 and Table 6, the 600 mg QD dose has robust efficacy with trivial change in hemoglobin levels.

It is believed that this efficacy/side-effect profile may be due to the QD dose achieving maximal JAK1 signaling (tied to efficacy) with low JAK2 inhibition at the trough, as JAK2 signaling is tied to hematopoiesis. This hypothesis is supported by the PK derived JAK1 (IL-6) and JAK2 (TPO) inhibition data for the compound of Formula at various doses (Table 7). In particular, the 600 mg QD dose showed similar average IL-6 inhibition to the 200 mg BID and 400 mg BID doses (61% versus 64% and 69%), but lower trough TPO inhibition in comparison to the 200 mg BID and 400 mg BID doses (4% versus 13% and 16%). The trough IL-6 inhibition for the 600 mg QD dose is also lower than the trough IL-6 inhibition for the 200 mg BID and 400 mg BID doses, which suggests that there may be a reduction in infection from the QD dose.

TABLE 7

| Dose regimen | Average IL-6 inhibition | Trough IL-6 inhibition | Average TPO inhibition | Trough TPO inhibition |
|---|---|---|---|---|
| 100 mg QD | 30% | 7% | 7% | <1% |
| 200 mg QD | 39% | 11% | 11% | <1% |
| 300 mg QD | 47% | 16% | 18% | 1% |
| 600 mg QD | 61% | 31% | 36% | 4% |
| 100 mg BID | 44% | 22% | 11% | 2% |
| 200 mg BID | 64% | 52% | 24% | 13% |
| 400 mg BID | 69% | 56% | 33% | 16% |

EXAMPLE 5

Clinical Results in Patients with Plaque Psoriasis

A double-blind (sponsor unblinded), randomized, placebo controlled study was conducted in approximately 48 subjects treated for 28 days. Eligibility requirements included: active plaque psoriasis for at least 6 months at screening; body surface area (BSA) of plaque psoriasis of ≥5%; psoriasis area and severity index (PASI) score of ≥5; static physician's global assessment (sPGA) score of ≥3; inadequate response to topical therapies; innovative design allowing rapid progress between doses, with conservative safety assessment. Four staggered dose groups of 12 subjects each (9 active and 3 PBO) progressing from 100 mg QD to 200 mg QD to 200 mg BID to 600 mg QD. Once the 4th subject (block of 3 active 1 PBO) completed 28 days administration without a Grade 3 or higher AE, the next group of 12 subjects initiated treatment with the next highest dose; while the first 4 subjects in this group are treated for 28 days, the 1st group is filled 60 subjects with moderate to severe psoriasis were randomized. There were five treatment groups: placebo, 100 mg QD, 200 mg QD, 200 mg BID and 600 mg QD. A sequential method of recruitment was used, increasing from the lowest dose to the highest, each after the completion of 28 days for the first four subjects in the previous dose. The results at 28 days are show in Table 8 (PASI 50 is Psoriasis Area and Severity Index). These PASI 50 score of 81.8% for the 600 mg QD dose are unprecedented as compared to other JAK inhibitors that are in development for treatment of psoriasis. For example, 5 mg tofacitinib (also known as tasocitinib) showed lower PASI 50 score of 65.3% at 12 weeks (published on http://press-.pfizer.com on Oct. 7, 2010). The 5 mg tofacitinib dose is the approved dosage level for RA for safety reasons in the US.

TABLE 8

|  | Placebo | 100 mg BID | 200 mg QD | 200 mg BID | 600 mg QD |
|---|---|---|---|---|---|
| Mean % change sPGA | −12.5% | −22.2% | −29.4% | −35.2% | −42.4% |
| % sPGA (clear or minimal) | 0 | 11.1% | 22.2% | 33.3% | 45.5% |
| % PASI 50 | 8.3% | 22.2% | 66.7% | 44.4% | 81.8% |

EXAMPLE 6

Open-Label Phase II Study in Patients with Myelofibrosis

Figures 5A, 5B:
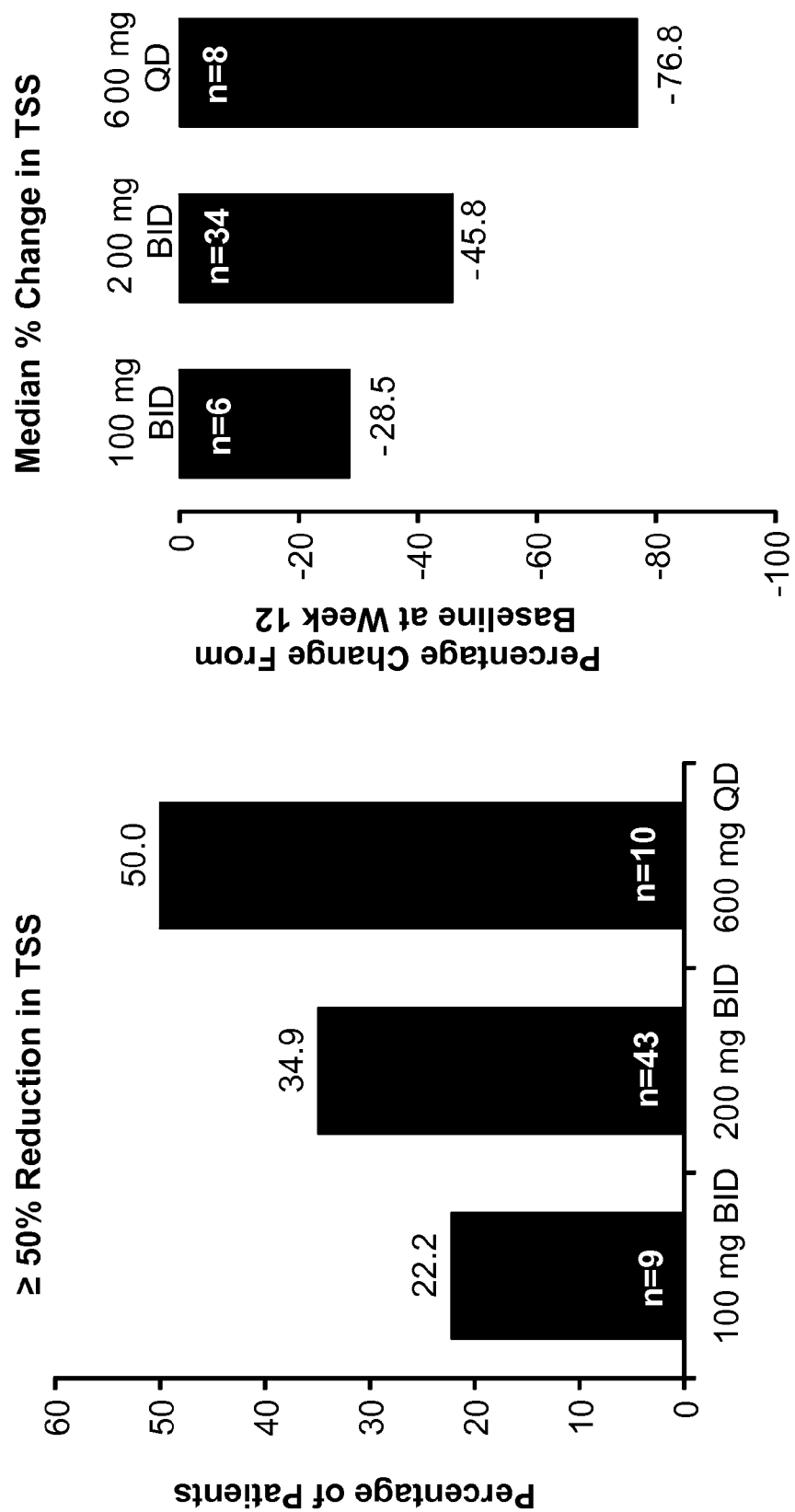
FIG. 5(a) depicts the percentage of patients having a ≥50% reduction in total symptom score (TSS) at week 12 by dose cohort (100 mg BID, 200 mg BID, and 600 mg QD).
FIG. 5(b) depicts the percent change in total symptom score (TSS) from baseline at week 12 by dose cohort (100 mg BID, 200 mg BID, and 600 mg QD).
Figure 6A:
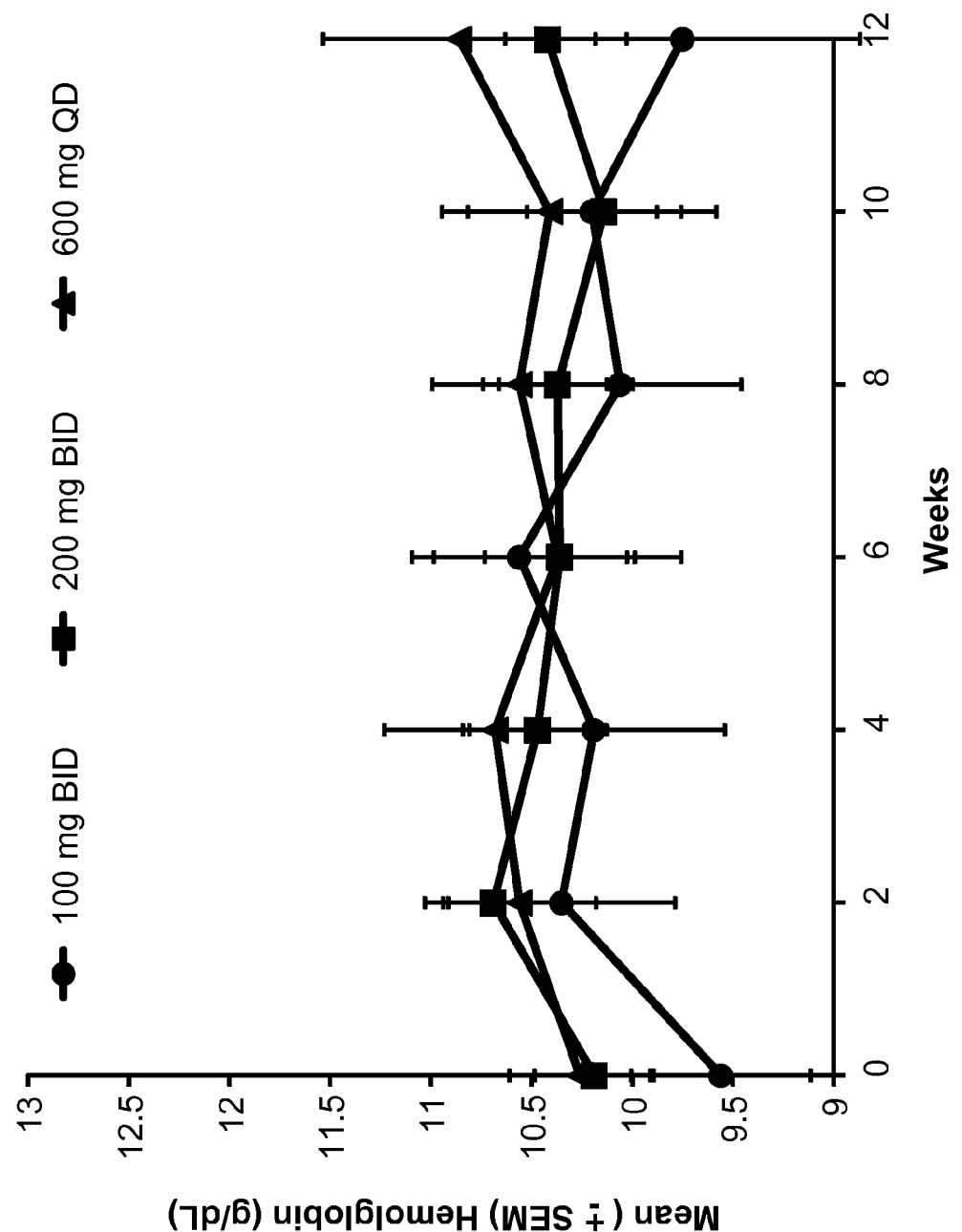
FIG. 6(a) depicts mean hemoglobin levels over time by dose cohort (100 mg BID, 200 mg BID, and 600 mg QD).
Figure 6B:
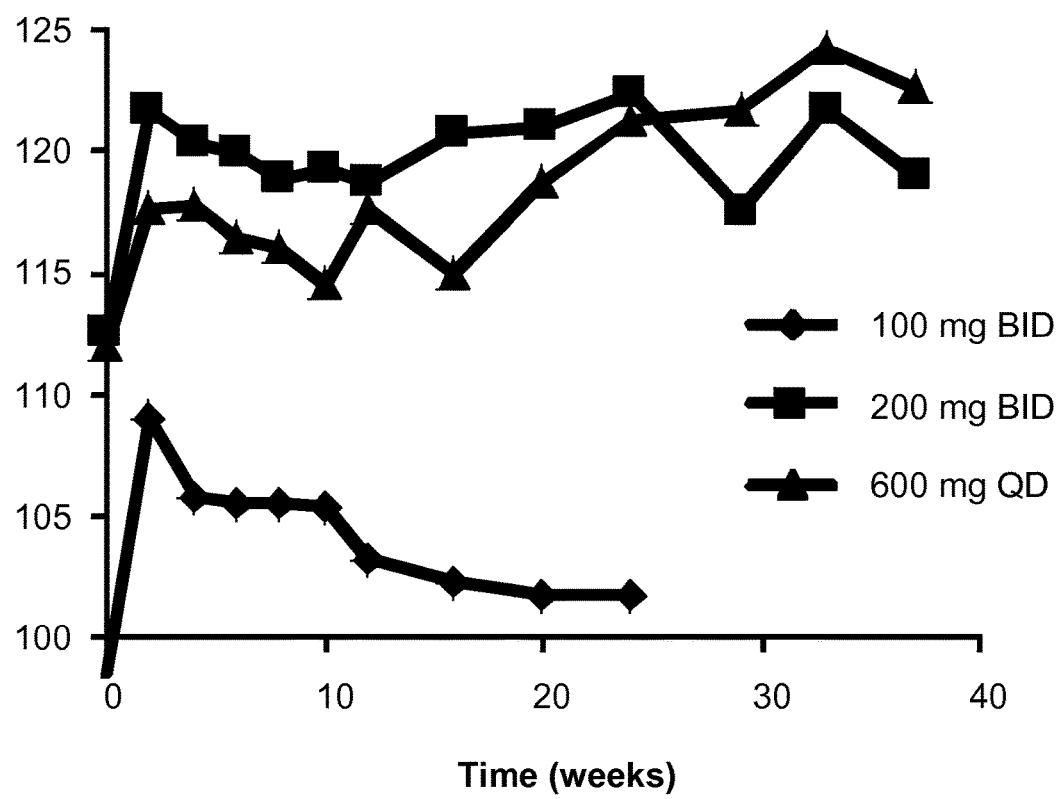
FIG. 6(b) depicts mean hemoglobin levels (g/dL) over time by dose cohort (100 mg BID, 200 mg BID, and 600 mg QD) at 48 weeks.
Figure 6C:
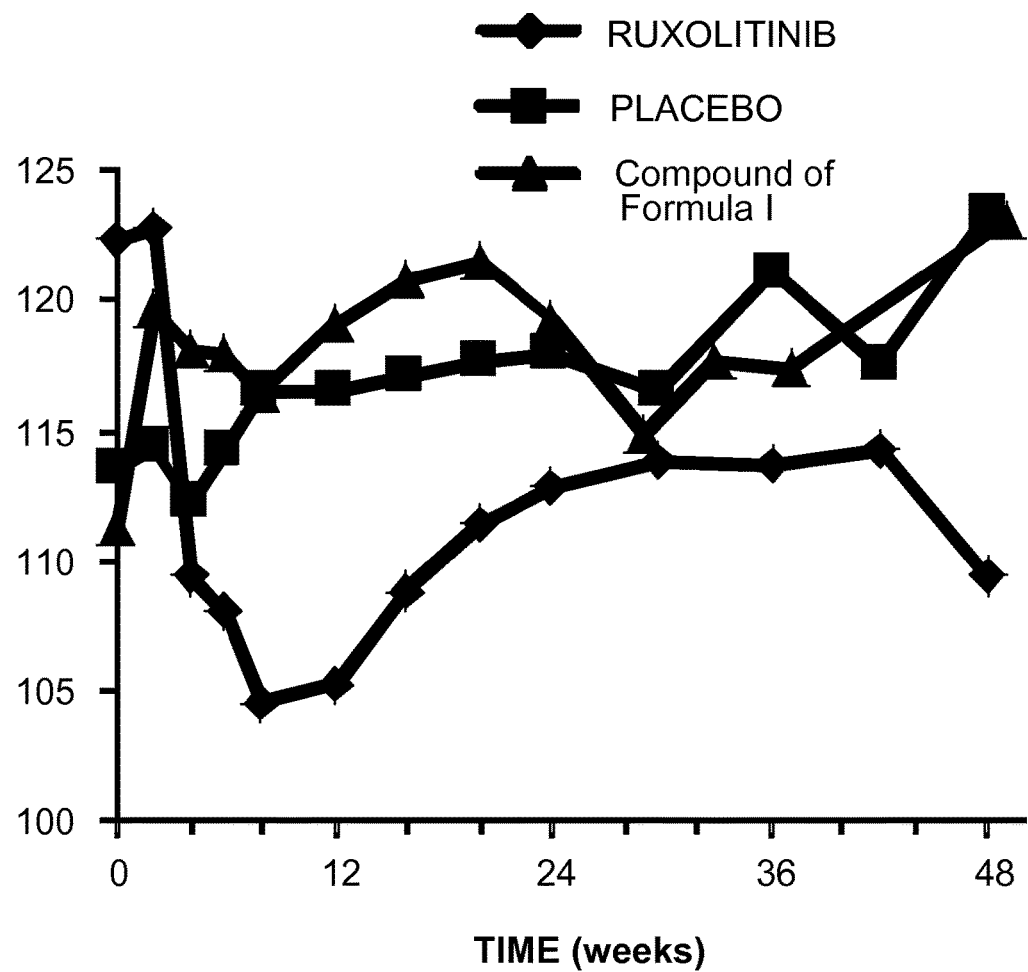
FIG. 6(c) depicts mean hemoglobin levels (g/dL) over time by dose cohort at 48 weeks as an average for three dose cohorts as compared to individuals dosed with placebo or ruxolitinib.

In this study, patients with age ≥18 years, a diagnosis of primary myelofibrosis (PMF) or post-polycythemia vera MF or post-essential thrombocythemia MF (JAK2V617F positive or negative mutation status), platelet counts ≥50×109/L, hemoglobin levels ≥8.0 g/dL (transfusions permitted to achieve these levels), intermediate-1 or higher per DIPSS criteria, and palpable spleen or prior splenectomy were enrolled. Three different dose cohorts were assessed: (1) 100 mg SR3 tablets BID) (2) 200 mg (2×100 mg SR3 tablets) BID; and (3) 600 mg (6×100 mg SR3 tablets) QD. FIG. 5(a)-(b) show interim results with respect to proportion of subjects with ≥50% reduction in total symptom score (TSS) in each dose group per the modified Myelofibrosis Symptom Assessment Form (MFSAF) v3.0 electronic diary at week 12 compared with baseline (The modified MFSAF v3.0 comprises 19 questions assessing MF-related symptoms on a scale of 0 (absent) to 10 (worst imaginable)). FIG. 5(a) depicts the percentage of patients having a ≥50% reduction in TSS at week 12 by dose cohort (100 mg BID, 200 mg BID, and 600 mg QD) (patients who discontinued prior to the week 12 visit were considered nonresponders). FIG. 5(b) depicts the percent change in TSS from baseline at week 12 by dose cohort (100 mg BID, 200 mg BID, and 600 mg QD) (only patients with baseline and week 12 data were included). FIG. 6(a) depicts mean hemoglobin levels (g/dL) over time by dose cohort (100 mg BID, 200 mg BID, and 600 mg QD) (interim results of study for all patients). FIG. 6(b) depicts mean hemoglobin levels (g/dL) over time by dose cohort (100 mg BID, 200 mg BID, and 600 mg QD) at 48 weeks. FIG. 6(c) depicts mean hemoglobin levels (g/dL) over time by dose cohort at 48 weeks as an average for three dose cohorts as compared to individuals dosed with placebo or ruxolitinib (ruxolitinib was dosed according to the label for Jakafi®). The data show an increase in hemoglobin levels for the 600 mg QD dose. Finally, Table 9 below show interim hematology laboratory results (new and worsening) for each dose cohort. Table 9a shows the hematology laboratory results (new and worsening) for each dose cohort after long exposure.

TABLE 9

| | N % | | |
|---|---|---|---|
| Event n | 100 mg BID | 200 mg BID | 600 mg QD |
| Days of Exposure, median (range) | 102.5 (23.0, 376.0) | 169.0 (22.0, 339.0) | 16.0 (1.0, 196.0) |
| Anemia, Grade 3 | 3/9 (33.3) | 12/42 (28.6) | 2/29 (6.9) |
| Thrombocytopenia | | | |
| Grade 3 | 4/9 (44.4) | 12/44 (27.3) | 1/29 (3.4) |
| Grade 4 | 0/9 (0) | 2/45 (4.4) | 0/29 (0) |

TABLE 9a

| | N % | | |
|---|---|---|---|
| Event n | 100 mg BID (N = 10) | 200 mg BID (N = 45) | 600 mg QD (N = 32) |
| Days of Exposure, median (range) | 102.0 (23, 519) | 254.0 (22, 535) | 192.0 (28, 343) |
| Anemia, Grade 3 | 3/10 (30.0) | 19/45 (42.2) | 8/32 (25.0) |
| Thrombocytopenia | | | |
| Grade 3 | 4/10 (40.0) | 13/45 (28.9) | 4/32 (12.5) |
| Grade 4 | 0/10 (0.0) | 3/45 (6.7) | 1/32 (3.1) |

EXAMPLE A

In Vitro JAK Kinase Assay

The compound of Formula I herein was tested for inhibitory activity of JAK targets according to the following in vitro assay described in Park et al., *Analytical Biochemistry* 1999, 269, 94-104. The catalytic domains of human JAK1 (a.a. 837-1142) and JAK2 (a.a. 828-1132) with an N-terminal His tag were expressed using baculovirus in insect cells and purified. The catalytic activity of JAK1 and JAK2 was assayed by measuring the phosphorylation of a biotinylated peptide. The phosphorylated peptide was detected by homogenous time resolved fluorescence (HTRF). $IC_{50}$s of compounds were measured for each kinase in the 40 microL reactions that contain the enzyme, ATP and 500 nM peptide in 50 mM Tris (pH 7.8) buffer with 100 mM NaCl, 5 mM DTT, and 0.1 mg/mL (0.01%) BSA. For the 1 mM $IC_{50}$ measurements, ATP concentration in the reactions was 1 mM. Reactions were carried out at room temperature for 1 hr and then stopped with 20 μL 45 mM EDTA, 300 nM SA-APC, 6 nM Eu-Py20 in assay buffer (Perkin Elmer, Boston, Mass.). Binding to the Europium labeled antibody took place for 40 minutes and HTRF signal was measured on a Fusion plate reader (Perkin Elmer, Boston, Mass.). The compound of Formula I and the adipic acid salt had an $IC_{50}$ at JAK1 of ≤5 nM (measured at 1 mM ATP) with a JAK2/JAK1 ratio of >10 (measured at 1 mM ATP).

EXAMPLE B

Cellular Assays

Cancer cell lines dependent on cytokines and hence JAK/STAT signal transduction, for growth, can be plated at 6000 cells per well (96 well plate format) in RPMI 1640, 10% FBS, and 1 ng/mL of appropriate cytokine. Compounds can be added to the cells in DMSO/media (final concentration 0.2% DMSO) and incubated for 72 hours at 37° C., 5% $CO_2$. The effect of compound on cell viability is assessed using the CellTiter-Glo Luminescent Cell Viability Assay (Promega) followed by TopCount (Perkin Elmer, Boston, Mass.) quantitation. Potential off-target effects of compounds are measured in parallel using a non-JAK driven cell line with the same assay readout. All experiments are typically performed in duplicate.

The above cell lines can also be used to examine the effects of compounds on phosphorylation of JAK kinases or potential downstream substrates such as STAT proteins, Akt, Shp2, or Erk. These experiments can be performed following an overnight cytokine starvation, followed by a brief preincubation with compound (2 hours or less) and cytokine stimulation of approximately 1 hour or less. Proteins are then extracted from cells and analyzed by techniques familiar to those schooled in the art including Western blotting or ELISAs using antibodies that can differentiate between phosphorylated and total protein. These experiments can utilize normal or cancer cells to investigate the activity of compounds on tumor cell survival biology or on mediators of inflammatory disease. For example, with regards to the latter, cytokines such as IL-6, IL-12, IL-23, or IFN can be used to stimulate JAK activation resulting in phosphorylation of STAT protein(s) and potentially in transcriptional profiles (assessed by array or qPCR technology) or production and/or secretion of proteins, such as IL-17. The ability of compounds to inhibit these cytokine mediated effects can be measured using techniques common to those schooled in the art.

Compounds herein can also be tested in cellular models designed to evaluate their potency and activity against mutant JAKs, for example, the JAK2V617F mutation found in myeloid proliferative disorders. These experiments often utilize cytokine dependent cells of hematological lineage (e.g. BaF/3) into which the wild-type or mutant JAK kinases are ectopically expressed (James, C., et al. *Nature* 434:1144-1148; Staerk, J., et al. JBC 280:41893-41899). Endpoints include the effects of compounds on cell survival, proliferation, and phosphorylated JAK, STAT, Akt, or Erk proteins.

Certain compounds herein can be evaluated for their activity inhibiting T-cell proliferation. Such as assay can be considered a second cytokine (i.e. JAK) driven proliferation assay and also a simplistic assay of immune suppression or inhibition of immune activation. The following is a brief outline of how such experiments can be performed. Peripheral blood mononuclear cells (PBMCs) are prepared from human whole blood samples using Ficoll Hypaque separation method and T-cells (fraction 2000) can be obtained from PBMCs by elutriation. Freshly isolated human T-cells can be maintained in culture medium (RPMI 1640 supplemented with 10% fetal bovine serum, 100 U/ml penicillin, 100 µg/ml streptomycin) at a density of $2\times10^6$ cells/ml at 37° C. for up to 2 days. For IL-2 stimulated cell proliferation analysis, T-cells are first treated with Phytohemagglutinin (PHA) at a final concentration of 10 µg/mL for 72 h. After washing once with PBS, 6000 cells/well are plated in 96-well plates and treated with compounds at different concentrations in the culture medium in the presence of 100 U/mL human IL-2 (ProSpec-Tany TechnoGene; Rehovot, Israel). The plates are incubated at 37° C. for 72 h and the proliferation index is assessed using CellTiter-Glo Luminescent reagents following the manufactory suggested protocol (Promega; Madison, Wis.).

EXAMPLE C

In Vivo Anti-Tumor Efficacy

Compounds herein can be evaluated in human tumor xenograft models in immune compromised mice. For example, a tumorigenic variant of the INA-6 plasmacytoma cell line can be used to inoculate SCID mice subcutaneously (Burger, R., et al. *Hematol J.* 2:42-53, 2001). Tumor bearing animals can then be randomized into drug or vehicle treatment groups and different doses of compounds can be administered by any number of the usual routes including oral, i.p., or continuous infusion using implantable pumps. Tumor growth is followed over time using calipers. Further, tumor samples can be harvested at any time after the initiation of treatment for analysis as described above (Example B) to evaluate compound effects on JAK activity and downstream signaling pathways. In addition, selectivity of the compound(s) can be assessed using xenograft tumor models that are driven by other know kinases (e.g. Bcr-Abl) such as the K562 tumor model.

EXAMPLE D

Murine Skin Contact Delayed Hypersensitivity Response Test

Compounds herein can also be tested for their efficacies (of inhibiting JAK targets) in the T-cell driven murine delayed hypersensitivity test model. The murine skin contact delayed-type hypersensitivity (DTH) response is considered to be a valid model of clinical contact dermatitis, and other T-lymphocyte mediated immune disorders of the skin, such as psoriasis (*Immunol Today.* 1998 January; 19(1):37-44). Murine DTH shares multiple characteristics with psoriasis, including the immune infiltrate, the accompanying increase in inflammatory cytokines, and keratinocyte hyperproliferation. Furthermore, many classes of agents that are efficacious in treating psoriasis in the clinic are also effective inhibitors of the DTH response in mice (Agents Actions. 1993 January; 38(1-2):116-21).

On Day 0 and 1, Balb/c mice are sensitized with a topical application, to their shaved abdomen with the antigen 2,4, dinitro-fluorobenzene (DNFB). On day 5, ears are measured for thickness using an engineer's micrometer. This measurement is recorded and used as a baseline. Both of the animals' ears are then challenged by a topical application of DNFB in a total of 20 µL (10 µL on the internal pinna and 10 µL on the external pinna) at a concentration of 0.2%. Twenty-four to seventy-two hours after the challenge, ears are measured again. Treatment with the test compounds is given throughout the sensitization and challenge phases (day-1 to day 7) or prior to and throughout the challenge phase (usually afternoon of day 4 to day 7). Treatment of the test compounds (in different concentration) is administered either systemically or topically (topical application of the treatment to the ears). Efficacies of the test compounds are indicated by a reduction in ear swelling comparing to the situation without the treatment. Compounds causing a reduction of 20% or more were considered efficacious. In some experiments, the mice are challenged but not sensitized (negative control).

The inhibitive effect (inhibiting activation of the JAK-STAT pathways) of the test compounds can be confirmed by immunohistochemical analysis. Activation of the JAK-STAT pathway(s) results in the formation and translocation of functional transcription factors. Further, the influx of immune cells and the increased proliferation of keratinocytes should also provide unique expression profile changes in the ear that can be investigated and quantified. Formalin fixed and paraffin embedded ear sections (harvested after the challenge phase in the DTH model) are subjected to immunohistochemical analysis using an antibody that specifically interacts with phosphorylated STAT3 (clone 58E12, Cell Signaling Technologies). The mouse ears are treated with test compounds, vehicle, or dexamethasone (a clinically efficacious treatment for psoriasis), or without any treatment, in the DTH model for comparisons. Test compounds and the dexamethasone can produce similar transcriptional changes both qualitatively and quantitatively, and both the test compounds and dexamethasone can reduce the number of infiltrating cells. Both systemically and topical administration of the test compounds can produce inhibitive effects, i.e., reduction in the number of infiltrating cells and inhibition of the transcriptional changes.

EXAMPLE E

In Vivo Anti-Inflammatory Activity

Compounds herein can be evaluated in rodent or non-rodent models designed to replicate a single or complex inflammation response. For instance, rodent models of arthritis can be used to evaluate the therapeutic potential of compounds dosed preventatively or therapeutically. These models include but are not limited to mouse or rat collagen-induced arthritis, rat adjuvant-induced arthritis, and collagen antibody-induced arthritis. Autoimmune diseases including, but not limited to, multiple sclerosis, type I-diabetes mellitus, uveoretinitis, thyroditis, myasthenia gravis, immunoglobulin nephropathies, myocarditis, airway sensitization (asthma), lupus, or colitis may also be used to evaluate the therapeutic potential of compounds herein. These models are well established in the research community and are familiar to those schooled in the art (Current Protocols in Immunology, Vol 3., Coligan, J. E. et al, Wiley Press.; *Methods in Molecular Biology*: Vol. 225, Inflammation Protocols., Winyard, P. G. and Willoughby, D. A., Humana Press, 2003).

EXAMPLE F

Animal Models for the Treatment of Dry Eye, Uveitis, and Conjunctivitis

Agents may be evaluated in one or more preclinical models of dry eye known to those schooled in the art including, but not limited to, the rabbit concanavalin A (ConA) lacrimal gland model, the scopolamine mouse model (subcutaneous or transdermal), the Botulinumn mouse lacrimal gland model, or any of a number of spontaneous rodent autoimmune models that result in ocular gland dysfunction (e.g. NOD-SCID, MRL/lpr, or NZB/NZW) (Barabino et al., Experimental Eye Research 2004, 79, 613-621 and Schrader et al., Developmental Opthalmology, Karger 2008, 41, 298-312, each of which is incorporated herein by reference in its entirety). Endpoints in these models may include histopathology of the ocular glands and eye (cornea, etc.) and possibly the classic Schirmer test or modified versions thereof (Barabino et al.) which measure tear production. Activity may be assessed by dosing via multiple routes of administration (e.g. systemic or topical) which may begin prior to or after measurable disease exists.

Agents may be evaluated in one or more preclinical models of uveitis known to those schooled in the art. These include, but are not limited to, models of experimental autoimmune uveitis (EAU) and endotoxin induced uveitis (EIU). EAU experiments may be performed in the rabbit, rat, or mouse and may involve passive or activate immunization. For instance, any of a number or retinal antigens may be used to sensitize animals to a relevant immunogen after which animals may be challenged ocuarly with the same antigen. The EIU model is more acute and involves local or systemic administration of lipopolysaccharide at sublethal doses. Endpoints for both the EIU and EAU models may include fundoscopic exam, histopathology amongst others. These models are reviewed by Smith et al. (Immunology and Cell Biology 1998, 76, 497-512, which is incorporated herein by reference in its entirety). Activity is assessed by dosing via multiple routes of administration (e.g. systemic or topical) which may begin prior to or after measurable disease exists. Some models listed above may also develop scleritis/episcleritis, chorioditis, cyclitis, or iritis and are therefore useful in investigating the potential activity of compounds for the therapeutic treatment of these diseases.

Agents may also be evaluated in one or more preclinical models of conjunctivitis known those schooled in the art. These include, but are not limited to, rodent models utilizing guinea-pig, rat, or mouse. The guinea-pig models include those utilizing active or passive immunization and/or immune challenge protocols with antigens such as ovalbumin or ragweed (reviewed in Groneberg, D. A., et al., Allergy 2003, 58, 1101-1113, which is incorporated herein by reference in its entirety). Rat and mouse models are similar in general design to those in the guinea-pig (also reviewed by Groneberg). Activity may be assessed by dosing via multiple routes of administration (e.g. systemic or topical) which may begin prior to or after measurable disease exists. Endpoints for such studies may include, for example, histological, immunological, biochemical, or molecular analysis of ocular tissues such as the conjunctiva.

EXAMPLE G

In Vivo Protection of Bone

Compounds may be evaluated in various preclinical models of osteopenia, osteoporosis, or bone resorption known to those schooled in the art. For example, ovariectomized rodents may be used to evaluate the ability of compounds to affect signs and markers of bone remodeling and/or density (W. S. S. Jee and W. Yao, J. Musculoskel. Nueron. Interact., 2001, 1(3), 193-207, which is incorporated herein by reference in its entirety). Alternatively, bone density and architecture may be evaluated in control or compound treated rodents in models of therapy (e.g. glucocorticoid) induced osteopenia (Yao, et al. Arthritis and Rheumatism, 2008, 58(6), 3485-3497; and id. 58(11), 1674-1686, both of which are incorporated herein by reference in its entirety). In addition, the effects of compounds on bone resorption and density may be evaluable in the rodent models of arthritis discussed above (Example E). Endpoints for all these models may vary but often include histological and radiological assessments as well as immunohisotology and appropriate biochemical markers of bone remodeling.

What is claimed is:

1. A method of treating a disease selected from psoriasis, rheumatoid arthritis, primary myelofibrosis (PMF), post-polycythemia vera myelofibrosis, and post-essential thrombocythemia myelofibrosis in a patient in need thereof, comprising orally administering to said patient a once-daily dose of about 400 mg to about 600 mg on a free base basis of {1-{1-[3-fluoro-2-(trifluoromethyl)isonicotinoyl]piperidin-4-yl}-3-[4-(7H-pyrrolo-[2,3-d]pyrimidin-4-yl)-1H-pyrazol-1-yl]azetidin-3-yl}acetonitrile, or a pharmaceutically acceptable salt thereof, wherein the dose comprises one or more sustained release dosage forms each comprising {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or a pharmaceutically acceptable salt thereof, wherein treating refers to inhibiting or ameliorating the disease.

2. A method according to claim 1, wherein the method comprises administering to said patient the one or more sustained release dosage forms as a once-daily dosage of about 600 mg on a free base basis of {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or a pharmaceutically acceptable salt thereof.

3. A method according to claim 1, wherein the one or more sustained release dosage forms are six dosage forms of about 100 mg on a free base basis of {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or a pharmaceutically acceptable salt thereof.

4. A method according to claim 1, wherein the one or more sustained release dosage forms are three dosage forms of about 200 mg on a free base basis of {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or a pharmaceutically acceptable salt thereof.

5. A method according to claim 1, wherein the one or more sustained release dosage forms are two dosage forms of about 300 mg on a free base basis of {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile, or a pharmaceutically acceptable salt thereof.

6. A method according to claim 1, wherein the one or more sustained release dosage forms is one dosage form of about 600 mg on a free base basis of {1-{1-[3-fluoro-2-(trifluoromethyl)isonicotinoyl]piperidin-4-yl}-3-[4-(7H- pyrrolo[2,3-d]pyrimidin-4-yl)-1H-pyrazol-1-yl}azetidin-3-yl}acetonitrile, or a pharmaceutically acceptable salt thereof.

7. A method according to claim 2, wherein said disease is rheumatoid arthritis.

8. A method according to claim 7, wherein the American College of Rheumatology-70 score (ACR70) of said patient is greater than about 40%.

9. A method according to claim 7, wherein the American College of Rheumatology-70 score (ACR70) of said patient is greater than about 50%.

10. A method according to claim 2, wherein said disease is psoriasis.

11. A method according to claim 10, wherein the Psoriasis Area and Severity Index-50 score (PASI 50) is greater than about 70%.

12. A method according to claim 2, wherein said disease is primary myelofibrosis (PMF).

13. A method according to claim 12, wherein the method results in a reduced total symptom score (TSS) of said patient compared with baseline.

14. A method according to claim 12, wherein said method results in reduced anemia.

15. A method according to claim 2, wherein oral administration of one or more sustained release dosage forms to a fasted individual provides a mean time to peak plasma concentration ($T_{max}$) of {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile of about 0.5 hours to about 3 hours.

16. A method according to claim 2, wherein oral administration of one or more sustained release dosage forms to a fasted individual provides a ratio of mean peak plasma concentration ($C_{max}$) to mean 12-hour plasma concentration ($C_{12h}$) of {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile of about 15 to about 30.

17. A method according to claim 2, wherein oral administration of one or more sustained release dosage forms to an individual after a high-fat meal provides a mean time to peak plasma concentration ($T_{max}$) of {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile of at least 1.5 hours.

18. A method according to claim 2, wherein oral administration of one or more sustained release dosage forms to an individual after a high-fat meal provides a ratio of mean peak plasma concentration ($C_{max}$) to mean 12-hour plasma concentration ($C_{12h}$) of {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile of about 25 to about 45.

19. A method according to claim 2, wherein oral administration of one or more sustained release dosage forms to an individual after a high-fat meal provides a mean half-life ($t_{1/2}$) of {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile of about 2 hours to about 5 hours.

20. A method according to claim 2, wherein the one or more sustained release dosage forms are each a tablet.

21. A method according to claim 20, wherein the one or more sustained release dosage forms are prepared by process comprising wet granulation.

22. A method according to claim 21, wherein the one or more sustained release dosage forms each comprises one or more hypromelloses.

23. A method according to claim 21, wherein the one or more sustained release dosage forms each comprises one or more excipients independently selected from hypromelloses and microcrystalline celluloses.

24. A method according to claim 21, wherein the one or more sustained release dosage forms each comprises one or more excipients independently selected from hypromelloses, microcrystalline celluloses, magnesium stearate, lactose, and lactose monohydrate.

25. A method according to claim 21, wherein the one or more sustained release dosage forms each comprises a first hypromellose characterized by having an apparent viscosity at a concentration of 2% in water of about 80 cP to about 120 cP and a second hypromellose characterized by having an apparent viscosity at a concentration of 2% in water of about 3000 cP to about 5600 cP.

26. A method according to claim 21, wherein the one or more sustained release dosage forms each comprises about 10% to about 15% by weight of one or more hypromelloses.

27. A method according to claim 21, wherein the one or more sustained release dosage forms each comprises about 16% to about 22% by weight of microcrystalline cellulose.

28. A method according to claim 21, wherein the one or more sustained release dosage forms each comprises about 45% to about 55% by weight of lactose monohydrate.

29. A method according to claim 2, wherein said salt is {1-{1-[3-fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile adipic acid salt.

30. The method of claim 2, wherein the disease is post-polycythemia vera myelofibrosis.

31. The method of claim 2, wherein the disease is post-essential thrombocythemia myelofibrosis.

* * * * *